(12) United States Patent
Bedoya et al.

(10) Patent No.: US 9,765,333 B2
(45) Date of Patent: Sep. 19, 2017

(54) COMPOSITIONS AND METHODS FOR SILENCING MARBURG VIRUS GENE EXPRESSION

(71) Applicant: PROTIVA BIOTHERAPEUTICS, INC., Burnaby (CA)

(72) Inventors: Raul J. Ursic Bedoya, Burnaby (CA); Ian MacLachlan, Mission (CA); Marjorie Ann Robbins, Vancouver (CA)

(73) Assignee: PROTIVA BIOTHERAPEUTICS, INC., Burnaby, BC (CA)

( * ) Notice: Subject to any disclaimer, the term of this patent is extended or adjusted under 35 U.S.C. 154(b) by 32 days.

(21) Appl. No.: 14/832,633

(22) Filed: Aug. 21, 2015

(65) Prior Publication Data

US 2016/0076035 A1    Mar. 17, 2016

Related U.S. Application Data

(60) Provisional application No. 62/040,339, filed on Aug. 21, 2014.

(51) Int. Cl.
*A61K 31/713* (2006.01)
*C12N 15/113* (2010.01)
*A61K 31/712* (2006.01)
*A61K 31/00* (2006.01)

(52) U.S. Cl.
CPC .......... *C12N 15/1131* (2013.01); *A61K 31/00* (2013.01); *A61K 31/712* (2013.01); *A61K 31/713* (2013.01); *C12N 2310/14* (2013.01); *C12N 2310/321* (2013.01); *C12N 2320/31* (2013.01); *C12N 2320/32* (2013.01)

(58) Field of Classification Search
USPC .......... 435/6.1, 6.11, 91.1, 91.31, 455, 458; 514/44; 536/23.1, 24.5
See application file for complete search history.

(56) References Cited

U.S. PATENT DOCUMENTS

| | | |
|---|---|---|
| 7,838,658 B2 | 11/2010 | MacLachlan et al. |
| 7,901,708 B2 | 3/2011 | MacLachlan et al. |
| 8,058,069 B2 | 11/2011 | Yaworski et al. |
| 8,101,741 B2 | 1/2012 | MacLachlan et al. |
| 8,188,263 B2 | 5/2012 | MacLachlan et al. |
| 8,329,070 B2 | 12/2012 | MacLachlan et al. |
| 8,455,455 B1 | 6/2013 | Robbins et al. |
| 8,492,359 B2 | 7/2013 | Yaworski et al. |
| 8,513,403 B2 | 8/2013 | MacLachlan et al. |
| 8,822,668 B2 | 9/2014 | Yaworski et al. |
| 9,005,654 B2 | 4/2015 | MacLachlan et al. |
| 9,006,191 B2 | 4/2015 | MacLachlan et al. |
| 9,074,208 B2 | 7/2015 | MacLachlan et al. |
| 2007/0135370 A1* | 6/2007 | MacLachlan ...... C12N 15/1131 514/44 A |
| 2013/0123338 A1 | 5/2013 | Heyes et al. |
| 2014/0044772 A1 | 2/2014 | MacLachlan et al. |
| 2014/0294937 A1 | 10/2014 | MacLachlan et al. |
| 2015/0164799 A1 | 6/2015 | Yaworski et al. |
| 2016/0115483 A1 | 4/2016 | MacLachlan et al. |

FOREIGN PATENT DOCUMENTS

| | | |
|---|---|---|
| WO | 2004002453 A1 | 1/2004 |
| WO | 2007012191 A1 | 2/2007 |
| WO | 2007048046 A2 | 4/2007 |
| WO | 2007051303 A1 | 5/2007 |
| WO | 2009127060 A1 | 10/2009 |
| WO | 2011011447 A1 | 1/2011 |
| WO | 2011141705 A1 | 11/2011 |

OTHER PUBLICATIONS

Ahmed, et al., "Designing of highly effective complementary and mismatch siRNAs for silencing a gene", PloS One 6 (8), e23443 (2011).
Artusco, et al., "Inhibition of Junin virus replication by small interfering RNAs", Antiviral Res., 84(1), 31-37 (2009).
Caplen, et al., "Inhibition of viral gene expression and replication in mosquito cells by dsRNA-triggered RNA interference", Mol Ther 6, 243-251 (2002).
Daddario-Dicaprio, et al., "Postexposure protection against Marburg haemorrhagic fever with recombinant vesicular stomatitis virus vectors in non-human primates: an efficacy assessment", Lancet 367, 1399-1404 (2006).
Dye, et al., "Postexposure antibody prophylaxis protects nonhuman primates from filovirus disease", Proc Natl Acad Sci 109, 5034-5039 (2012).
Feldmann, et al., "Filoviridae: Marburg and Ebola Viruses.", Knipe DM, Howley PM, eds. Fields Virology, 6th ed., Lippincott Williams & Wilkins, 923-956 (2013).
Fowler, et al., "Inhibition of Marburg virus protein expression and viral release by RNA interference", J Gen Virol. 86 (Pt 4), 1181-1188 (2005).
Gavrilov, et al., "Therapeutic siRNA: principles, challenges, and strategies", Yale J Biol Med 85 (2), 187-200 (2012).
Geisbert, et al., "Exotic emerging viral diseases: progress and challenges", Nat Med 10 (12 Suppl), S110-S121 (2004).
Geisbert, et al., "Marburg virus Angola infection of rhesus macaques: pathogenesis and treatment with recombinant nematode anticoagulant protein c2", J Infect Dis 196 Suppl 2, S372-S381 (2007).
Geisbert, et al., "Postexposure protection of guinea pigs against a lethal ebola virus challenge is conferred by RNA interference", J Infect Dis 193 (12), 1650-1657 (2006).
Geisbert, et al., "Postexposure protection of non-human primates against a lethal Ebola virus challenge with RNA interference: a proof-of-concept study", Lancet 375(9729), 1896-1905 (2010).

(Continued)

*Primary Examiner* — Jane Zara
(74) *Attorney, Agent, or Firm* — Viksnins Harris Padys Malen LLP

(57) ABSTRACT

The present invention provides compositions comprising siRNA molecules that target Marburg virus (MARV) gene expression, lipid particles comprising one or more (e.g., a combination) of the siRNA molecules, and methods of delivering and/or administering the lipid particles, for the purposes of treating MARV infection.

21 Claims, 9 Drawing Sheets

(56) References Cited

OTHER PUBLICATIONS

Jeffs, et al., "A scalable, extrusion-free method for efficient liposomal encapsulation of plasmid DNA", Pharm Res 22 (3), 362-372 (2005).
Jones, et al., "Live attenuated recombinant vaccine protects non-human primates against Ebola and Marburg viruses", Nat Med 11, 786-790 (2005).
Judge, et al., "Confirming the RNAi-mediated mechanism of action of siRNA-based cancer therapeutics in mice", J Clin Invest 119, 661-673 (2009).
Judge, et al. "Sequence-dependent stimulation of the mammalian innate immune response by synthetic siRNA", Nat Biotechnol 23 (4), 457-462 (2005).
Muller, et al., "Broad-spectrum antiviral activity of small interfering RNA targeting the conserved RNA termini of Lassa virus", Antimicrob Agents Chemother 51 (6), 2215-2218 (2007).
Pacca, et al., "RNA interference inhibits yellow fever virus replication in vitro and in vivo", Virus Genes 38 (2), 224-231 (2009).
Robbins, et al., "siRNA and innate immunity", Oligonucleotides 19, 89-102 (2009).
Semple, et al., "Rational design of cationic lipids for siRNA delivery", Nat Biotechnol 28 (2), 172-176 (2010).
Thi, et al., "Marburg virus infection in nonhuman primates: Therapeutic treatment by lipid-encapsulated siRNA", Science Translational Medicine, vol. 6 (250), 250ra116, 20 pages (Aug. 20, 2014).
Towner, et al., "Marburgvirus genomics and association with a large hemorrhagic fever outbreak in Angola", J Virol 80, 6497-6516 (2006).
Ursic-Bedoya, et al., "Protection Against Lethal Marburg Virus Infection Mediated by Lipid Encapsulated Small Interfering RNA", Journal of Infectious Diseases 209, 562-570 (2014).
Warren, et al., "Advanced antisense therapies for postexposure protection against lethal filovirus infections", Nat Med 16, 991-994 (2010).

* cited by examiner

A. MARV-Angola

B. MARV-Ci67

C. MARV-Ravn

COMPOSITIONS AND METHODS FOR SILENCING MARBURG VIRUS GENE EXPRESSION

CROSS-REFERENCE TO RELATED APPLICATION(S)

This patent application claims the benefit of priority of U.S. application Ser. No. 62/040,339, filed Aug. 21, 2014, which application is herein incorporated by reference.

GOVERNMENT FUNDING

This invention was made with government support under AI089454 awarded by the US National Institute of Allergy and Infectious Diseases. The government has certain rights in the invention.

BACKGROUND OF THE INVENTION

Human viral hemorrhagic fevers are caused by four virus families all of which are enveloped RNA viruses (Geisbert T W, Jahrling P B. Exotic emerging viral diseases: progress and challenges. Nat Med 2004; 10:S110-21). Hemorrhagic fever caused by the filoviruses, Marburg virus (MARV) and Ebola virus (EBOV), exhibit the highest mortality rates ranging from 23-90% in humans (Feldmann et al., Filoviridae: Marburg and Ebola Viruses. In: Knipe D M, Howley P M, eds. Fields Virology. 6th ed. Philadelphia: Lippincott Williams & Wilkins, 2013:923-56). Filoviruses remain endemic to Central Africa and sporadic lethal outbreaks continue to occur. Despite the severity of disease caused by filoviruses, no licensed vaccine or therapeutic is currently available.

MARV possess a single-stranded RNA genome of approximately 19 kb encoding seven genes: NP (nucleoprotein), VP35 (polymerase cofactor), VP40 (matrix protein), GP (glycoprotein), VP30 (transcription activator), VP24 (secondary matrix protein), and a RNA-dependent RNA polymerase (L polymerase). Current therapeutic strategies consist of passive antibody therapy, which has demonstrated protection of nonhuman primates (NHP) against MARV-Ci67 using polyclonal NHP IgG (Dye et al. Postexposure antibody prophylaxis protects nonhuman primates from filovirus disease. Proc Natl Acad Sci USA 2012; 109:5034-9) and morpholino oligomers (PMOs), which protected NHPs against MARV-Musoke (Warren et al., Advanced antisense therapies for postexposure protection against lethal filovirus infections. Nat Med 2010; 16:991-4). These therapeutic strategies have not been shown to confer protection against MARV-Angola which causes higher mortality rates in man and a faster disease course in NHPs (Towner et al., Marburg virus genomics and association with a large hemorrhagic fever outbreak in Angola. J Virol 2006; 80:6497-516; Geisbert et al., Marburg virus Angola infection of rhesus macaques: pathogenesis and treatment with recombinant nematode anticoagulant protein c2. J Infect Dis 2007; 196 Suppl 2:S372-81).

Thus, there is a continuing need for compositions and methods for the treatment of Marburg Virus infection in humans, in particular treatment of infection with MARV-Angola.

SUMMARY OF THE INVENTION

As described more fully herein, one aspect the present invention provides isolated, double stranded, siRNA molecules, that each include a sense strand and an antisense strand that is hybridized to the sense strand. The siRNA of this aspect of the invention target one or more genes and/or transcripts of the MARV genome.

Accordingly, certain embodiments of the invention provide an isolated, double-stranded, siRNA molecule selected from the group consisting of Lpol-6801m (SEQ ID NO:13 and 14), VP40-320m (SEQ ID NO:15 and 16), VP24-518m (SEQ ID NO:17 and 18), VP24-734m (SEQ ID NO:19 and 20), NP-143m (SEQ ID NO:21 and 22) and NP-718m (SEQ ID NO:23 and 24).

The siRNA molecules of the invention are useful, for example, for the treatment of MARV infection when administered in a therapeutic amount to a human subject infected with MARV. More generally, the invention provides siRNA molecules that are capable of inhibiting or silencing MARV gene expression in vitro and in vivo.

In another aspect, the present invention provides isolated, single stranded, RNA molecules, consisting of a sequence selected from SEQ ID NO:13, SEQ ID NO:15, SEQ ID NO:17, SEQ ID NO:19, SEQ ID NO:21 and SEQ ID NO:23.

In another aspect, the present invention provides isolated, single stranded, RNA molecules, consisting of a sequence selected from SEQ ID NO:14, SEQ ID NO:16, SEQ ID NO:18, SEQ ID NO:20, SEQ ID NO:22 and SEQ ID NO:24.

The present invention also provides compositions, such as pharmaceutical compositions, that include one or more siRNA molecules of the invention (e.g., as described in Table B) (e.g., wherein the siRNA silences expression of a Marburg virus gene). In one embodiment, the present invention provides compositions that include two different siRNA molecules of the invention (e.g., two different siRNA molecules selected from the siRNA molecules disclosed in Table A and Table B herein). In one embodiments, the present invention provides a composition comprising two different double-stranded siRNAs selected from the group consisting of Lpol-6801m (SEQ ID NO:13 and 14), VP40-320m (SEQ ID NO:15 and 16), VP24-518m (SEQ ID NO:17 and 18), VP24-734m (SEQ ID NO:19 and 20), NP-143m (SEQ ID NO:21 and 22) and NP-718m (SEQ ID NO:23 and 24). In one embodiment, the present invention provides a composition comprising siRNA NP-718m and NP-143m. Thus, in one aspect, the present invention provides compositions (e.g., pharmaceutical compositions) that include one, two or more of the siRNAs set forth in Table B.

Certain embodiments of the invention provide a method for introducing an siRNA that silences expression of a Marburg virus gene into a cell, the method comprising the step of contacting the cell with a composition comprising one or more siRNA molecules described herein (e.g., as described in Table B) under conditions whereby the siRNA enters the cell and silences the expression of the Marburg virus gene within the cell. In certain embodiments, the cell is in a mammal, such as a human. In certain embodiments, the cell is contacted by administering the composition to the mammal via a systemic route. In certain embodiments, silencing of the Marburg virus gene expression reduces Marburg virus particle load in the mammal by at least about 50% relative to Marburg virus particle load in the absence of the composition.

Certain embodiments of the invention provide a method for ameliorating one or more symptoms associated with Marburg virus infection in a human, the method comprising the step of administering to the human a therapeutically effective amount of a composition of the invention described herein (e.g., a composition comprising one or more siRNA molecules described in Table B). In certain embodiments, the composition is administered via a systemic route. In certain embodiments, the siRNA of the composition inhibits expression of a Marburg virus gene in the human.

The present invention also provides lipid particles (e.g., nucleic acid-lipid particles), and formulations thereof, wherein the lipid particles each include one or more (e.g., a cocktail) of the siRNA described herein, a cationic lipid, and a non-cationic lipid, and optionally a conjugated lipid that inhibits aggregation of particles. Examples of siRNA molecules that can be included in the lipid particles of the invention are the siRNA molecules set forth in Table B, and combinations of the foregoing siRNA. For example, in certain embodiments, the nucleic acid-lipid particle comprises two different siRNA molecules selected from the group consisting of Lpol-6801m (SEQ ID NO:13 and 14), VP40-320m (SEQ ID NO:15 and 16), VP24-518m (SEQ ID NO:17 and 18), VP24-734m (SEQ ID NO:19 and 20), NP-143m (SEQ ID NO:21 and 22) and NP-718m (SEQ ID NO:23 and 24). In certain embodiments, the two different siRNA molecules are NP-143m (SEQ ID NO:21 and 22) and NP-718m (SEQ ID NO:23 and 24). Typically, the siRNA is fully encapsulated within the lipid particle. The lipid particles of the invention are useful, for example, for delivering a therapeutically effective amount of siRNA into cells of a human body infected with MARV, thereby treating the MARV infection and/or ameliorating one or more symptoms of MARV infection.

The present invention also provides a pharmaceutical composition comprising one or a cocktail of siRNA molecules that target MARV gene expression, and a pharmaceutically acceptable carrier. For example, the present invention provides pharmaceutical compositions that each include one, two or more of the siRNA molecules set forth in Table B that target MARV gene expression (e.g., NP-718m and NP-143m). With respect to formulations that include a cocktail of siRNAs encapsulated within lipid particles, the different siRNA molecules may be co-encapsulated in the same lipid particle, or each type of siRNA species present in the cocktail may be encapsulated in its own particle, or some siRNA species may be coencapsulated in the same particle while other siRNA species are encapsulated in different particles within the formulation. Typically, the interfering RNA molecules of the invention are fully encapsulated in the lipid particle.

The nucleic acid-lipid particles of the invention are useful for the prophylactic or therapeutic delivery, into a human infected with MARV, of siRNA molecules that silence the expression of one or more MARV genes, thereby ameliorating at least one symptom of MARV infection in the human. In some embodiments, one or more of the siRNA molecules described herein are formulated into nucleic acid-lipid particles, and the particles are administered to a mammal (e.g., a human) requiring such treatment. In certain instances, a therapeutically effective amount of the nucleic acid-lipid particle can be administered to the mammal, (e.g., for treating MARV infection in a human being). Administration of the nucleic acid-lipid particle can be by any route known in the art, such as, e.g., oral, intranasal, intravenous, intraperitoneal, intramuscular, intra-articular, intralesional, intratracheal, subcutaneous, or intradermal. In particular embodiments, the nucleic acid-lipid particle is administered systemically, e.g., via enteral or parenteral routes of administration.

In some embodiments, down regulation of MARV gene expression is determined by detecting MARV RNA or protein levels in a biological sample from a mammal after nucleic acid-lipid particle administration. In other embodiments, down regulation of MARV gene expression is determined by detecting MARV mRNA or protein levels in a biological sample from a mammal after nucleic acid-lipid particle administration. In certain embodiments, down regulation of MARV or MARV gene expression is detected by monitoring symptoms associated with MARV infection in a mammal after particle administration.

In another embodiment, the present invention provides methods for introducing an siRNA that silences MARV gene expression into a living cell, the method comprising the step of contacting the cell with a nucleic acid-lipid particle of the invention, wherein the nucleic acid-lipid particle includes an siRNA that targets MARV, under conditions whereby the siRNA enters the cell and silences the expression of a Marburg virus gene within the cell.

In another embodiment, the present invention provides a method for ameliorating one or more symptoms associated with Marburg virus infection in a human, the method including the step of administering to the human a therapeutically effective amount of a nucleic acid-lipid particle of the present invention. In some embodiments, the nucleic acid-lipid particles used in the methods of this aspect of the invention include one, two, or more different siRNA independently selected from the group of siRNAs set forth in Table B.

In another embodiment, the present invention provides methods for silencing MARV gene expression in a mammal (e.g., a human) in need thereof, wherein the methods each include the step of administering to the mammal a nucleic acid-lipid particle of the present invention.

In another aspect, the present invention provides methods for treating and/or ameliorating one or more symptoms associated with MARV infection in a human, wherein the methods each include the step of administering to the human a therapeutically effective amount of a nucleic acid-lipid particle of the present invention.

In another aspect, the present invention provides methods for inhibiting the expression of MARV in a mammal in need thereof (e.g., a human infected with MARV), wherein the methods each include the step of administering to the mammal a therapeutically effective amount of a nucleic acid-lipid particle of the present invention.

In a further aspect, the present invention provides methods for treating MARV infection in a human, wherein the methods each include the step of administering to the human a therapeutically effective amount of a nucleic acid-lipid particle of the present invention.

In a further aspect, the present invention provides for use of an siRNA molecule of the present invention for inhibiting Marburg virus gene expression in a living cell.

In a further aspect, the present invention provides for use of a pharmaceutical composition of the present invention for inhibiting Marburg virus gene expression in a living cell.

The compositions of the invention (e.g., siRNA molecules and isolated sense and antisense strands thereof, and nucleic acid-lipid particles) are also useful, for example, in biological assays (e.g., in vivo or in vitro assays) for inhibiting the expression of one or more MARV genes and/or transcripts to investigate MARV replication and biology, and/or to investigate or modulate the function of one or more MARV genes or transcripts. For example, the siRNA molecules of the invention can be screened using a biological assay to identify siRNA molecules that inhibit replication of MARV and that are candidate therapeutic agents for the treatment of MARV infection in humans, and/or the amelioration of at least one symptom associated with MARV infection in a human.

Other objects, features, and advantages of the present invention will be apparent to one of skill in the art from the following detailed description and figures.

BRIEF DESCRIPTION OF THE DRAWINGS

FIG. 2. 2'-O-methylated siRNAs targeting MARV genes retain activity in a dual luciferase reporter assay. HepG2 cells were reverse-transfected with plasmid containing the MARV target gene VP35, VP40, L polymerase, VP24, NP and 0.8-20 nM of the nucleic acid-lipid particles. Cells were lysed 48 h later for sequential measurement of *Renilla* luciferase (fused to the MARV target transgene) and Firefly luciferase signals. The *Renilla* luciferase signal was normalized to the Firefly luciferase signal and expressed as percentage gene expression relative to a plasmid-only control (pDNA) assigned a value of 100%. Lead native and 2'-O-methylated (designated 'm') siRNAs are compared. An siRNA against *Renilla* luciferase (Rluc) and an siRNA against ApoB were used as positive and negative controls, respectively. Data represents the mean (n=3) of experimental results±SD.

FIG. 3. 2'-O-methylated siRNA-lipid particle treatment of HepG2 cells results in the reduction of MARV virus titers in infected cells. HepG2 cells were treated with nucleic acid-lipid particles targeting individual viral mRNAs (A, VP35, B, VP40, L polymerase, VP24, and NP), Luc control lipid particles or left untreated and infected with MARV virus (Angola strain). Cell supernatants were harvested, serially diluted then plated on top of Vero76 cells. As a negative control, cells were left untreated or were treated with siRNA targeting luciferase (Luc-mod). Data represents the mean (n=3) of experimental results±SD.

FIG. 5. 2'-O-methylated siRNAs in lipid particles confer protection to guinea pigs against MARV-Angola challenge. A, Survival and B, plasma viraemia of Hartley strain guinea pigs after challenge with guinea pig adapted MARV-Angola. Animals (n=5 per group) were treated 1 h after viral challenge then treated daily for 6 additional consecutive days with lipid particles containing 0.5 mg/kg of each one of the siRNAs directed against the MARV L polymerase, VP24, VP40 or NP mRNAs. An siRNA against Luciferase (Luc-mod) was used as a negative control. Viraemia data from animal #4 in the Luc-mod group was not available. All other animals in the control group succumbed to viral infection before collection.

DETAILED DESCRIPTION OF THE INVENTION

Introduction

Figure 1:
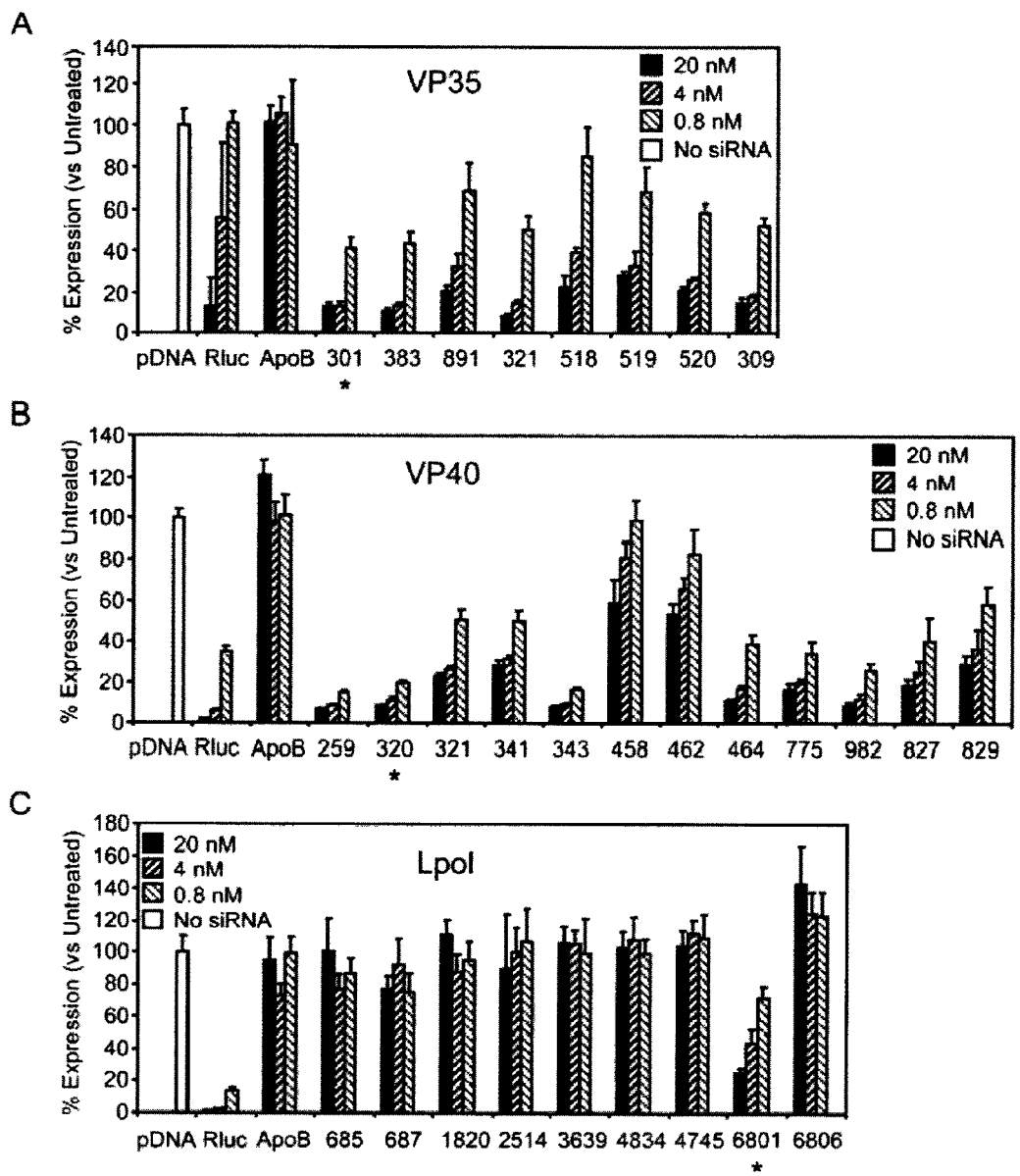
FIG. 1. siRNAs targeting MARV genes display activity in a dual luciferase reporter assay. HepG2 cells were reverse-transfected with plasmid containing the MARV target gene A, VP35, B, VP40, C, L polymerase, D, VP24, E, NP and 0.8-20 nM of the lipid particles containing siRNAs (numbered). Cells were lysed 48 h later for sequential measurement of *Renilla* luciferase (fused to MARV target transgene expression) and Firefly luciferase signals. The *Renilla* luciferase signal was normalized to the Firefly luciferase signal and expressed as percent gene expression relative to a plasmid-only control (pDNA) assigned a value of 100%. An siRNA against *Renilla* luciferase (Rluc) and an siRNA against ApoB were used as positive and negative controls, respectively. Asterisks denote lead siRNAs selected for further efficacy evaluation. Data represents the mean (n=3) of experimental results±SD.
Figure 1:
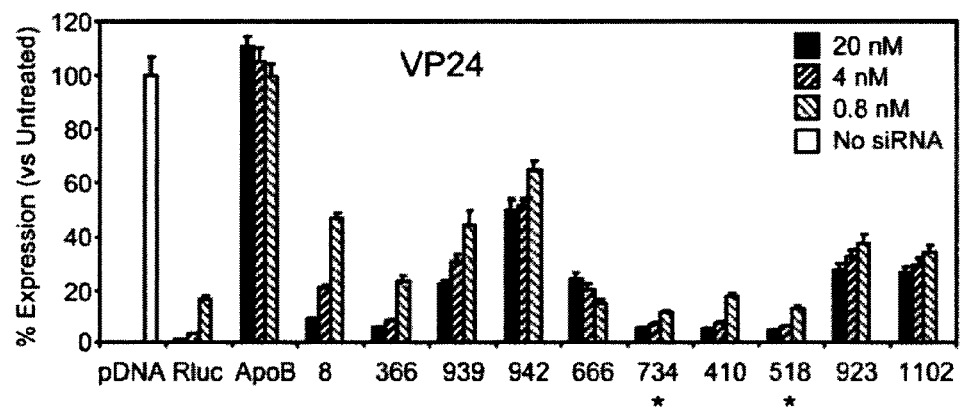
Figure 1:
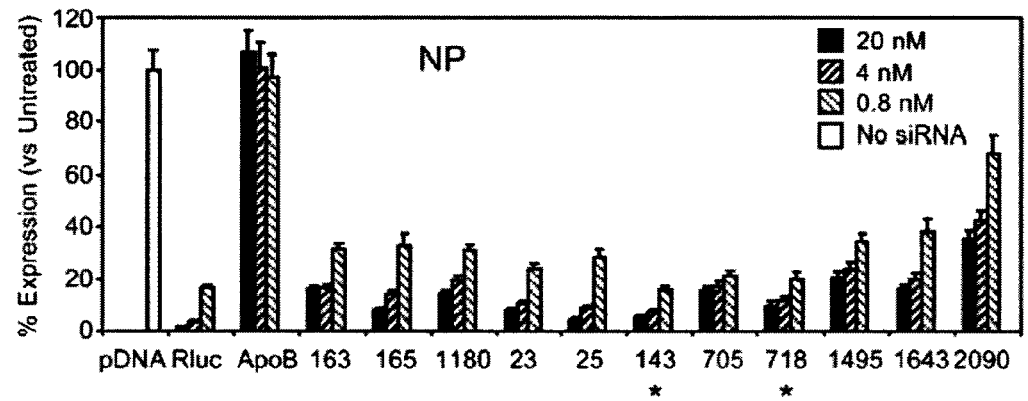

The interfering RNA (e.g., siRNA) drug therapy described herein advantageously provides significant new compositions and methods for treating MARV infection in human beings and the symptoms associated therewith. Embodiments of the present invention can be administered, for example, once per day, once per week, or once every several weeks (e.g., once every two, three, four, five or six weeks).

Furthermore, the nucleic acid-lipid particles described herein enable the effective delivery of a nucleic acid drug such as an siRNA into target tissues and cells within the body. The presence of the lipid particle confers protection from nuclease degradation in the bloodstream, allows preferential accumulation in target tissue and provides a means of drug entry into the cellular cytoplasm where the siRNAs can perform their intended function of RNA interference.

Definitions

As used herein, the following terms have the meanings ascribed to them unless specified otherwise.

The term "Marburg virus" (abbreviated as MARV) refers to a virus species that is a part of the filovirus family of viruses and is capable of causing hemorrhagic fever in humans. MARV possess a single-stranded RNA genome of approximately 19 kb encoding seven genes: NP (nucleoprotein), VP35 (polymerase cofactor), VP40 (matrix protein), GP (glycoprotein), VP30 (transcription activator), VP24 (secondary matrix protein), and a RNA-dependent RNA polymerase (L polymerase).

The term "interfering RNA" or "RNAi" or "interfering RNA sequence" as used herein includes single-stranded RNA (e.g., mature miRNA, ssRNAi oligonucleotides, ssD- NAi oligonucleotides) or double-stranded RNA (i.e., duplex RNA such as siRNA, Dicer-substrate dsRNA, shRNA, aiRNA, or pre-miRNA) that is capable of reducing or inhibiting the expression of a target gene or sequence (e.g., by mediating the degradation or inhibiting the translation of mRNAs which are complementary to the interfering RNA sequence) when the interfering RNA is in the same cell as the target gene or sequence. Interfering RNA thus refers to the single-stranded RNA that is complementary to a target mRNA sequence or to the double-stranded RNA formed by two complementary strands or by a single, self-complementary strand. Interfering RNA may have substantial or complete identity to the target gene or sequence, or may comprise a region of mismatch (i.e., a mismatch motif). The sequence of the interfering RNA can correspond to the full-length target gene, or a subsequence thereof. Preferably, the interfering RNA molecules are chemically synthesized.

Interfering RNA includes "small-interfering RNA" or "siRNA," e.g., interfering RNA of about 15-60, 15-50, or 15-40 (duplex) nucleotides in length, more typically about 15-30, 15-25, or 19-25 (duplex) nucleotides in length, and is preferably about 20-24, 21-22, or 21-23 (duplex) nucleotides in length (e.g., each complementary sequence of the double-stranded siRNA is 15-60, 15-50, 15-40, 15-30, 15-25, or 19-25 nucleotides in length, preferably about 20-24, 21-22, or 21-23 nucleotides in length, and the double-stranded siRNA is about 15-60, 15-50, 15-40, 15-30, 15-25, or 19-25 base pairs in length, preferably about 18-22, 19-20, or 19-21 base pairs in length). siRNA duplexes may comprise 3' overhangs of about 1 to about 4 nucleotides or about 2 to about 3 nucleotides and 5' phosphate termini. Examples of siRNA include, without limitation, a double-stranded polynucleotide molecule assembled from two separate stranded molecules, wherein one strand is the sense strand and the other is the complementary antisense strand; a double-stranded polynucleotide molecule assembled from a single stranded molecule, where the sense and antisense regions are linked by a nucleic acid-based or non-nucleic acid-based linker; a double-stranded polynucleotide molecule with a hairpin secondary structure having self-complementary sense and antisense regions; and a circular single-stranded polynucleotide molecule with two or more loop structures and a stem having self-complementary sense and antisense regions, where the circular polynucleotide can be processed in vivo or in vitro to generate an active double-stranded siRNA molecule.

Preferably, siRNA are chemically synthesized. siRNA can also be generated by cleavage of longer dsRNA (e.g., dsRNA greater than about 25 nucleotides in length) with the *E. coli* RNase III or Dicer. These enzymes process the dsRNA into biologically active siRNA (see, e.g., Yang et al., *Proc. Natl. Acad. Sci. USA*, 99:9942-9947 (2002); Calegari et al., *Proc. Natl. Acad. Sci. USA*, 99:14236 (2002); Byrom et al., *Ambion TechNotes*, 10(1):4-6 (2003); Kawasaki et al., *Nucleic Acids Res.*, 31:981-987 (2003); Knight et al., *Science*, 293:2269-2271 (2001); and Robertson et al., *J. Biol. Chem.*, 243:82 (1968)). Preferably, dsRNA are at least 50 nucleotides to about 100, 200, 300, 400, or 500 nucleotides in length. A dsRNA may be as long as 1000, 1500, 2000, 5000 nucleotides in length, or longer. The dsRNA can encode for an entire gene transcript or a partial gene transcript. In certain instances, siRNA may be encoded by a plasmid (e.g., transcribed as sequences that automatically fold into duplexes with hairpin loops).

The phrase "inhibiting expression of a target gene" refers to the ability of an interfering RNA (e.g., siRNA) of the invention to silence, reduce, or inhibit expression of a target gene (e.g., a gene within the MARV genome). To examine the extent of gene silencing, a test sample (e.g., a biological sample from an organism of interest expressing the target gene or a sample of cells in culture expressing the target gene) is contacted with an interfering RNA (e.g., siRNA) that silences, reduces, or inhibits expression of the target gene. Expression of the target gene in the test sample is compared to expression of the target gene in a control sample (e.g., a biological sample from an organism of interest expressing the target gene or a sample of cells in culture expressing the target gene) that is not contacted with the interfering RNA (e.g., siRNA). Control samples (e.g., samples expressing the target gene) may be assigned a value of 100%. In particular embodiments, silencing, inhibition, or reduction of expression of a target gene is achieved when the value of the test sample relative to the control sample (e.g., buffer only, an siRNA sequence that targets a different gene, a scrambled siRNA sequence, etc.) is about 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 70%, 65%, 60%, 55%, 50%, 45%, 40%, 35%, 30%, 25%, 20%, 15%, 10%, 5%, or 0%. Suitable assays include, without limitation, examination of protein or mRNA levels using techniques known to those of skill in the art, such as, e.g., dot blots, Northern blots, in situ hybridization, ELISA, immunoprecipitation, enzyme function, as well as phenotypic assays known to those of skill in the art.

An "effective amount" or "therapeutically effective amount" of a therapeutic nucleic acid such as an interfering RNA (e.g., siRNA) is an amount sufficient to produce the desired effect, e.g., an inhibition of expression of a target sequence in comparison to the normal expression level detected in the absence of an interfering RNA. In particular embodiments, inhibition of expression of a target gene or target sequence is achieved when the value obtained with an interfering RNA relative to the control (e.g., buffer only, an siRNA sequence that targets a different gene, a scrambled siRNA sequence, etc.) is about 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 70%, 65%, 60%, 55%, 50%, 45%, 40%, 35%, 30%, 25%, 20%, 15%, 10%, 5%, or 0%. Suitable assays for measuring the expression of a target gene or target sequence include, but are not limited to, examination of protein or mRNA levels using techniques known to those of skill in the art, such as, e.g., dot blots, Northern blots, in situ hybridization, ELISA, immunoprecipitation, enzyme function, as well as phenotypic assays known to those of skill in the art.

The term "nucleic acid" as used herein refers to a polymer containing at least two deoxyribonucleotides or ribonucleotides in either single- or double-stranded form and includes DNA and RNA. DNA may be in the form of, e.g., antisense molecules, plasmid DNA, precondensed DNA, a PCR product, vectors (P1, PAC, BAC, YAC, artificial chromosomes), expression cassettes, chimeric sequences, chromosomal DNA, or derivatives and combinations of these groups. RNA may be in the form, for example, of small interfering RNA (siRNA), Dicer-substrate dsRNA, small hairpin RNA (shRNA), asymmetrical interfering RNA (aiRNA), microRNA (miRNA), mRNA, tRNA, rRNA, tRNA, viral RNA (vRNA), and combinations thereof. Nucleic acids include nucleic acids containing known nucleotide analogs or modified backbone residues or linkages, which are synthetic, naturally occurring, and non-naturally occurring, and which have similar binding properties as the reference nucleic acid. Examples of such analogs include, without limitation, phosphorothioates, phosphoramidates, methyl phosphonates, chiral-methyl phosphonates, 2'-O-methyl ribonucleotides and peptide-nucleic acids (PNAs). Unless specifically limited, the term encompasses nucleic acids containing known analogues of natural nucleotides that have similar binding properties as the reference nucleic acid. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.*, 19:5081 (1991); Ohtsuka et al., *J. Biol. Chem.*, 260:2605-2608 (1985); Rossolini et al., *Mol. Cell. Probes*, 8:91-98 (1994)). "Nucleotides" contain a sugar deoxyribose (DNA) or ribose (RNA), a base, and a phosphate group. Nucleotides are linked together through the phosphate groups. "Bases" include purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylates, and alkylhalides.

The term "gene" refers to a nucleic acid (e.g., DNA or RNA) sequence that comprises partial length or entire length coding sequences necessary for the production of a polypeptide or precursor polypeptide.

"Gene product," as used herein, refers to a product of a gene such as an RNA transcript or a polypeptide.

The term "lipid" refers to a group of organic compounds that include, but are not limited to, esters of fatty acids and are characterized by being insoluble in water, but soluble in many organic solvents. They are usually divided into at least three classes: (1) "simple lipids," which include fats and oils as well as waxes; (2) "compound lipids," which include phospholipids and glycolipids; and (3) "derived lipids" such as steroids.

The term "lipid particle" includes a lipid formulation that can be used to deliver a therapeutic nucleic acid (e.g., siRNA) to a target site of interest (e.g., cell, tissue, organ, and the like). In preferred embodiments, the lipid particle of the invention is typically formed from a cationic lipid, a non-cationic lipid, and optionally a conjugated lipid that prevents aggregation of the particle. A lipid particle that includes a nucleic acid molecule (e.g., siRNA molecule) is referred to as a nucleic acid-lipid particle. Typically, the nucleic acid is fully encapsulated within the lipid particle, thereby protecting the nucleic acid from enzymatic degradation.

In certain instances, nucleic acid-lipid particles are extremely useful for systemic applications, as they can exhibit extended circulation lifetimes following intravenous (i.v.) injection, they can accumulate at distal sites (e.g., sites physically separated from the administration site), and they can mediate silencing of target gene expression at these distal sites. The nucleic acid may be complexed with a condensing agent and encapsulated within a lipid particle as set forth in PCT Publication No. WO 00/03683, the disclosure of which is herein incorporated by reference in its entirety for all purposes.

The lipid particles of the invention typically have a mean diameter of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm, and are substantially non-toxic. In addition, nucleic acids, when present in the lipid particles of the present invention, are resistant in aqueous solution to degradation with a nuclease. Nucleic acid-lipid particles and their method of preparation are disclosed in, e.g., U.S. Patent Publication Nos. 20040142025 and 20070042031, the disclosures of which are herein incorporated by reference in their entirety for all purposes.

As used herein, "lipid encapsulated" can refer to a lipid particle that provides a therapeutic nucleic acid such as an interfering RNA (e.g., siRNA), with full encapsulation, partial encapsulation, or both. In a preferred embodiment, the nucleic acid (e.g., interfering RNA) is fully encapsulated in the lipid particle (e.g., to form a nucleic acid-lipid particle).

The term "lipid conjugate" refers to a conjugated lipid that inhibits aggregation of lipid particles. Such lipid conjugates include, but are not limited to, PEG-lipid conjugates such as, e.g., PEG coupled to dialkyloxypropyls (e.g., PEG-DAA conjugates), PEG coupled to diacylglycerols (e.g., PEG-DAG conjugates), PEG coupled to cholesterol, PEG coupled to phosphatidylethanolamines, and PEG conjugated to ceramides (see, e.g., U.S. Pat. No. 5,885,613), cationic PEG lipids, polyoxazoline (POZ)-lipid conjugates (e.g., POZ-DAA conjugates), polyamide oligomers (e.g., ATTA-lipid conjugates), and mixtures thereof. Additional examples of POZ-lipid conjugates are described in PCT Publication No. WO 2010/006282. PEG or POZ can be conjugated directly to the lipid or may be linked to the lipid via a linker moiety. Any linker moiety suitable for coupling the PEG or the POZ to a lipid can be used including, e.g., non-ester containing linker moieties and ester-containing linker moieties. In certain preferred embodiments, non-ester containing linker moieties, such as amides or carbamates, are used.

The term "amphipathic lipid" refers, in part, to any suitable material wherein the hydrophobic portion of the lipid material orients into a hydrophobic phase, while the hydrophilic portion orients toward the aqueous phase. Hydrophilic characteristics derive from the presence of polar or charged groups such as carbohydrates, phosphate, carboxylic, sulfato, amino, sulfhydryl, nitro, hydroxyl, and other like groups. Hydrophobicity can be conferred by the inclusion of apolar groups that include, but are not limited to, long-chain saturated and unsaturated aliphatic hydrocarbon groups and such groups substituted by one or more aromatic, cycloaliphatic, or heterocyclic group(s). Examples of amphipathic compounds include, but are not limited to, phospholipids, aminolipids, and sphingolipids.

Representative examples of phospholipids include, but are not limited to, phosphatidylcholine, phosphatidylethanolamine, phosphatidylserine, phosphatidylinositol, phosphatidic acid, palmitoyloleoyl phosphatidylcholine, lyso-phosphatidylcholine, lysophosphatidylethanolamine, dipalmitoylphosphatidylcholine, dioleoylphosphatidylcholine, distearoylphosphatidylcholine, and dilinoleoylphosphatidylcholine. Other compounds lacking in phosphorus, such as sphingolipid, glycosphingolipid families, diacylglycerols, and β-acyloxyacids, are also within the group designated as amphipathic lipids. Additionally, the amphipathic lipids described above can be mixed with other lipids including triglycerides and sterols.

The term "neutral lipid" refers to any of a number of lipid species that exist either in an uncharged or neutral zwitterionic form at a selected pH. At physiological pH, such lipids include, for example, diacylphosphatidylcholine, diacylphosphatidylethanolamine, ceramide, sphingomyelin, cephalin, cholesterol, cerebrosides, and diacylglycerols.

The term "non-cationic lipid" refers to any amphipathic lipid as well as any other neutral lipid or anionic lipid.

The term "anionic lipid" refers to any lipid that is negatively charged at physiological pH. These lipids include, but are not limited to, phosphatidylglycerols, cardiolipins, diacylphosphatidylserines, diacylphosphatidic acids, N-dodecanoyl phosphatidylethanolamines, N-succinyl phosphatidylethanolamines, N-glutarylphosphatidylethanolamines, lysylphosphatidylglycerols, palmitoyloleyolphosphatidylglycerol (POPG), and other anionic modifying groups joined to neutral lipids.

The term "hydrophobic lipid" refers to compounds having apolar groups that include, but are not limited to, long-chain saturated and unsaturated aliphatic hydrocarbon groups and such groups optionally substituted by one or more aromatic, cycloaliphatic, or heterocyclic group(s). Suitable examples include, but are not limited to, diacylglycerol, dialkylglycerol, N—N-dialkylamino, 1,2-diacyloxy-3-aminopropane, and 1,2-dialkyl-3-aminopropane.

The terms "cationic lipid" and "amino lipid" are used interchangeably herein to include those lipids and salts thereof having one, two, three, or more fatty acid or fatty alkyl chains and a pH-titratable amino head group (e.g., an alkylamino or dialkylamino head group). The cationic lipid is typically protonated (i.e., positively charged) at a pH below the $pK_a$ of the cationic lipid and is substantially neutral at a pH above the $pK_a$. The cationic lipids of the invention may also be termed titratable cationic lipids. In some embodiments, the cationic lipids comprise: a protonatable tertiary amine (e.g., pH-titratable) head group; $C_{18}$ alkyl chains, wherein each alkyl chain independently has 0 to 3 (e.g., 0, 1, 2, or 3) double bonds; and ether, ester, or ketal linkages between the head group and alkyl chains. Such cationic lipids include, but are not limited to, DSDMA, DODMA, DLinDMA, DLenDMA, γ-DLenDMA, DLin-K-DMA, DLin-K-C2-DMA (also known as DLin-C2K-DMA, XTC2, and C2K), DLin-K-C3-DMA, DLin-K-C4-DMA, DLen-C2K-DMA, γ-DLen-C2K-DMA, DLin-M-C2-DMA (also known as MC2), and DLin-M-C3-DMA (also known as MC3).

The term "salts" includes any anionic and cationic complex, such as the complex formed between a cationic lipid and one or more anions. Non-limiting examples of anions include inorganic and organic anions, e.g., hydride, fluoride, chloride, bromide, iodide, oxalate (e.g., hemioxalate), phosphate, phosphonate, hydrogen phosphate, dihydrogen phosphate, oxide, carbonate, bicarbonate, nitrate, nitrite, nitride, bisulfite, sulfide, sulfite, bisulfate, sulfate, thiosulfate, hydrogen sulfate, borate, formate, acetate, benzoate, citrate, tartrate, lactate, acrylate, polyacrylate, fumarate, maleate, itaconate, glycolate, gluconate, malate, mandelate, tiglate, ascorbate, salicylate, polymethacrylate, perchlorate, chlorate, chlorite, hypochlorite, bromate, hypobromite, iodate, an alkylsulfonate, an arylsulfonate, arsenate, arsenite, chromate, dichromate, cyanide, cyanate, thiocyanate, hydroxide, peroxide, permanganate, and mixtures thereof. In particular embodiments, the salts of the cationic lipids disclosed herein are crystalline salts.

The term "alkyl" includes a straight chain or branched, noncyclic or cyclic, saturated aliphatic hydrocarbon containing from 1 to 24 carbon atoms. Representative saturated straight chain alkyls include, but are not limited to, methyl, ethyl, n-propyl, n-butyl, n-pentyl, n-hexyl, and the like, while saturated branched alkyls include, without limitation, isopropyl, sec-butyl, isobutyl, tert-butyl, isopentyl, and the like. Representative saturated cyclic alkyls include, but are not limited to, cyclopropyl, cyclobutyl, cyclopentyl, cyclohexyl, and the like, while unsaturated cyclic alkyls include, without limitation, cyclopentenyl, cyclohexenyl, and the like.

The term "alkenyl" includes an alkyl, as defined above, containing at least one double bond between adjacent carbon atoms. Alkenyls include both cis and trans isomers. Representative straight chain and branched alkenyls include, but are not limited to, ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like.

The term "alkynyl" includes any alkyl or alkenyl, as defined above, which additionally contains at least one triple bond between adjacent carbons. Representative straight chain and branched alkynyls include, without limitation, acetylenyl, propynyl, 1-butynyl, 2-butynyl, 1-pentynyl, 2-pentynyl, 3-methyl-1 butynyl, and the like.

The term "acyl" includes any alkyl, alkenyl, or alkynyl wherein the carbon at the point of attachment is substituted with an oxo group, as defined below. The following are non-limiting examples of acyl groups: —C(=O)alkyl, —C(=O)alkenyl, and —C(=O)alkynyl.

The term "heterocycle" includes a 5- to 7-membered monocyclic, or 7- to 10-membered bicyclic, heterocyclic ring which is either saturated, unsaturated, or aromatic, and which contains from 1 or 2 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include, but are not limited to, heteroaryls as defined below, as well as morpholinyl, pyrrolidinonyl, pyrrolidinyl, piperidinyl, piperizynyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The terms "optionally substituted alkyl", "optionally substituted alkenyl", "optionally substituted alkynyl", "optionally substituted acyl", and "optionally substituted heterocycle" mean that, when substituted, at least one hydrogen atom is replaced with a substituent. In the case of an oxo substituent (=O), two hydrogen atoms are replaced. In this regard, substituents include, but are not limited to, oxo, halogen, heterocycle, —CN, —OR$^x$, —NR$^x$R$^y$, —NR$^x$(=O)R$^y$, —NR$^x$SO$_2$R$^y$, —C(=O)R$^x$, —C(=O)OR$^x$, —C(=O)NR$^x$R$^y$, —SO—R$^x$, and —SO$_n$NR$^x$R$^y$, wherein n is 0, 1, or 2, R$^x$ and R$^y$ are the same or different and are independently hydrogen, alkyl, or heterocycle, and each of the alkyl and heterocycle substituents may be further substituted with one or more of oxo, halogen, —OH, —CN, alkyl, —OR$^x$, heterocycle, —NR$^x$R$^y$, —NR$^x$C(═O)R$^y$, —NR$^x$SO$_2$R$^y$, —C(═O)R$^x$, —C(═O)OR$^x$, —C(═O) NR$^x$R$^y$, —SO$_n$R$^x$, and —SO$_n$NR$^x$R$^y$. The term "optionally substituted," when used before a list of substituents, means that each of the substituents in the list may be optionally substituted as described herein.

The term "halogen" includes fluoro, chloro, bromo, and iodo.

The term "fusogenic" refers to the ability of a lipid particle to fuse with the membranes of a cell. The membranes can be either the plasma membrane or membranes surrounding organelles, e.g., endosome, nucleus, etc.

As used herein, the term "aqueous solution" refers to a composition comprising in whole, or in part, water.

As used herein, the term "organic lipid solution" refers to a composition comprising in whole, or in part, an organic solvent having a lipid.

"Distal site," as used herein, refers to a physically separated site, which is not limited to an adjacent capillary bed, but includes sites broadly distributed throughout an organism.

"Serum-stable" in relation to nucleic acid-lipid particles means that the particle is not significantly degraded after exposure to a serum or nuclease assay that would significantly degrade free DNA or RNA. Suitable assays include, for example, a standard serum assay, a DNAse assay, or an RNAse assay.

"Systemic delivery," as used herein, refers to delivery of lipid particles that leads to a broad biodistribution of an active agent such as an interfering RNA (e.g., siRNA) within an organism. Some techniques of administration can lead to the systemic delivery of certain agents, but not others. Systemic delivery means that a useful, preferably therapeutic, amount of an agent is exposed to most parts of the body. To obtain broad biodistribution generally requires a blood lifetime such that the agent is not rapidly degraded or cleared (such as by first pass organs (liver, lung, etc.) or by rapid, nonspecific cell binding) before reaching a disease site distal to the site of administration. Systemic delivery of lipid particles can be by any means known in the art including, for example, intravenous, subcutaneous, and intraperitoneal. In a preferred embodiment, systemic delivery of lipid particles is by intravenous delivery.

"Local delivery," as used herein, refers to delivery of an active agent such as an interfering RNA (e.g., siRNA) directly to a target site within an organism. For example, an agent can be locally delivered by direct injection into a disease site, other target site, or a target organ such as the liver, heart, pancreas, kidney, and the like.

The term "mammal" refers to any mammalian species such as a human, mouse, rat, dog, cat, hamster, guinea pig, rabbit, livestock, and the like.

DESCRIPTION OF THE EMBODIMENTS

The present invention provides siRNA molecules that target the expression of one or more MARV genes, nucleic acid-lipid particles comprising one or more (e.g., a cocktail) of the siRNAs, and methods of delivering and/or administering the nucleic acid-lipid particles (e.g., for the treatment of MARV infection in humans).

In one aspect, the present invention provides siRNA molecules that target expression of one or more MARV genes. In certain instances, the present invention provides compositions comprising a combination (e.g., a cocktail, pool, or mixture) of siRNAs that target different regions of the MARV genome. In certain instances, the siRNA molecules of the invention are capable of inhibiting the replication of MARV in vitro or in vivo.

In particular embodiments, the present invention provides the siRNA molecules shown in Tables A and B, wherein the top strand of each double-stranded siRNA molecule is the sense strand running in a 5' to 3' direction from left to right; and the lower strand of each double-stranded siRNA molecule is the antisense strand running in a 5' to 3' direction from right to left. In certain embodiments, the siRNA molecules may comprise ribonucleotides with a 2'-O-methyl modification, as shown in Table B.

TABLE A

| Name | Duplex | Antisense Complementarity to MARV |
|------|--------|-----------------------------------|
| Lpol-6801 | 5' CGUCAAGGCAAACAACAUUUA 3' (SEQ ID NO: 1) 3' AAGCAGUUCCGUUUGUUGUAA 5' (SEQ ID NO: 2) | Angola, Ci67 and Musoke |
| VP40-320 | 5' GUCUGCCAUGCUUUCACUUUA 3' (SEQ ID NO: 3) 3' UACAGACGGUACGAAAGUGAA 5' (SEQ ID NO: 4) | Angola, Ci67 and Musoke |
| VP24-518 | 5' CCAAGAAUUACAGCAAUCAUU 3' (SEQ ID NO: 5) 3' CUGGUUCUUAAUGUCGUUAGU 5' (SEQ ID NO: 6) | Angola, Ci67 and Musoke |
| VP24-734 | 5' CCAGCAGUAUUGAAAUAAAGU 3' (SEQ ID NO: 7) 3' UGGGUCGUCAUAACUUUAUUU 5' (SEQ ID NO: 8) | Angola, Ci67, Musoke and Ravn |
| NP-143 | 5' UCAGGUUAGUAUCUGUAAUCA 3' (SEQ ID NO: 9) 3' GUAGUCCAAUCAUAGACAUUA 5' (SEQ ID NO: 10) | Angola, Ci67, Musoke and Ravn |
| NP-718 | 5' GAUUCUCAGGACUUCUUAUUG 3' (SEQ ID NO: 11) 3' AUCUAAGAGUCCUGAAGAAUA 5' (SEQ ID NO: 12) | Angola, Ci67 and Musoke |

TABLE B

| Name | Duplex | Antisense Complementarity to MARV |
|------|--------|-----------------------------------|
| Lpol-6801m | 5' CGUCAAGGCAAACAACAUUUA 3' (SEQ ID NO: 13) 3' AAGCAGUUCCGUUUGUUGUAA 5' (SEQ ID NO: 14) | Angola, Ci67 and Musoke |
| VP40-320m | 5' GUCUGCCAUGCUUUCACUUUA 3' (SEQ ID NO: 15) 3' UACAGACGGUACGAAAGUGAA 5' (SEQ ID NO: 16) | Angola, Ci67 and Musoke |
| VP24-518m | 5' CCAAGAAUUACAGCAAUCAUU 3' (SEQ ID NO: 17) 3' CUGGUUCUUAAUGUCGUUAGU 5' (SEQ ID NO: 18) | Angola, Ci67 and Musoke |
| VP24-734m | 5' CCAGCAGUAUUGAAAUAAAGU 3' (SEQ ID NO: 19) 3' UGGGUCGUCAUAACUUUAUUU 5' (SEQ ID NO: 20) | Angola, Ci67, Musoke and Ravn |

TABLE B-continued

| Name | Duplex | Antisense Complementarity to MARV |
|---|---|---|
| NP-143m | 5' UCAGGUUAGUAUCUGUAAUCA 3' (SEQ ID NO: 21)<br>3' GUAGUCCAAUCAUAGACAUUA 5' (SEQ ID NO: 22) | Angola, Ci67, Musoke and Ravn |
| NP-718m | 5' GAUUCUCAGGACUUCUUAUUG 3' (SEQ ID NO: 23)<br>3' AUCUAAGAGUCCUGAAGAAUA 5' (SEQ ID NO: 24) | Angola, Ci67 and Musoke |

*Underlining denotes the presence of a 2'-O-methyl modification at the particular underlined ribo-nucleotide.

In other embodiments, as set forth in Table C and Table D herein, the present invention provides the isolated sense strands and antisense strands (i.e., isolated single stranded nucleic acid molecules) of the siRNA molecules set forth in Tables A and B, respectively. The nucleic acid sequences set forth in Table C and Table D are arranged as pairs of sequences, wherein each pair includes a sense strand and its complementary antisense strand. Each pair of sequences (sense plus antisense strand) is identified with a particular name, which correspond to the names shown in Tables A and B.

These isolated sense and antisense strands, shown in Table C and Table D, are useful, for example, for making siRNA molecules that are useful to reduce the expression of one or more MARV genes in vivo or in vitro. These isolated sense and antisense strands are also useful, for example, as hybridization probes for identifying and measuring the amount of MARV genome in a biological material, such as a tissue or blood sample from a human being infected with MARV.

TABLE C

| Name | Sense Strand (5' to 3') | Antisense Strand (5' to 3') |
|---|---|---|
| Lpol-6801 | CGUCAAGGCAAACAACAUUUA (SEQ ID NO: 1) | AAUGUUGUUUGCCUUGACGAA (SEQ ID NO: 2) |
| VP40-320 | GUCUGCCAUGCUUUCACUUUA (SEQ ID NO: 3) | AAGUGAAAGCAUGGCAGACAU (SEQ ID NO: 4) |
| VP24-518 | CCAAGAAUUACAGCAAUCAUU (SEQ ID NO: 5) | UGAUUGCUGUAAUUCUUGGUC (SEQ ID NO: 6) |
| VP24-734 | CCAGCAGUAUUGAAAUAAAGU (SEQ ID NO: 7) | UUUAUUUCAAUACUGCUGGGU (SEQ ID NO: 8) |
| NP-143 | UCAGGUUAGUAUCUGUAAUCA (SEQ ID NO: 9) | AUUACAGAUACUAACCUGAUG (SEQ ID NO: 10) |
| NP-718 | GAUUCUCAGGACUUCUUAUUG (SEQ ID NO: 11) | AUAAGAAGUCCUGAGAAUCUA (SEQ ID NO: 12) |

TABLE D

| Name | Sense Strand (5' to 3') | Antisense Strand (5' to 3') |
|---|---|---|
| Lpol-6801m | CGUCAAGGCAAACAACAUUUA (SEQ ID NO: 13) | AAUGUUGUUUGCCUUGACGAA (SEQ ID NO: 14) |

TABLE D -continued

| Name | Sense Strand (5' to 3') | Antisense Strand (5' to 3') |
|---|---|---|
| VP40-320m | GUCUGCCAUGCUUUCACUUUA (SEQ ID NO: 15) | AAGUGAAAGCAUGGCAGACAU (SEQ ID NO: 16) |
| VP24-518m | CCAAGAAUUACAGCAAUCAUU (SEQ ID NO: 17) | UGAUUGCUGUAAUUCUUGGUC (SEQ ID NO: 18) |
| VP24-734m | CCAGCAGUAUUGAAAUAAAGU (SEQ ID NO: 19) | UUUAUUUCAAUACUGCUGGGU (SEQ ID NO: 20) |
| NP-143m | UCAGGUUAGUAUCUGUAAUCA (SEQ ID NO: 21) | AUUACAGAUACUAACCUGAUG (SEQ ID NO: 22) |
| NP-718m | GAUUCUCAGGACUUCUUAUUG (SEQ ID NO: 23) | AUAAGAAGUCCUGAGAAUCUA (SEQ ID NO: 24) |

*Underlining denotes the presence of a 2'-O-methyl modification at the particular underlined ribo-nucleotide.

Thus, certain embodiments of the invention provide an isolated, double-stranded, siRNA molecule selected from the group consisting of Lpol-6801m (SEQ ID NO:13 and 14), VP40-320m (SEQ ID NO:15 and 16), VP24-518m (SEQ ID NO:17 and 18), VP24-734m (SEQ ID NO:19 and 20), NP-143m (SEQ ID NO:21 and 22) and NP-718m (SEQ ID NO:23 and 24). In certain embodiments, the isolated, double-stranded, siRNA molecule is NP-143m (SEQ ID NO:21 and 22). In certain embodiment, the isolated, double-stranded, siRNA molecule is NP-718m (SEQ ID NO:23 and 24).

Certain embodiments of the invention also provide an isolated, sense, single-stranded, RNA molecule consisting of a sequence selected from SEQ ID NO:13, SEQ ID NO:15, SEQ ID NO:17, SEQ ID NO:19, SEQ ID NO:21 and SEQ ID NO:23. In certain embodiments, the sequence is SEQ ID NO:21. In certain embodiments, the sequence is SEQ ID NO:23. Certain embodiments of the invention also provide an isolated, antisense, single-stranded, RNA molecule consisting of a sequence selected from SEQ ID NO:14, SEQ ID NO:16, SEQ ID NO:18, SEQ ID NO:20, SEQ ID NO:22 and SEQ ID NO:24. In certain embodiments, the sequence is SEQ ID NO:22. In certain embodiments, the sequence is SEQ ID NO:24.

The present invention also provides a pharmaceutical composition comprising one or more (e.g., a cocktail) of the siRNAs described herein and a pharmaceutically acceptable carrier.

In another aspect, the present invention provides a nucleic acid-lipid particle that targets MARV gene expression. The nucleic acid-lipid particles typically comprise one or more (e.g., a cocktail) of the isolated, double-stranded siRNA molecules described herein (e.g., as described in Table B), a cationic lipid, and a non-cationic lipid. In certain instances, the nucleic acid-lipid particles further comprise a conjugated lipid that inhibits aggregation of particles. Preferably, the nucleic acid-lipid particles comprise one or more (e.g., a cocktail) of the isolated, double-stranded siRNA molecules described herein, a cationic lipid, a non-cationic lipid, and a conjugated lipid that inhibits aggregation of particles.

In some embodiments, the siRNAs of the present invention are fully encapsulated in the nucleic acid-lipid particle. With respect to formulations comprising an siRNA cocktail, the different types of siRNA species present in the cocktail (e.g., siRNA compounds with different sequences) may be co-encapsulated in the same particle, or each type of siRNA species present in the cocktail may be encapsulated in a separate particle. The siRNA cocktail may be formulated in the particles described herein using a mixture of two or more individual interfering RNAs (each having a unique sequence) at identical, similar, or different concentrations or molar ratios. In one embodiment, a cocktail of siRNAs (corresponding to a plurality of siRNAs with different sequences) is formulated using identical, similar, or different concentrations or molar ratios of each siRNA species, and the different types of siRNAs are co-encapsulated in the same particle. In another embodiment, each type of siRNA species present in the cocktail is encapsulated in different particles at identical, similar, or different siRNA concentrations or molar ratios, and the particles thus formed (each containing a different siRNA payload) are administered separately (e.g., at different times in accordance with a therapeutic regimen), or are combined and administered together as a single unit dose (e.g., with a pharmaceutically acceptable carrier). The particles described herein are serum-stable, are resistant to nuclease degradation, and are substantially non-toxic to mammals such as humans.

The cationic lipid in the nucleic acid-lipid particles of the invention may comprise, e.g., one or more cationic lipids of Formula I-III described herein or any other cationic lipid species. In one particular embodiment, the cationic lipid is selected from the group consisting of 1,2-dilinoleyloxy-N,N-dimethylaminopropane (DLinDMA), 1,2-dilinolenyloxy-N,N-dimethylaminopropane (DLenDMA), 1,2-di-γ-linolenyloxy-N,N-dimethylaminopropane (γ-DLenDMA), 2,2-dilinoleyl-4-(2-dimethylaminoethyl)[1,3]-dioxolane (DLin-K-C2-DMA), 2,2-dilinoleyl-4-dimethylaminomethyl-[1,3]-dioxolane (DLin-K-DMA), dilinoleylmethyl-3-dimethylaminopropionate (DLin-M-C2-DMA), (6Z,9Z,28Z,31Z)-heptatriaconta-6,9,28,31-tetraen-19-yl 4-(dimethylamino)butanoate (DLin-M-C3-DMA), salts thereof, and mixtures thereof.

In another particular embodiment, the cationic lipid is selected from the group consisting of 1,2-dilinoleyloxy-N,N-dimethylaminopropane (DLinDMA), 1,2-dilinolenyloxy-N,N-dimethylaminopropane (DLenDMA), 1,2-di-γ-linolenyloxy-N,N-dimethylaminopropane (γ-DLenDMA), 3-((6Z,9Z,28Z,31Z)-heptatriaconta-6,9,28,31-tetraen-19-yloxy)-N,N-dimethylpropan-1-amine (DLin-MP-DMA), MC3 ((6Z,9Z,28Z,31Z)-heptatriaconta-6,9,28,31-tetraen-19-yl 4-(dimethylamino) butanoate), (6Z,16Z)-12-((Z)-dec-4-enyl)docosa-6,16-dien-11-yl 5-(dimethylamino)pentanoate a salt thereof, or a mixture thereof.

In certain embodiments, the cationic lipid comprises from about 50 mol % to about 65 mol % of the total lipid present in the particle.

The non-cationic lipid in the nucleic acid-lipid particles of the present invention may comprise, e.g., one or more anionic lipids and/or neutral lipids. In some embodiments, the non-cationic lipid comprises one of the following neutral lipid components: (1) a mixture of a phospholipid and cholesterol or a derivative thereof; (2) cholesterol or a derivative thereof, or (3) a phospholipid. In certain preferred embodiments, the phospholipid comprises dipalmitoylphosphatidylcholine (DPPC), distearoylphosphatidylcholine (DSPC), or a mixture thereof. In a particularly preferred embodiment, the non-cationic lipid is a mixture of DPPC and cholesterol.

In certain embodiments, the non-cationic lipid comprises a mixture of a phospholipid and cholesterol or a derivative thereof, wherein the phospholipid comprises from about 4 mol % to about 11 mol % of the total lipid present in the particle and the cholesterol or derivative thereof comprises from about 30 mol % to about 40 mol % of the total lipid present in the particle. In certain embodiments, the phospholipid comprises from about 5 mol % to about 10 mol % of the total lipid present in the particle and the cholesterol or derivative thereof comprises from about 32 mol % to about 37 mol % of the total lipid present in the particle.

The lipid conjugate in the nucleic acid-lipid particles of the invention inhibits aggregation of particles and may comprise, e.g., one or more of the lipid conjugates described herein. In one particular embodiment, the lipid conjugate comprises a PEG-lipid conjugate. Examples of PEG-lipid conjugates include, but are not limited to, PEG-DAG conjugates, PEG-DAA conjugates, and mixtures thereof. In certain embodiments, the PEG-lipid conjugate is selected from the group consisting of a PEG-diacylglycerol (PEG-DAG) conjugate, a PEG-dialkyloxypropyl (PEG-DAA) conjugate, a PEG-phospholipid conjugate, a PEG-ceramide (PEG-Cer) conjugate, and a mixture thereof. In certain embodiments, the PEG-lipid conjugate is a PEG-DAA conjugate. In certain embodiments, the PEG-DAA conjugate in the lipid particle may comprise a PEG-didecyloxypropyl ($C_{10}$) conjugate, a PEG-dilauryloxypropyl ($C_{12}$) conjugate, a PEG-dimyristyloxypropyl ($C_{14}$) conjugate, a PEG-dipalmityloxypropyl ($C_{16}$) conjugate, a PEG-distearyloxypropyl ($C_{18}$) conjugate, or mixtures thereof. In another embodiment, the lipid conjugate comprises a POZ-lipid conjugate such as a POZ-DAA conjugate.

In certain embodiments, the conjugated lipid that inhibits aggregation of particles comprises from about 0.5 mol % to about 2 mol % of the total lipid present in the particle.

In some embodiments, the present invention provides nucleic acid-lipid particles comprising: (a) one or more (e.g., a cocktail) siRNA molecules described herein (e.g., see, Table B); (b) one or more cationic lipids or salts thereof comprising from about 50 mol % to about 85 mol % of the total lipid present in the particle; (c) one or more non-cationic lipids comprising from about 13 mol % to about 49.5 mol % of the total lipid present in the particle; and (d) one or more conjugated lipids that inhibit aggregation of particles comprising from about 0.5 mol % to about 2 mol % of the total lipid present in the particle.

In one aspect of this embodiment, the nucleic acid-lipid particle comprises: (a) one or more (e.g., a cocktail) siRNA molecules described herein (e.g., see, Table B); (b) a cationic lipid or a salt thereof comprising from about 52 mol % to about 62 mol % of the total lipid present in the particle; (c) a mixture of a phospholipid and cholesterol or a derivative thereof comprising from about 36 mol % to about 47 mol % of the total lipid present in the particle; and (d) a PEG-lipid conjugate comprising from about 1 mol % to about 2 mol % of the total lipid present in the particle. In one particular embodiment, the formulation is a four-component system comprising about 1.4 mol % PEG-lipid conjugate (e.g., PEG2000-C-DMA), about 57.1 mol % cationic lipid (e.g., DLin-K-C2-DMA) or a salt thereof, about 7.1 mol % DPPC (or DSPC), and about 34.3 mol % cholesterol (or derivative thereof).

In another aspect of this embodiment, the nucleic acid-lipid particle comprises: (a) one or more (e.g., a cocktail) siRNA molecules described herein (e.g., see, Table B); (b) a cationic lipid or a salt thereof comprising from about 56.5 mol % to about 66.5 mol % of the total lipid present in the particle; (c) cholesterol or a derivative thereof comprising from about 31.5 mol % to about 42.5 mol % of the total lipid present in the particle; and (d) a PEG-lipid conjugate comprising from about 1 mol % to about 2 mol % of the total lipid present in the particle. In one particular embodiment, the formulation is a three-component system which is phospholipid-free and comprises about 1.5 mol % PEG-lipid conjugate (e.g., PEG2000-C-DMA), about 61.5 mol % cationic lipid (e.g., DLin-K-C2-DMA) or a salt thereof, and about 36.9 mol % cholesterol (or derivative thereof).

Additional formulations are described in PCT Publication No. WO 09/127060 and published US patent application publication number US 2011/0071208 A1, the disclosures of which are herein incorporated by reference in their entirety for all purposes.

In other embodiments, the present invention provides nucleic acid-lipid particles comprising: (a) one or more (e.g., a cocktail) siRNA molecules described herein (e.g., see, Table B); (b) one or more cationic lipids or salts thereof comprising from about 2 mol % to about 50 mol % of the total lipid present in the particle; (c) one or more non-cationic lipids comprising from about 5 mol % to about 90 mol % of the total lipid present in the particle; and (d) one or more conjugated lipids that inhibit aggregation of particles comprising from about 0.5 mol % to about 20 mol % of the total lipid present in the particle.

In one aspect of this embodiment, the nucleic acid-lipid particle comprises: (a) one or more (e.g., a cocktail) siRNA molecules described herein (e.g., see, Table B); (b) a cationic lipid or a salt thereof comprising from about 30 mol % to about 50 mol % of the total lipid present in the particle; (c) a mixture of a phospholipid and cholesterol or a derivative thereof comprising from about 47 mol % to about 69 mol % of the total lipid present in the particle; and (d) a PEG-lipid conjugate comprising from about 1 mol % to about 3 mol % of the total lipid present in the particle. In one particular embodiment, the formulation is a four-component system which comprises about 2 mol % PEG-lipid conjugate (e.g., PEG2000-C-DMA), about 40 mol % cationic lipid (e.g., DLin-K-C2-DMA) or a salt thereof, about 10 mol % DPPC (or DSPC), and about 48 mol % cholesterol (or derivative thereof).

In further embodiments, the present invention provides nucleic acid-lipid particles comprising: (a) one or more (e.g., a cocktail) siRNA molecules described herein (e.g., see, Table B); (b) one or more cationic lipids or salts thereof comprising from about 50 mol % to about 65 mol % of the total lipid present in the particle; (c) one or more non-cationic lipids comprising from about 25 mol % to about 45 mol % of the total lipid present in the particle; and (d) one or more conjugated lipids that inhibit aggregation of particles comprising from about 5 mol % to about 10 mol % of the total lipid present in the particle.

In one aspect of this embodiment, the nucleic acid-lipid particle comprises: (a) one or more (e.g., a cocktail) siRNA molecules described herein (e.g., see, Table B); (b) a cationic lipid or a salt thereof comprising from about 50 mol % to about 60 mol % of the total lipid present in the particle; (c) a mixture of a phospholipid and cholesterol or a derivative thereof comprising from about 35 mol % to about 45 mol % of the total lipid present in the particle; and (d) a PEG-lipid conjugate comprising from about 5 mol % to about 10 mol % of the total lipid present in the particle. In certain instances, the non-cationic lipid mixture in the formulation comprises: (i) a phospholipid of from about 5 mol % to about 10 mol % of the total lipid present in the particle; and (ii) cholesterol or a derivative thereof of from about 25 mol % to about 35 mol % of the total lipid present in the particle. In one particular embodiment, the formulation is a four-component system which comprises about 7 mol % PEG-lipid conjugate (e.g., PEG750-C-DMA), about 54 mol % cationic lipid (e.g., DLin-K-C2-DMA) or a salt thereof, about 7 mol % DPPC (or DSPC), and about 32 mol % cholesterol (or derivative thereof).

In another aspect of this embodiment, the nucleic acid-lipid particle comprises: (a) one or more (e.g., a cocktail) siRNA molecules described herein (e.g., see, Table B); (b) a cationic lipid or a salt thereof comprising from about 55 mol % to about 65 mol % of the total lipid present in the particle; (c) cholesterol or a derivative thereof comprising from about 30 mol % to about 40 mol % of the total lipid present in the particle; and (d) a PEG-lipid conjugate comprising from about 5 mol % to about 10 mol % of the total lipid present in the particle. In one particular embodiment, the formulation is a three-component system which is phospholipid-free and comprises about 7 mol % PEG-lipid conjugate (e.g., PEG750-C-DMA), about 58 mol % cationic lipid (e.g., DLin-K-C2-DMA) or a salt thereof, and about 35 mol % cholesterol (or derivative thereof).

Additional embodiments of useful formulations are described in published US patent application publication number US 2011/0076335 A1, the disclosure of which is herein incorporated by reference in its entirety for all purposes.

In certain embodiments of the invention, the nucleic acid-lipid particle comprises: (a) one or more (e.g., a cocktail) siRNA molecules described herein (e.g., see, Table B); (b) a cationic lipid or a salt thereof comprising from about 48 mol % to about 62 mol % of the total lipid present in the particle; (c) a mixture of a phospholipid and cholesterol or a derivative thereof, wherein the phospholipid comprises about 7 mol % to about 17 mol % of the total lipid present in the particle, and wherein the cholesterol or derivative thereof comprises about 25 mol % to about 40 mol % of the total lipid present in the particle; and (d) a PEG-lipid conjugate comprising from about 0.5 mol % to about 3.0 mol % of the total lipid present in the particle. Exemplary lipid formulations A-Z of this aspect of the invention are included below.

Exemplary lipid formulation A includes the following components (wherein the percentage values of the components are mole percent): PEG-lipid (1.2%), cationic lipid (53.2%), phospholipid (9.3%), cholesterol (36.4%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DMA (compound (66)) (1.2%), the cationic lipid is 1,2-dilinoleyloxy-N,N-dimethylaminopropane (DLinDMA) (53.2%), the phospholipid is DPPC (9.3%), and cholesterol is present at 36.4%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a nucleic acid-lipid particle based on formulation A, which comprises one or more siRNA molecules described herein. For example, in certain embodiments, the nucleic acid lipid particle based on formulation A may comprise two different siRNA molecules. In certain other embodiments, the nucleic acid lipid particle based on formulation A may comprise three different siRNA molecules. In certain embodiments, the nucleic acid-lipid particle has a total lipid:siRNA mass ratio of from about 5:1 to about 15:1, or about 5:1, 6:1, 7:1, 8:1, 9:1, 10:1, 11:1, 12:1, 13:1, 14:1, or 15:1, or any fraction thereof or range therein. In certain embodiments, the nucleic acid-lipid particle has a total lipid:siRNA mass ratio of about 9:1 (e.g., a lipid:drug ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1).

Exemplary lipid formulation B which includes the following components (wherein the percentage values of the components are mole percent): PEG-lipid (0.8%), cationic lipid (59.7%), phospholipid (14.2%), cholesterol (25.3%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DOMG (compound (67)) (0.8%), the cationic lipid is 1,2-dilinoleyloxy-N,N-dimethylaminopropane (DLinDMA) (59.7%), the phospholipid is DSPC (14.2%), and cholesterol is present at 25.3%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a nucleic acid-lipid particle based on formulation B, which comprises one or more siRNA molecules described herein. For example, in certain embodiments, the nucleic acid lipid particle based on formulation B may comprise two different siRNA molecules. In certain other embodiments, the nucleic acid lipid particle based on formulation B may comprise three different siRNA molecules. In certain embodiments, the nucleic acid-lipid particle has a total lipid:siRNA mass ratio of from about 5:1 to about 15:1, or about 5:1, 6:1, 7:1, 8:1, 9:1, 10:1, 11:1, 12:1, 13:1, 14:1, or 15:1, or any fraction thereof or range therein. In certain embodiments, the nucleic acid-lipid particle has a total lipid:siRNA mass ratio of about 9:1 (e.g., a lipid:drug ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1).

Exemplary lipid formulation C includes the following components (wherein the percentage values of the components are mole percent): PEG-lipid (1.9%), cationic lipid (52.5%), phospholipid (14.8%), cholesterol (30.8%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DOMG (compound (67)) (1.9%), the cationic lipid is 1,2-di-γ-linolenyloxy-N,N-dimethylaminopropane (γ-DLenDMA; Compound (15)) (52.5%), the phospholipid is DSPC (14.8%), and cholesterol is present at 30.8%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a nucleic acid-lipid particle based on formulation C, which comprises one or more siRNA molecules described herein. For example, in certain embodiments, the nucleic acid lipid particle based on formulation C may comprise two different siRNA molecules. In certain other embodiments, the nucleic acid lipid particle based on formulation C may comprise three different siRNA molecules. In certain embodiments, the nucleic acid-lipid particle has a total lipid:siRNA mass ratio of from about 5:1 to about 15:1, or about 5:1, 6:1, 7:1, 8:1, 9:1, 10:1, 11:1, 12:1, 13:1, 14:1, or 15:1, or any fraction thereof or range therein. In certain embodiments, the nucleic acid-lipid particle has a total lipid:siRNA mass ratio of about 9:1 (e.g., a lipid:drug ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1).

Exemplary lipid formulation D includes the following components (wherein the percentage values of the components are mole percent): PEG-lipid (0.7%), cationic lipid (60.3%), phospholipid (8.4%), cholesterol (30.5%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DMA (compound (66)) (0.7%), the cationic lipid is 3-((6Z,9Z,28Z,31Z)-heptatriaconta-6,9,28,31-tetraen-19-yloxy)-N,N-dimethylpropan-1-amine (DLin-MP-DMA; Compound (8) (60.3%), the phospholipid is DSPC (8.4%), and cholesterol is present at 30.5%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a nucleic acid-lipid particle based on formulation D, which comprises one or more siRNA molecules described herein. For example, in certain embodiments, the nucleic acid lipid particle based on formulation D may comprise two different siRNA molecules. In certain other embodiments, the nucleic acid lipid particle based on formulation D may comprise three different siRNA molecules. In certain embodiments, the nucleic acid-lipid particle has a total lipid:siRNA mass ratio of from about 5:1 to about 15:1, or about 5:1, 6:1, 7:1, 8:1, 9:1, 10:1, 11:1, 12:1, 13:1, 14:1, or 15:1, or any fraction thereof or range therein. In certain embodiments, the nucleic acid-lipid particle has a total lipid:siRNA mass ratio of about 9:1 (e.g., a lipid:drug ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1).

Exemplary lipid formulation E includes the following components (wherein the percentage values of the components are mole percent): PEG-lipid (1.8%), cationic lipid (52.1%), phospholipid (7.5%), cholesterol (38.5%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DMA (compound (66)) (1.8%), the cationic lipid is (6Z,9Z,28Z,31Z)-heptatriaconta-6,9,28,31-tetraen-19-yl 4-(dimethylamino)butanoate) (Compound (7)) (52.1%), the phospholipid is DPPC (7.5%), and cholesterol is present at 38.5%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a nucleic acid-lipid particle based on formulation E, which comprises one or more siRNA molecules described herein. For example, in certain embodiments, the nucleic acid lipid particle based on formulation E may comprise two different siRNA molecules. In certain other embodiments, the nucleic acid lipid particle based on formulation E may comprise three different siRNA molecules. In certain embodiments, the nucleic acid-lipid particle has a total lipid:siRNA mass ratio of from about 5:1 to about 15:1, or about 5:1, 6:1, 7:1, 8:1, 9:1, 10:1, 11:1, 12:1, 13:1, 14:1, or 15:1, or any fraction thereof or range therein. In certain embodiments, the nucleic acid-lipid particle has a total lipid:siRNA mass ratio of about 9:1 (e.g., a lipid:drug ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1).

Exemplary formulation F includes the following components (wherein the percentage values of the components are mole percent): PEG-lipid (0.9%), cationic lipid (57.1%), phospholipid (8.1%), cholesterol (33.8%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DOMG (compound (67)) (0.9%), the cationic lipid is 1,2-dilinolenyloxy-N,N-dimethylaminopropane (DLenDMA), 1,2-di-γ-linolenyloxy-N,N-dimethylaminopropane (γ-DLenDMA; Compound (15)) (57.1%), the phospholipid is DSPC (8.1%), and cholesterol is present at 33.8%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a nucleic acid-lipid particle based on formulation F, which comprises one or more siRNA molecules described herein. For example, in certain embodiments, the nucleic acid lipid particle based on formulation F may comprise two different siRNA molecules. In certain other embodiments, the nucleic acid lipid particle based on formulation F may comprise three different siRNA molecules. In certain embodiments, the nucleic acid-lipid particle has a total lipid:siRNA mass ratio of from about 5:1 to about 15:1, or about 5:1, 6:1, 7:1, 8:1, 9:1, 10:1, 11:1, 12:1, 13:1, 14:1, or 15:1, or any fraction thereof or range therein. In certain embodiments, the nucleic acid-lipid particle has a total lipid:siRNA mass ratio of about 9:1 (e.g., a lipid:drug ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1).

Exemplary lipid formulation G includes the following components (wherein the percentage values of the components are mole percent): PEG-lipid (1.7%), cationic lipid (61.6%), phospholipid (11.2%), cholesterol (25.5%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DOMG (compound (67)) (1.7%), the cationic lipid is 1,2-dilinolenyloxy-N,N-dimethylaminopropane (DLenDMA), 1,2-di-γ-linolenyloxy-N,N-dimethylaminopropane (γ-DLenDMA; Compound (15)) (61.6%), the phospholipid is DPPC (11.2%), and cholesterol is present at 25.5%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a nucleic acid-lipid particle based on formulation G, which comprises one or more siRNA molecules described herein. For example, in certain embodiments, the nucleic acid lipid particle based on formulation G may comprise two different siRNA molecules. In certain other embodiments, the nucleic acid lipid particle based on formulation G may comprise three different siRNA molecules. In certain embodiments, the nucleic acid-lipid particle has a total lipid:siRNA mass ratio of from about 5:1 to about 15:1, or about 5:1, 6:1, 7:1, 8:1, 9:1, 10:1, 11:1, 12:1, 13:1, 14:1, or 15:1, or any fraction thereof or range therein. In certain embodiments, the nucleic acid-lipid particle has a total lipid:siRNA mass ratio of about 9:1 (e.g., a lipid:drug ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1).

Exemplary lipid formulation H includes the following components (wherein the percentage values of the components are mole percent): PEG-lipid (1.1%), cationic lipid (55.0%), phospholipid (11.0%), cholesterol (33.0%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DMA (compound (66)) (1.1%), the cationic lipid is (6Z,16Z)-12-((Z)-dec-4-enyl)docosa-6,16-dien-11-yl 5-(dimethylamino)pentanoate (Compound (13)) (55.0%), the phospholipid is DSPC (11.0%), and cholesterol is present at 33.0%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a nucleic acid-lipid particle based on formulation H, which comprises one or more siRNA molecules described herein. For example, in certain embodiments, the nucleic acid lipid particle based on formulation H may comprise two different siRNA molecules. In certain other embodiments, the nucleic acid lipid particle based on formulation H may comprise three different siRNA molecules. In certain embodiments, the nucleic acid-lipid particle has a total lipid:siRNA mass ratio of from about 5:1 to about 15:1, or about 5:1, 6:1, 7:1, 8:1, 9:1, 10:1, 11:1, 12:1, 13:1, 14:1, or 15:1, or any fraction thereof or range therein. In certain embodiments, the nucleic acid-lipid particle has a total lipid:siRNA mass ratio of about 9:1 (e.g., a lipid:drug ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1).

Exemplary lipid formulation I includes the following components (wherein the percentage values of the components are mole percent): PEG-lipid (2.6%), cationic lipid (53.1%), phospholipid (9.4%), cholesterol (35.0%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DMA (compound (66)) (2.6%), the cationic lipid is (6Z,16Z)-12-((Z)-dec-4-enyl)docosa-6,16-dien-11-yl 5-(dimethylamino)pentanoate (Compound (13)) (53.1%), the phospholipid is DSPC (9.4%), and cholesterol is present at 35.0%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a nucleic acid-lipid particle based on formulation I, which comprises one or more siRNA molecules described herein. For example, in certain embodiments, the nucleic acid lipid particle based on formulation I may comprise two different siRNA molecules. In certain other embodiments, the nucleic acid lipid particle based on formulation I may comprise three different siRNA molecules. In certain embodiments, the nucleic acid-lipid particle has a total lipid:siRNA mass ratio of from about 5:1 to about 15:1, or about 5:1, 6:1, 7:1, 8:1, 9:1, 10:1, 11:1, 12:1, 13:1, 14:1, or 15:1, or any fraction thereof or range therein. In certain embodiments, the nucleic acid-lipid particle has a total lipid:siRNA mass ratio of about 9:1 (e.g., a lipid:drug ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1).

Exemplary lipid formulation J includes the following components (wherein the percentage values of the components are mole percent): PEG-lipid (0.6%), cationic lipid (59.4%), phospholipid (10.2%), cholesterol (29.8%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DMA (compound (66)) (0.6%), the cationic lipid is 1,2-dilinoleyloxy-N,N-dimethylaminopropane (DLinDMA) (59.4%), the phospholipid is DPPC (10.2%), and cholesterol is present at 29.8%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a nucleic acid-lipid particle based on formulation J, which comprises one or more siRNA molecules described herein. For example, in certain embodiments, the nucleic acid lipid particle based on formulation J may comprise two different siRNA molecules. In certain other embodiments, the nucleic acid lipid particle based on formulation J may comprise three different siRNA molecules. In certain embodiments, the nucleic acid-lipid particle has a total lipid:siRNA mass ratio of from about 5:1 to about 15:1, or about 5:1, 6:1, 7:1, 8:1, 9:1, 10:1, 11:1, 12:1, 13:1, 14:1, or 15:1, or any fraction thereof or range therein. In certain embodiments, the nucleic acid-lipid particle has a total lipid:siRNA mass ratio of about 9:1 (e.g., a lipid:drug ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1).

Exemplary lipid formulation K includes the following components (wherein the percentage values of the components are mole percent): PEG-lipid (0.5%), cationic lipid (56.7%), phospholipid (13.1%), cholesterol (29.7%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DOMG (compound (67)) (0.5%), the cationic lipid is (6Z,9Z,28Z,31Z)-heptatriaconta-6,9,28,31-tetraen-19-yl 4-(dimethylamino)butanoate) (Compound (7)) (56.7%); the phospholipid is DSPC (13.1%), and cholesterol is present at 29.7%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a nucleic acid-lipid particle based on formulation K, which comprises one or more siRNA molecules described herein. For example, in certain embodiments, the nucleic acid lipid particle based on formulation K may comprise two different siRNA molecules. In certain other embodiments, the nucleic acid lipid particle based on formulation K may comprise three different siRNA molecules. In certain embodiments, the nucleic acid-lipid particle has a total lipid:siRNA mass ratio of from about 5:1 to about 15:1, or about 5:1, 6:1, 7:1, 8:1, 9:1, 10:1, 11:1, 12:1, 13:1, 14:1, or 15:1, or any fraction thereof or range therein. In certain embodiments, the nucleic acid-lipid particle has a total lipid:siRNA mass ratio of about 9:1 (e.g., a lipid:drug ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1).

Exemplary lipid formulation L includes the following components (wherein the percentage values of the components are mole percent): PEG-lipid (2.2%), cationic lipid (52.0%), phospholipid (9.7%), cholesterol (36.2%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DOMG (compound (67)) (2.2%), the cationic lipid is 1,2-di-γ-linolenyloxy-N,N-dimethylaminopropane (γ-DLenDMA; Compound (15)) (52.0%), the phospholipid is DSPC (9.7%), and cholesterol is present at 36.2%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a nucleic acid-lipid particle based on formulation L, which comprises one or more siRNA molecules described herein. For example, in certain embodiments, the nucleic acid lipid particle based on formulation L may comprise two different siRNA molecules. In certain other embodiments, the nucleic acid lipid particle based on formulation L may comprise three different siRNA molecules. In certain embodiments, the nucleic acid-lipid particle has a total lipid:siRNA mass ratio of from about 5:1 to about 15:1, or about 5:1, 6:1, 7:1, 8:1, 9:1, 10:1, 11:1, 12:1, 13:1, 14:1, or 15:1, or any fraction thereof or range therein. In certain embodiments, the nucleic acid-lipid particle has a total lipid:siRNA mass ratio of about 9:1 (e.g., a lipid:drug ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1).

Exemplary lipid formulation M includes the following components (wherein the percentage values of the components are mole percent): PEG-lipid (2.7%), cationic lipid (58.4%), phospholipid (13.1%), cholesterol (25.7%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DMA (compound (66)) (2.7%), the cationic lipid is 1,2-dilinoleyloxy-N,N-dimethylaminopropane (DLinDMA) (58.4%), the phospholipid is DPPC (13.1%), and cholesterol is present at 25.7%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a nucleic acid-lipid particle based on formulation M, which comprises one or more siRNA molecules described herein. For example, in certain embodiments, the nucleic acid lipid particle based on formulation M may comprise two different siRNA molecules. In certain other embodiments, the nucleic acid lipid particle based on formulation M may comprise three different siRNA molecules. In certain embodiments, the nucleic acid-lipid particle has a total lipid:siRNA mass ratio of from about 5:1 to about 15:1, or about 5:1, 6:1, 7:1, 8:1, 9:1, 10:1, 11:1, 12:1, 13:1, 14:1, or 15:1, or any fraction thereof or range therein. In certain embodiments, the nucleic acid-lipid particle has a total lipid:siRNA mass ratio of about 9:1 (e.g., a lipid:drug ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1).

Exemplary lipid formulation N includes the following components (wherein the percentage values of the components are mole percent): PEG-lipid (3.0%), cationic lipid (53.3%), phospholipid (12.1%), cholesterol (31.5%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DMA (compound (66)) (3.0%), the cationic lipid is 1,2-dilinoleyloxy-N,N-dimethylaminopropane (DLinDMA) (53.3%), the phospholipid is DPPC (12.1%), and cholesterol is present at 31.5%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a nucleic acid-lipid particle based on formulation N, which comprises one or more siRNA molecules described herein. For example, in certain embodiments, the nucleic acid lipid particle based on formulation N may comprise two different siRNA molecules. In certain other embodiments, the nucleic acid lipid particle based on formulation N may comprise three different siRNA molecules. In certain embodiments, the nucleic acid-lipid particle has a total lipid:siRNA mass ratio of from about 5:1 to about 15:1, or about 5:1, 6:1, 7:1, 8:1, 9:1, 10:1, 11:1, 12:1, 13:1, 14:1, or 15:1, or any fraction thereof or range therein. In certain embodiments, the nucleic acid-lipid particle has a total lipid:siRNA mass ratio of about 9:1 (e.g., a lipid:drug ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1).

Exemplary lipid formulation O includes the following components (wherein the percentage values of the components are mole percent): PEG-lipid (1.5%), cationic lipid (56.2%), phospholipid (7.8%), cholesterol (34.7%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DMA (compound (66)) (1.5%), the cationic lipid is 1,2-dilinoleyloxy-N,N-dimethylaminopropane (DLinDMA) (56.2%), the phospholipid is DPPC (7.8%), and cholesterol is present at 34.7%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a nucleic acid-lipid particle based on formulation O, which comprises one or more siRNA molecules described herein. For example, in certain embodiments, the nucleic acid lipid particle based on formulation O may comprise two different siRNA molecules. In certain other embodiments, the nucleic acid lipid particle based on formulation O may comprise three different siRNA molecules. In certain embodiments, the nucleic acid-lipid particle has a total lipid:siRNA mass ratio of from about 5:1 to about 15:1, or about 5:1, 6:1, 7:1, 8:1, 9:1, 10:1, 11:1, 12:1, 13:1, 14:1, or 15:1, or any fraction thereof or range therein. In certain embodiments, the nucleic acid-lipid particle has a total lipid:siRNA mass ratio of about 9:1 (e.g., a lipid:drug ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1).

Exemplary lipid formulation P includes the following components (wherein the percentage values of the components are mole percent): PEG-lipid (2.1%), cationic lipid (48.6%), phospholipid (15.5%), cholesterol (33.8%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DOMG (compound (67)) (2.1%), the cationic lipid is 3-((6Z,9Z,28Z,31Z)-heptatriaconta-6,9,28,31-tetraen-19-yloxy)-N,N-dimethylpropan-1-amine (DLinMP-DMA; Compound (8)) (48.6%), the phospholipid is DSPC (15.5%), and cholesterol is present at 33.8%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a nucleic acid-lipid particle based on formulation P, which comprises one or more siRNA molecules described herein. For example, in certain embodiments, the nucleic acid lipid particle based on formulation P may comprise two different siRNA molecules. In certain other embodiments, the nucleic acid lipid particle based on formulation P may comprise three different siRNA molecules. In certain embodiments, the nucleic acid-lipid particle has a total lipid:siRNA mass ratio of from about 5:1 to about 15:1, or about 5:1, 6:1, 7:1, 8:1, 9:1, 10:1, 11:1, 12:1, 13:1, 14:1, or 15:1, or any fraction thereof or range therein. In certain embodiments, the nucleic acid-lipid particle has a total lipid:siRNA mass ratio of about 9:1 (e.g., a lipid:drug ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1).

Exemplary lipid formulation Q includes the following components (wherein the percentage values of the components are mole percent): PEG-lipid (2.5%), cationic lipid (57.9%), phospholipid (9.2%), cholesterol (30.3%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DMA (compound (66)) (2.5%), the cationic lipid is (6Z,16Z)-12-((Z)-dec-4-enyl)docosa-6,16-dien-11-yl 5-(dimethylamino)pentanoate (Compound (13)) (57.9%), the phospholipid is DSPC (9.2%), and cholesterol is present at 30.3%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a nucleic acid-lipid particle based on formulation Q, which comprises one or more siRNA molecules described herein. For example, in certain embodiments, the nucleic acid lipid particle based on formulation Q may comprise two different siRNA molecules. In certain other embodiments, the nucleic acid lipid particle based on formulation Q may comprise three different siRNA molecules. In certain embodiments, the nucleic acid-lipid particle has a total lipid:siRNA mass ratio of from about 5:1 to about 15:1, or about 5:1, 6:1, 7:1, 8:1, 9:1, 10:1, 11:1, 12:1, 13:1, 14:1, or 15:1, or any fraction thereof or range therein. In certain embodiments, the nucleic acid-lipid particle has a total lipid:siRNA mass ratio of about 9:1 (e.g., a lipid:drug ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1).

Exemplary lipid formulation R includes the following components (wherein the percentage values of the components are mole percent): PEG-lipid (1.6%), cationic lipid (54.6%), phospholipid (10.9%), cholesterol (32.8%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DMA (compound (66)) (1.6%), the cationic lipid is 3-((6Z,9Z,28Z,31Z)-heptatriaconta-6,9,28,31-tetraen-19-yloxy)-N,N-dimethylpropan-1-amine (Compound (8)) (54.6%), the phospholipid is DSPC (10.9%), and cholesterol is present at 32.8%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a nucleic acid-lipid particle based on formulation R, which comprises one or more siRNA molecules described herein. For example, in certain embodiments, the nucleic acid lipid particle based on formulation R may comprise two different siRNA molecules. In certain other embodiments, the nucleic acid lipid particle based on formulation R may comprise three different siRNA molecules. In certain embodiments, the nucleic acid-lipid particle has a total lipid:siRNA mass ratio of from about 5:1 to about 15:1, or about 5:1, 6:1, 7:1, 8:1, 9:1, 10:1, 11:1, 12:1, 13:1, 14:1, or 15:1, or any fraction thereof or range therein. In certain embodiments, the nucleic acid-lipid particle has a total lipid:siRNA mass ratio of about 9:1 (e.g., a lipid:drug ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1).

Exemplary lipid formulation S includes the following components (wherein the percentage values of the components are mole percent): PEG-lipid (2.9%), cationic lipid (49.6%), phospholipid (16.3%), cholesterol (31.3%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DMA (compound (66)) (2.9%), the cationic lipid is (6Z,16Z)-12-((Z)-dec-4-enyl)docosa-6,16-dien-11-yl 5-(dimethylamino)pentanoate (Compound (13)) (49.6%), the phospholipid is DPPC (16.3%), and cholesterol is present at 31.3%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a nucleic acid-lipid particle based on formulation S, which comprises one or more siRNA molecules described herein. For example, in certain embodiments, the nucleic acid lipid particle based on formulation S may comprise two different siRNA molecules. In certain other embodiments, the nucleic acid lipid particle based on formulation S may comprise three different siRNA molecules. In certain embodiments, the nucleic acid-lipid particle has a total lipid:siRNA mass ratio of from about 5:1 to about 15:1, or about 5:1, 6:1, 7:1, 8:1, 9:1, 10:1, 11:1, 12:1, 13:1, 14:1, or 15:1, or any fraction thereof or range therein. In certain embodiments, the nucleic acid-lipid particle has a total lipid:siRNA mass ratio of about 9:1 (e.g., a lipid:drug ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1).

Exemplary lipid formulation T includes the following components (wherein the percentage values of the components are mole percent): PEG-lipid (0.7%), cationic lipid (50.5%), phospholipid (8.9%), cholesterol (40.0%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DOMG (compound (67)) (0.7%), the cationic lipid is 1,2-dilinoleyloxy-N,N-dimethylaminopropane (DLinDMA) (50.5%), the phospholipid is DPPC (8.9%), and cholesterol is present at 40.0%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a nucleic acid-lipid particle based on formulation T, which comprises one or more siRNA molecules described herein. For example, in certain embodiments, the nucleic acid lipid particle based on formulation T may comprise two different siRNA molecules. In certain other embodiments, the nucleic acid lipid particle based on formulation T may comprise three different siRNA molecules. In certain embodiments, the nucleic acid-lipid particle has a total lipid:siRNA mass ratio of from about 5:1 to about 15:1, or about 5:1, 6:1, 7:1, 8:1, 9:1, 10:1, 11:1, 12:1, 13:1, 14:1, or 15:1, or any fraction thereof or range therein. In certain embodiments, the nucleic acid-lipid particle has a total lipid:siRNA mass ratio of about 9:1 (e.g., a lipid:drug ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1).

Exemplary lipid formulation U includes the following components (wherein the percentage values of the components are mole percent): PEG-lipid (1.0%), cationic lipid (51.4%), phospholipid (15.0%), cholesterol (32.6%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DOMG (compound (67)) (1.0%), the cationic lipid is 1,2-dilinoleyloxy-N,N-dimethylaminopropane (DLinDMA) (51.4%), the phospholipid is DSPC (15.0%), and cholesterol is present at 32.6%, wherein the actual amounts of the lipids present may vary by, e.g., ±5% (or e.g., ±4 mol %, ±3 mol %, ±2 mol %, ±1 mol %, ±0.75 mol %, 0.5 mol %, ±0.25 mol %, or ±0.1 mol %). Thus, certain embodiments of the invention provide a nucleic acid-lipid particle based on formulation U, which comprises one or more siRNA molecules described herein. For example, in certain embodiments, the nucleic acid lipid particle based on formulation U may comprise two different siRNA molecules. In certain other embodiments, the nucleic acid lipid particle based on formulation U may comprise three different siRNA molecules. In certain embodiments, the nucleic acid-lipid particle has a total lipid:siRNA mass ratio of from about 5:1 to about 15:1, or about 5:1, 6:1, 7:1, 8:1, 9:1, 10:1, 11:1, 12:1, 13:1, 14:1, or 15:1, or any fraction thereof or range therein. In certain embodiments, the nucleic acid-lipid particle has a total lipid:siRNA mass ratio of about 9:1 (e.g., a lipid:drug ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1).

Exemplary lipid formulation V includes the following components (wherein the percentage values of the components are mole percent): PEG-lipid (1.3%), cationic lipid (60.0%), phospholipid (7.2%), cholesterol (31.5%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DOMG (compound (67)) (1.3%), the cationic lipid is 1,2-dilinolenyloxy-N,N-dimethylaminopropane (DLenDMA) (60.0%), the phospholipid is DSPC (7.2%), and cholesterol is present at 31.5%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a nucleic acid-lipid particle based on formulation V, which comprises one or more siRNA molecules described herein. For example, in certain embodiments, the nucleic acid lipid particle based on formulation V may comprise two different siRNA molecules. In certain other embodiments, the nucleic acid lipid particle based on formulation V may comprise three different siRNA molecules. In certain embodiments, the nucleic acid-lipid particle has a total lipid:siRNA mass ratio of from about 5:1 to about 15:1, or about 5:1, 6:1, 7:1, 8:1, 9:1, 10:1, 11:1, 12:1, 13:1, 14:1, or 15:1, or any fraction thereof or range therein. In certain embodiments, the nucleic acid-lipid particle has a total lipid:siRNA mass ratio of about 9:1 (e.g., a lipid:drug ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1).

Exemplary lipid formulation W includes the following components (wherein the percentage values of the components are mole percent): PEG-lipid (1.8%), cationic lipid (51.6%), phospholipid (8.4%), cholesterol (38.3%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DMA (compound (66)) (1.8%), the cationic lipid is 1,2-dilinoleyloxy-N,N-dimethylaminopropane (DLinDMA) (51.6%), the phospholipid is DSPC (8.4%), and cholesterol is present at 38.3%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a nucleic acid-lipid particle based on formulation W, which comprises one or more siRNA molecules described herein. For example, in certain embodiments, the nucleic acid lipid particle based on formulation W may comprise two different siRNA molecules. In certain other embodiments, the nucleic acid lipid particle based on formulation W may comprise three different siRNA molecules, In certain embodiments, the nucleic acid-lipid particle has a total lipid:siRNA mass ratio of from about 5:1 to about 15:1, or about 5:1, 6:1, 7:1, 8:1, 9:1, 10:1, 11:1, 12:1, 13:1, 14:1, or 15:1, or any fraction thereof or range therein. In certain embodiments, the nucleic acid-lipid particle has a total lipid:siRNA mass ratio of about 9:1 (e.g., a lipid:drug ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1).

Exemplary lipid formulation X includes the following components (wherein the percentage values of the components are mole percent): PEG-lipid (2.4%), cationic lipid (48.5%), phospholipid (10.0%), cholesterol (39.2%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DMA (compound (66)) (2.4%), the cationic lipid is 1,2-di-γ-linolenyloxy-N,N-dimethylaminopropane (γ-DLenDMA; Compound (15)) (48.5%), the phospholipid is DPPC (10.0%), and cholesterol is present at 39.2%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a nucleic acid-lipid particle based on formulation X, which comprises one or more siRNA molecules described herein. For example, in certain embodiments, the nucleic acid lipid particle based on formulation X may comprise two different siRNA molecules. In certain other embodiments, the nucleic acid lipid particle based on formulation X may comprise three different siRNA molecules. In certain embodiments, the nucleic acid-lipid particle has a total lipid:siRNA mass ratio of from about 5:1 to about 15:1, or about 5:1, 6:1, 7:1, 8:1, 9:1, 10:1, 11:1, 12:1, 13:1, 14:1, or 15:1, or any fraction thereof or range therein. In certain embodiments, the nucleic acid-lipid particle has a total lipid:siRNA mass ratio of about 9:1 (e.g., a lipid:drug ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1).

Exemplary lipid formulation Y includes the following components (wherein the percentage values of the components are mole percent): PEG-lipid (2.6%), cationic lipid (61.2%), phospholipid (7.1%), cholesterol (29.2%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DMA (compound (66)) (2.6%), the cationic lipid is (6Z,16Z)-12-((Z)-dec-4-enyl)docosa-6,16-dien-11-yl 5-(dimethylamino)pentanoate (Compound (13)) (61.2%), the phospholipid is DSPC (7.1%), and cholesterol is present at 29.2%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a nucleic acid-lipid particle based on formulation Y, which comprises one or more siRNA molecules described herein. For example, in certain embodiments, the nucleic acid lipid particle based on formulation Y may comprise two different siRNA molecules. In certain other embodiments, the nucleic acid lipid particle based on formulation Y may comprise three different siRNA molecules. In certain embodiments, the nucleic acid-lipid particle has a total lipid:siRNA mass ratio of from about 5:1 to about 15:1, or about 5:1, 6:1, 7:1, 8:1, 9:1, 10:1, 11:1, 12:1, 13:1, 14:1, or 15:1, or any fraction thereof or range therein. In certain embodiments, the nucleic acid-lipid particle has a total lipid:siRNA mass ratio of about 9:1 (e.g., a lipid:drug ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1).

Exemplary lipid formulation Z includes the following components (wherein the percentage values of the components are mole percent): PEG-lipid (2.2%), cationic lipid (49.7%), phospholipid (12.1%), cholesterol (36.0%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DOMG (compound (67)) (2.2%), the cationic lipid is (6Z,9Z,28Z,31Z)-heptatriaconta-6,9,28,31-tetraen-19-yl 4-(dimethylamino)butanoate) (Compound (7)) (49.7%), the phospholipid is DPPC (12.1%), and cholesterol is present at 36.0%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a nucleic acid-lipid particle based on formulation Z, which comprises one or more siRNA molecules described herein. For example, in certain embodiments, the nucleic acid lipid particle based on formulation Z may comprise two different siRNA molecules. In certain other embodiments, the nucleic acid lipid particle based on formulation Z may comprise three different siRNA molecules. In certain embodiments, the nucleic acid-lipid particle has a total lipid:siRNA mass ratio of from about 5:1 to about 15:1, or about 5:1, 6:1, 7:1, 8:1, 9:1, 10:1, 11:1, 12:1, 13:1, 14:1, or 15:1, or any fraction thereof or range therein. In certain embodiments, the nucleic acid-lipid particle has a total lipid:siRNA mass ratio of about 9:1 (e.g., a lipid:drug ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1).

Accordingly, certain embodiments of the invention provide a nucleic acid-lipid particle described herein, wherein the lipids are formulated as described in any one of formulations A, B, C, D, E, F, G, H, I, J, K, L, M, N, O, P, Q, R, S, T, U, V, W, X, Y or Z.

The present invention also provides pharmaceutical compositions comprising a nucleic acid-lipid particle and a pharmaceutically acceptable carrier.

The nucleic acid-lipid particles of the present invention are useful, for example, for the therapeutic delivery of siRNAs that silence the expression of one or more MARV genes. In some embodiments, a cocktail of siRNAs that target different regions (e.g., overlapping and/or non-overlapping sequences) of an MARV gene or transcript is formulated into the same or different nucleic acid-lipid particles, and the particles are administered to a mammal (e.g., a human) requiring such treatment. In certain instances, a therapeutically effective amount of the nucleic acid-lipid particles can be administered to the mammal, e.g., for treating MARV infection in a human.

In certain embodiments, the present invention provides a method for introducing one or more siRNA molecules described herein into a cell by contacting the cell with a nucleic acid-lipid particle described herein.

In certain embodiments, the present invention provides a method for introducing one or more siRNA molecules that silence expression of a Marburg virus gene into a cell by contacting the cell with a nucleic acid-lipid particle described herein under conditions whereby the siRNA enters the cell and silences the expression of the Marburg virus gene within the cell. In certain embodiments, the cell is in a mammal, such as a human. In certain embodiments, the human has been diagnosed with a Marburg virus infection. In certain embodiments, silencing of the Marburg virus gene expression reduces Marburg virus particle load in the mammal by at least about 50% relative to Marburg virus particle load in the absence of the nucleic acid-lipid particle.

In some embodiments, the nucleic acid-lipid particles described herein are administered by one of the following routes of administration: oral, intranasal, intravenous, intraperitoneal, intramuscular, intra-articular, intralesional, intratracheal, subcutaneous, and intradermal. In particular embodiments, the nucleic acid-lipid particles are administered systemically, e.g., via enteral or parenteral routes of administration.

In certain aspects, the present invention provides methods for silencing MARV gene expression in a mammal (e.g., human) in need thereof, the method comprising administering to the mammal a therapeutically effective amount of a nucleic acid-lipid particle comprising one or more siRNAs described herein (e.g., one or more siRNAs shown in Table B). In some embodiments, administration of nucleic acid-lipid particles comprising one or more siRNAs described herein reduces MARV RNA levels by at least about 5%, 10%, 15%, 20%, 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% (or any range therein) relative to MARV RNA levels detected in the absence of the siRNA (e.g., buffer control or irrelevant non-MARV targeting siRNA control). In other embodiments, administration of nucleic acid-lipid particles comprising one or more MARV-targeting siRNAs reduces MARV RNA levels for at least about 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days or more (or any range therein) relative to a negative control such as, e.g., a buffer control or an irrelevant non-MARV targeting siRNA control.

In other aspects, the present invention provides methods for silencing MARV gene expression in a mammal (e.g., human) in need thereof, the method comprising administering to the mammal a therapeutically effective amount of a nucleic acid-lipid particle comprising one or more siRNAs described herein (e.g., siRNAs described in Table B). In some embodiments, administration of nucleic acid-lipid particles comprising one or more MARV siRNAs reduces MARV mRNA levels by at least about 5%, 10%, 15%, 20%, 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% (or any range therein) relative to MARV mRNA levels detected in the absence of the siRNA (e.g., buffer control or irrelevant non-MARV targeting siRNA control). In other embodiments, administration of nucleic acid-lipid particles comprising one or more MARV-targeting siRNAs reduces MARV mRNA levels for at least about 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days or more (or any range therein) relative to a negative control such as, e.g., a buffer control or an irrelevant non-MARV targeting siRNA control.

In other aspects, the present invention provides methods for treating, preventing, reducing the risk or likelihood of developing (e.g., reducing the susceptibility to), delaying the onset of, and/or ameliorating one or more symptoms associated with MARV infection in a mammal (e.g., human) in need thereof, the method comprising administering to the mammal a therapeutically effective amount of a nucleic acid-lipid particle comprising one or more siRNA molecules described herein (e.g., as described in Table B) that target MARV gene expression. Examples of symptoms associated with MARV infection in a human include fever, headache, joint and muscle aches, chills, sore throat, weakness, nausea and vomiting, diarrhea, raised rash, chest pain and cough, stomach pain, weight loss and bleeding from the nose, mouth, rectum, eyes and ears.

Certain embodiments of the invention provide a method for ameliorating one or more symptoms associated with Marburg virus infection in a human, the method comprising the step of administering to the human a therapeutically effective amount of a nucleic acid-lipid particle described herein, comprising one or more siRNA molecules described herein (e.g., as described in Table B). In certain embodiments, the particle is administered via a systemic route. In certain embodiments, the siRNA of the nucleic acid-lipid particle inhibits expression of a Marburg virus gene in the human.

In further aspects, the present invention provides a method for inactivating MARV in a mammal (e.g., human) in need thereof (e.g., a human suffering from MARV infection), the method comprising administering to the mammal a therapeutically effective amount of a nucleic acid-lipid particle comprising one or more siRNAs described herein that target MARV gene expression. In some embodiments, administration of nucleic acid-lipid particles comprising one or more MARV-targeting siRNAs lowers, reduces, or decreases MARV protein levels (e.g., MARV surface antigen protein) by at least about 5%, 10%, 15%, 20%, 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% (or any range therein) relative to the MARV protein levels detected in the absence of the siRNA (e.g., buffer control or irrelevant non-MARV targeting siRNA control).

By way of example, MARV mRNA can be measured using a branched DNA assay (QuantiGene®; Affymetrix). The branched DNA assay is a sandwich nucleic acid hybridization method that uses bDNA molecules to amplify signal from captured target RNA.

Therapeutic Nucleic Acids

The term "nucleic acid" includes any oligonucleotide or polynucleotide, with fragments containing up to 60 nucleotides generally termed oligonucleotides, and longer fragments termed polynucleotides. In particular embodiments, oligonucleotides of the invention are from about 15 to about 60 nucleotides in length. In some embodiments, nucleic acid is associated with a carrier system such as the lipid particles described herein. In certain embodiments, the nucleic acid is fully encapsulated in the lipid particle. Nucleic acid may be administered alone in the lipid particles of the invention, or in combination (e.g., co-administered) with lipid particles comprising peptides, polypeptides, or small molecules such as conventional drugs.

In the context of this invention, the terms "polynucleotide" and "oligonucleotide" refer to a polymer or oligomer of nucleotide or nucleoside monomers consisting of naturally-occurring bases, sugars and intersugar (backbone) linkages. The terms "polynucleotide" and "oligonucleotide" also include polymers or oligomers comprising non-naturally occurring monomers, or portions thereof, which function similarly. Such modified or substituted oligonucleotides are often preferred over native forms because of properties such as, for example, enhanced cellular uptake, reduced immunogenicity, and increased stability in the presence of nucleases.

Oligonucleotides are generally classified as deoxyribooligonucleotides or ribooligonucleotides. A deoxyribooligonucleotide consists of a 5-carbon sugar called deoxyribose joined covalently to phosphate at the 5' and 3' carbons of this sugar to form an alternating, unbranched polymer. A ribooligonucleotide consists of a similar repeating structure where the 5-carbon sugar is ribose.

In particular embodiments, an oligonucleotide (such as the sense and antisense RNA strands set forth in Tables C and D) of the invention specifically hybridizes to or is complementary to a target polynucleotide sequence. The terms "specifically hybridizable" and "complementary" as used herein indicate a sufficient degree of complementarity such that stable and specific binding occurs between the DNA or RNA target and the oligonucleotide. It is understood that an oligonucleotide need not be 100% complementary to its target nucleic acid sequence to be specifically hybridizable. In preferred embodiments, an oligonucleotide is specifically hybridizable when binding of the oligonucleotide to the target sequence interferes with the normal function of the target sequence to cause a loss of utility or expression therefrom, and there is a sufficient degree of complementarity to avoid non-specific binding of the oligonucleotide to non-target sequences under conditions in which specific binding is desired, i.e., under physiological conditions in the case of in vivo assays or therapeutic treatment, or, in the case of in vitro assays, under conditions in which the assays are conducted. Thus, the oligonucleotide may include 1, 2, 3, or more base substitutions as compared to the region of a gene or mRNA sequence that it is targeting or to which it specifically hybridizes.

Generating siRNA Molecules siRNA can be provided in several forms including, e.g., as one or more isolated small-interfering RNA (siRNA) duplexes, as longer double-stranded RNA (dsRNA), or as siRNA or dsRNA transcribed from a transcriptional cassette in a DNA plasmid. In some embodiments, siRNA may be produced enzymatically or by partial/total organic synthesis, and modified ribonucleotides can be introduced by in vitro enzymatic or organic synthesis. In certain instances, each strand is prepared chemically. Methods of synthesizing RNA molecules are known in the art, e.g., the chemical synthesis methods as described in Verma and Eckstein (1998) or as described herein.

An RNA population can be used to provide long precursor RNAs, or long precursor RNAs that have substantial or complete identity to a selected target sequence can be used to make the siRNA. The RNAs can be isolated from cells or tissue, synthesized, and/or cloned according to methods well known to those of skill in the art. The RNA can be a mixed population (obtained from cells or tissue, transcribed from cDNA, subtracted, selected, etc.), or can represent a single target sequence. RNA can be naturally occurring (e.g., isolated from tissue or cell samples), synthesized in vitro (e.g., using T7 or SP6 polymerase and PCR products or a cloned cDNA), or chemically synthesized.

To form a long dsRNA, for synthetic RNAs, the complement is also transcribed in vitro and hybridized to form a dsRNA. If a naturally occurring RNA population is used, the RNA complements are also provided (e.g., to form dsRNA for digestion by *E. coli* RNAse III or Dicer), e.g., by transcribing cDNAs corresponding to the RNA population, or by using RNA polymerases. The precursor RNAs are then hybridized to form double stranded RNAs for digestion. The dsRNAs can be directly administered to a subject or can be digested in vitro prior to administration.

Methods for isolating RNA, synthesizing RNA, hybridizing nucleic acids, making and screening cDNA libraries, and performing PCR are well known in the art (see, e.g., Gubler and Hoffman, *Gene,* 25:263-269 (1983); Sambrook et al., supra; Ausubel et al., supra), as are PCR methods (see, U.S. Pat. Nos. 4,683,195 and 4,683,202; *PCR Protocols: A Guide to Methods and Applications* (Innis et al., eds, 1990)). Expression libraries are also well known to those of skill in the art. Additional basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994). The disclosures of these references are herein incorporated by reference in their entirety for all purposes.

Preferably, siRNA are chemically synthesized. The oligonucleotides that comprise the siRNA molecules of the invention can be synthesized using any of a variety of techniques known in the art, such as those described in Usman et al., *J. Am. Chem. Soc.,* 109:7845 (1987); Scaringe et al., *Nucl. Acids Res.,* 18:5433 (1990); Wincott et al., *Nucl. Acids Res.,* 23:2677-2684 (1995); and Wincott et al., *Meth. ods Mol. Bio.,* 74:59 (1997). The synthesis of oligonucleotides makes use of common nucleic acid protecting and coupling groups, such as dimethoxytrityl at the 5'-end and phosphoramidites at the 3'-end. As a non-limiting example, small scale syntheses can be conducted on an Applied Biosystems synthesizer using a 0.2 µmol scale protocol. Alternatively, syntheses at the 0.2 µmol scale can be performed on a 96-well plate synthesizer from Protogene (Palo Alto, Calif.). However, a larger or smaller scale of synthesis is also within the scope of this invention. Suitable reagents for oligonucleotide synthesis, methods for RNA deprotection, and methods for RNA purification are known to those of skill in the art.

siRNA molecules can also be synthesized via a tandem synthesis technique, wherein both strands are synthesized as a single continuous oligonucleotide fragment or strand separated by a cleavable linker that is subsequently cleaved to provide separate fragments or strands that hybridize to form the siRNA duplex. The linker can be a polynucleotide linker or a non-nucleotide linker. The tandem synthesis of siRNA can be readily adapted to both multiwell/multiplate synthesis platforms as well as large scale synthesis platforms employing batch reactors, synthesis columns, and the like. Alternatively, siRNA molecules can be assembled from two distinct oligonucleotides, wherein one oligonucleotide comprises the sense strand and the other comprises the antisense strand of the siRNA. For example, each strand can be synthesized separately and joined together by hybridization or ligation following synthesis and/or deprotection. In certain other instances, siRNA molecules can be synthesized as a single continuous oligonucleotide fragment, where the self-complementary sense and antisense regions hybridize to form an siRNA duplex having hairpin secondary structure.

In particular embodiments, siRNAs targeting MARV RNA (e.g., the siRNA molecules described in Table B) are administered using a carrier system such as a nucleic acid-lipid particle. In a preferred embodiment, the nucleic acid-lipid particle comprises: (a) one or more siRNA molecules targeting MARV; (b) a cationic lipid (e.g., DLinDMA, DLenDMA, DLin-K-C2-DMA, and/or γ-DLenDMA); and (c) a non-cationic lipid (e.g., DPPC, DSPC, DSPE, and/or cholesterol). In certain instances, the nucleic acid-lipid particle may further comprise a conjugated lipid that prevents aggregation of particles (e.g., PEG-DAA and/or POZ-DAA).

In addition to its utility in silencing the expression of any of the MARV genes (L, VP40, VP24, NP, VP35, GP and VP30), such as L, VP40, VP24 and NP, and in particular NP, for therapeutic purposes, the siRNA described herein are also useful in research and development applications as well as diagnostic, prophylactic, prognostic, clinical, and other healthcare applications. As a non-limiting example, the siRNA can be used in target validation studies directed at testing whether a specific member of the MARV gene family has the potential to be a therapeutic target.

Carrier Systems Containing Therapeutic Nucleic Acids
A. Lipid Particles

In certain aspects, the present invention provides lipid particles comprising one or more siRNA molecules (e.g., one or more siRNA molecules described in Table B) and one or more of cationic (amino) lipids or salts thereof. In some embodiments, the lipid particles of the invention further comprise one or more non-cationic lipids. In other embodiments, the lipid particles further comprise one or more conjugated lipids capable of reducing or inhibiting particle aggregation.

The lipid particles of the invention preferably comprise a siRNA (e.g., an siRNA molecules described in Table B), a cationic lipid, a non-cationic lipid, and a conjugated lipid that inhibits aggregation of particles. In some embodiments, the siRNA molecule is fully encapsulated within the lipid portion of the lipid particle such that the siRNA molecule in the lipid particle is resistant in aqueous solution to nuclease degradation. In other embodiments, the lipid particles described herein are substantially non-toxic to mammals such as humans. The lipid particles of the invention typically have a mean diameter of from about 30 nm to about 150 nm, from about 40 nm to about 150 nm, from about 50 nm to about 150 nm, from about 60 nm to about 130 nm, from about 70 nm to about 110 nm, or from about 70 to about 90 nm. In certain embodiments, the lipid particles of the invention have a median diameter of from about 30 nm to about 150 nm. The lipid particles of the invention also typically have a lipid:nucleic acid ratio (e.g., a lipid:siRNA ratio) (mass/mass ratio) of from about 1:1 to about 100:1, from about 1:1 to about 50:1, from about 2:1 to about 25:1, from about 3:1 to about 20:1, from about 5:1 to about 15:1, or from about 5:1 to about 10:1. In certain embodiments, the nucleic acid-lipid particle has a lipid:siRNA mass ratio of from about 5:1 to about 15:1.

In preferred embodiments, the lipid particles of the invention are serum-stable nucleic acid-lipid particles which comprise a siRNA molecule (e.g., a siRNA molecule as described in Table B), a cationic lipid (e.g., one or more cationic lipids of Formula I-III or salts thereof as set forth herein), a non-cationic lipid (e.g., mixtures of one or more phospholipids and cholesterol), and a conjugated lipid that inhibits aggregation of the particles (e.g., one or more PEG-lipid conjugates). The lipid particle may comprise at least 1, 2, 3, 4, 5, 6, 7, 8, 9, 10, or more unmodified and/or modified siRNA molecules that target one or more of the genes described herein. Nucleic acid-lipid particles and their method of preparation are described in, e.g., U.S. Pat. Nos. 5,753,613; 5,785,992; 5,705,385; 5,976,567; 5,981,501; 6,110,745; and 6,320,017; and PCT Publication No. WO 96/40964, the disclosures of which are each herein incorporated by reference in their entirety for all purposes.

In the nucleic acid-lipid particles of the invention, the siRNA molecule (e.g., an siRNA molecule as described in Table B) may be fully encapsulated within the lipid portion of the particle, thereby protecting the siRNA from nuclease degradation. In certain instances, the siRNA in the nucleic acid-lipid particle is not substantially degraded after exposure of the particle to a nuclease at 37° C. for at least about 20, 30, 45, or 60 minutes. In certain other instances, the siRNA in the nucleic acid-lipid particle is not substantially degraded after incubation of the particle in serum at 37° C. for at least about 30, 45, or 60 minutes or at least about 2, 3, 4, 5, 6, 7, 8, 9, 10, 12, 14, 16, 18, 20, 22, 24, 26, 28, 30, 32, 34, or 36 hours. In other embodiments, the siRNA is complexed with the lipid portion of the particle. One of the benefits of the formulations of the present invention is that the nucleic acid-lipid particle compositions are substantially non-toxic to mammals such as humans.

The term "fully encapsulated" indicates that the siRNA (e.g., a siRNA molecule as described in Table B) in the nucleic acid-lipid particle is not significantly degraded after exposure to serum or a nuclease assay that would significantly degrade free DNA or RNA. In a fully encapsulated system, preferably less than about 25% of the siRNA in the particle is degraded in a treatment that would normally degrade 100% of free siRNA, more preferably less than about 10%, and most preferably less than about 5% of the siRNA in the particle is degraded. "Fully encapsulated" also indicates that the nucleic acid-lipid particles are serum-stable, that is, that they do not rapidly decompose into their component parts upon in vivo administration.

In the context of nucleic acids, full encapsulation may be determined by performing a membrane-impermeable fluorescent dye exclusion assay, which uses a dye that has enhanced fluorescence when associated with nucleic acid. Specific dyes such as OliGreen® and RiboGreen® (Invitrogen Corp.; Carlsbad, Calif.) are available for the quantitative determination of plasmid DNA, single-stranded deoxyribonucleotides, and/or single- or double-stranded ribonucleotides. Encapsulation is determined by adding the dye to a liposomal formulation, measuring the resulting fluorescence, and comparing it to the fluorescence observed upon addition of a small amount of nonionic detergent. Detergent-mediated disruption of the liposomal bilayer releases the encapsulated nucleic acid, allowing it to interact with the membrane-impermeable dye. Nucleic acid encapsulation may be calculated as $E=(I_o-I)/I_o$, where I and $I_o$ refer to the fluorescence intensities before and after the addition of detergent (see, Wheeler et al., *Gene Ther.*, 6:271-281 (1999)).

In other embodiments, the present invention provides a nucleic acid-lipid particle composition comprising a plurality of nucleic acid-lipid particles.

In some instances, the nucleic acid-lipid particle composition comprises a siRNA molecule that is fully encapsulated within the lipid portion of the particles, such that from about 30% to about 100%, from about 40% to about 100%, from about 50% to about 100%, from about 60% to about 100%, from about 70% to about 100%, from about 80% to about 100%, from about 90% to about 100%, from about 30% to about 95%, from about 40% to about 95%, from about 50% to about 95%, from about 60% to about 95%, from about 70% to about 95%, from about 80% to about 95%, from about 85% to about 95%, from about 90% to about 95%, from about 30% to about 90%, from about 40% to about 90%, from about 50% to about 90%, from about 60% to about 90%, from about 70% to about 90%, from about 80% to about 90%, or at least about 30%, 35%, 40%, 45%, 50%, 55%, 60%, 65%, 70%, 75%, 80%, 85%, 90%, 91%, 92%, 93%, 94%, 95%, 96%, 97%, 98%, or 99% (or any fraction thereof or range therein) of the particles have the siRNA encapsulated therein.

In other instances, the nucleic acid-lipid particle composition comprises siRNA that is fully encapsulated within the lipid portion of the particles, such that from about 30% to about 100%, from about 40% to about 100%, from about 50% to about 100%, from about 60% to about 100%, from about 70% to about 100%, from about 80% to about 100%, from about 90% to about 100%, from about 30% to about 95%, from about 40% to about 95%, from about 50% to about 95%, from about 60% to about 95%, from about 70% to about 95%, from about 80% to about 95%, from about 85% to about 95%, from about 90% to about 95%, from about 30% to about 90%, from about 40% to about 90%, from about 50% to about 90%, from about 60% to about 90%, from about 70% to about 90%, from about 80% to about 90%, or at least about 30%, 35%, 40%, 45%, 50%, 55%, 60%, 65%, 70%, 75%, 80%, 85%, 90%, 91%, 92%, 93%, 94%, 95%, 96%, 97%, 98%, or 99% (or any fraction thereof or range therein) of the input siRNA is encapsulated in the particles.

Depending on the intended use of the lipid particles of the invention, the proportions of the components can be varied and the delivery efficiency of a particular formulation can be measured using, e.g., an endosomal release parameter (ERP) assay.

1. Cationic Lipids

Any of a variety of cationic lipids or salts thereof may be used in the lipid particles of the present invention either alone or in combination with one or more other cationic lipid species or non-cationic lipid species. The cationic lipids include the (R) and/or (S) enantiomers thereof.

In one aspect, cationic lipids of Formula I having the following structure are useful in the present invention:

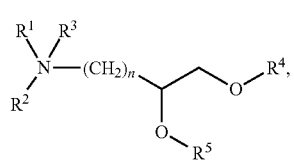

(I)

or salts thereof, wherein:

$R^1$ and $R^2$ are either the same or different and are independently hydrogen (H) or an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring of 4 to 6 carbon atoms and 1 or 2 heteroatoms selected from the group consisting of nitrogen (N), oxygen (O), and mixtures thereof;

$R^3$ is either absent or is hydrogen (H) or a $C_1$-$C_6$ alkyl to provide a quaternary amine;

$R^4$ and $R^5$ are either the same or different and are independently an optionally substituted $C_{10}$-$C_{24}$ alkyl, $C_{10}$-$C_{24}$ alkenyl, $C_{10}$-$C_{24}$ alkynyl, or $C_{10}$-$C_{24}$ acyl, wherein at least one of $R^4$ and $R^5$ comprises at least two sites of unsaturation; and n is 0, 1, 2, 3, or 4.

In some embodiments, $R^1$ and $R^2$ are independently an optionally substituted $C_1$-$C_4$ alkyl, $C_2$-$C_4$ alkenyl, or $C_2$-$C_4$ alkynyl. In one preferred embodiment, $R^1$ and $R^2$ are both methyl groups. In other preferred embodiments, n is 1 or 2. In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary amine. In further embodiments, $R^4$ and $R^5$ are independently an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl, wherein at least one of $R^4$ and $R^5$ comprises at least two sites of unsaturation.

In certain embodiments, $R^4$ and $R^5$ are independently selected from the group consisting of a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, an arachidonyl moiety, and a docosahexaenoyl moiety, as well as acyl derivatives thereof (e.g., linoleoyl, linolenoyl, γ-linolenoyl, etc.). In some instances, one of $R^4$ and $R^5$ comprises a branched alkyl group (e.g., a phytanyl moiety) or an acyl derivative thereof (e.g., a phytanoyl moiety). In certain instances, the octadecadienyl moiety is a linoleyl moiety. In certain other instances, the octadecatrienyl moiety is a linolenyl moiety or a γ-linolenyl moiety. In certain embodiments, $R^4$ and $R^5$ are both linoleyl moieties, linolenyl moieties, or γ-linolenyl moieties. In particular embodiments, the cationic lipid of Formula I is 1,2-dilinoleyloxy-N,N-dimethylaminopropane (DLinDMA), 1,2-dilinolenyloxy-N,N-dimethylaminopropane (DLenDMA), 1,2-dilinoleyloxy-(N,N-dimethyl)-butyl-4-amine (C2-DLinDMA), 1,2-dilinoleoyloxy-(N,N-dimethyl)-butyl-4-amine (C2-DLinDAP), or mixtures thereof.

In some embodiments, the cationic lipid of Formula I forms a salt (preferably a crystalline salt) with one or more anions. In one particular embodiment, the cationic lipid of Formula I is the oxalate (e.g., hemioxalate) salt thereof, which is preferably a crystalline salt.

The synthesis of cationic lipids such as DLinDMA and DLenDMA, as well as additional cationic lipids, is described in U.S. Patent Publication No. 20060083780, the disclosure of which is herein incorporated by reference in its entirety for all purposes. The synthesis of cationic lipids such as C2-DLinDMA and C2-DLinDAP, as well as additional cationic lipids, is described in international patent application number WO2011/000106 the disclosure of which is herein incorporated by reference in its entirety for all purposes.

In another aspect, cationic lipids of Formula II having the following structure (or salts thereof) are useful in the present invention:

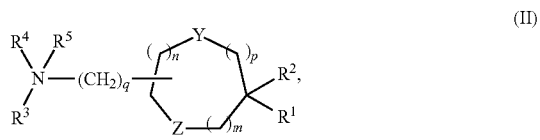

(II)

wherein $R^1$ and $R^2$ are either the same or different and are independently an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl; $R^3$ and $R^4$ are either the same or different and are independently an optionally substituted $C_1$-$C_6$ alkyl, $C_2$-$C_6$ alkenyl, or $C_2$-$C_6$ alkynyl, or $R^3$ and $R^4$ may join to form an optionally substituted heterocyclic ring of 4 to 6 carbon atoms and 1 or 2 heteroatoms chosen from nitrogen and oxygen; $R^5$ is either absent or is hydrogen (H) or a $C_1$-$C_6$ alkyl to provide a quaternary amine; m, n, and p are either the same or different and are independently either 0, 1, or 2, with the proviso that m, n, and p are not simultaneously 0; q is 0, 1, 2, 3, or 4; and Y and Z are either the same or different and are independently O, S, or NH. In a preferred embodiment, q is 2.

In some embodiments, the cationic lipid of Formula II is 2,2-dilinoleyl-4-(2-dimethylaminoethyl)-[1,3]-dioxolane (DLin-K-C2-DMA; "XTC2" or "C2K"), 2,2-dilinoleyl-4-(3-dimethylaminopropyl)-[1,3]-dioxolane (DLin-K-C3-DMA; "C3K"), 2,2-dilinoleyl-4-(4-dimethylaminobutyl)-[1,3]-dioxolane (DLin-K-C4-DMA; "C4K"), 2,2-dilinoleyl-5-dimethylaminomethyl-[1,3]-dioxane (DLin-K6-DMA), 2,2-dilinoleyl-4-N-methylpepiazino-[1,3]-dioxolane (DLin-K-MPZ), 2,2-dilinoleyl-4-dimethylaminomethyl-[1,3]-dioxolane (DLin-K-DMA), 2,2-dioleoyl-4-dimethylaminomethyl[1,3]-dioxolane (DO-K-DMA), 2,2-distearoyl-4-dimethylaminomethyl-[1,3]-dioxolane (DS-K-DMA), 2,2-dilinoleyl-4-N-morpholino-[1,3]-dioxolane (DLin-K-MA), 2,2-Dilinoleyl-4-trimethylamino-[1,3]-dioxolane chloride (DLin-K-TMA.C1), 2,2-dilinoleyl-4,5-bis(dimethylaminomethyl)-[1,3]-dioxolane (DLin-$K^2$-DMA), 2,2-dilinoleyl-4-methylpiperzine-[1,3]-dioxolane (D-Lin-K-N-methylpiperzine), or mixtures thereof. In preferred embodiments, the cationic lipid of Formula II is DLin-K-C2-DMA.

In some embodiments, the cationic lipid of Formula II forms a salt (preferably a crystalline salt) with one or more anions. In one particular embodiment, the cationic lipid of Formula II is the oxalate (e.g., hemioxalate) salt thereof, which is preferably a crystalline salt.

The synthesis of cationic lipids such as DLin-K-DMA, as well as additional cationic lipids, is described in PCT Publication No. WO 09/086558, the disclosure of which is herein incorporated by reference in its entirety for all purposes. The synthesis of cationic lipids such as DLin-K-C2-DMA, DLin-K-C3-DMA, DLin-K-C4-DMA, DLin-K6-DMA, DLin-K-MPZ, DO-K-DMA, DS-K-DMA, DLin-K-MA, DLin-K-TMA.C1, DLin-$K^2$-DMA, and D-Lin-K-N-methylpiperzine, as well as additional cationic lipids, is described in PCT Application No. PCT/US2009/060251, entitled "Improved Amino Lipids and Methods for the Delivery of Nucleic Acids," filed Oct. 9, 2009, the disclosure of which is incorporated herein by reference in its entirety for all purposes.

In a further aspect, cationic lipids of Formula III having the following structure are useful in the present invention:

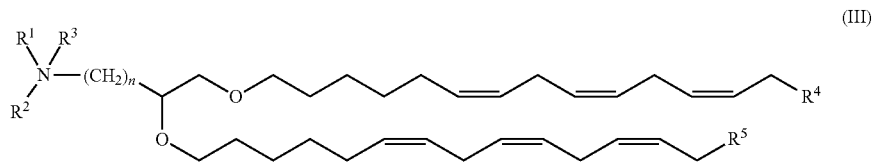

(III)

or salts thereof, wherein: $R^1$ and $R^2$ are either the same or different and are independently an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring of 4 to 6 carbon atoms and 1 or 2 heteroatoms selected from the group consisting of nitrogen (N), oxygen (O), and mixtures thereof; $R^3$ is either absent or is hydrogen (H) or a $C_1$-$C_6$ alkyl to provide a quaternary amine; $R^4$ and $R^5$ are either absent or present and when present are either the same or different and are independently an optionally substituted $C_1$-$C_{10}$ alkyl or $C_2$-$C_{10}$ alkenyl; and n is 0, 1, 2, 3, or 4.

In some embodiments, $R^1$ and $R^2$ are independently an optionally substituted $C_1$-$C_4$ alkyl, $C_2$-$C_4$ alkenyl, or $C_2$-$C_4$ alkynyl. In a preferred embodiment, $R^1$ and $R^2$ are both methyl groups. In another preferred embodiment, $R^4$ and $R^5$ are both butyl groups. In yet another preferred embodiment, n is 1. In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary amine. In further embodiments, $R^4$ and $R^5$ are independently an optionally substituted $C_2$-$C_6$ or $C_2$-$C_4$ alkyl or $C_2$-$C_6$ or $C_2$-$C_4$ alkenyl.

In an alternative embodiment, the cationic lipid of Formula III comprises ester linkages between the amino head group and one or both of the alkyl chains. In some embodiments, the cationic lipid of Formula III forms a salt (preferably a crystalline salt) with one or more anions. In one particular embodiment, the cationic lipid of Formula III is the oxalate (e.g., hemioxalate) salt thereof, which is preferably a crystalline salt.

Although each of the alkyl chains in Formula III contains cis double bonds at positions 6, 9, and 12 (i.e., cis,cis,cis-$\Delta^6, \Delta^9, \Delta^{12}$), in an alternative embodiment, one, two, or three of these double bonds in one or both alkyl chains may be in the trans configuration.

In a particularly preferred embodiment, the cationic lipid of Formula III has the structure:

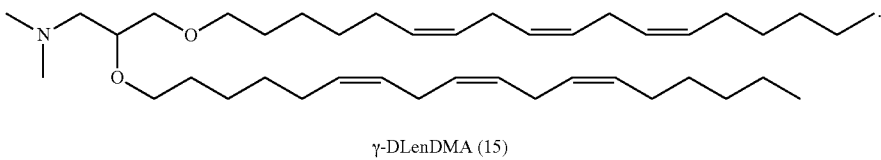 [SMILES: CCCCC/C=C\C/C=C\C/C=C\CCCCCOCC(CN(C)C)OCCCCC/C=C\C/C=C\C/C=C\CCCCC]

γ-DLenDMA (15)

The synthesis of cationic lipids such as γ-DLenDMA (15), as well as additional cationic lipids, is described in U.S. Provisional Application No. 61/222,462, entitled "Improved Cationic Lipids and Methods for the Delivery of Nucleic Acids," filed Jul. 1, 2009, the disclosure of which is herein incorporated by reference in its entirety for all purposes.

The synthesis of cationic lipids such as DLin-M-C3-DMA ("MC3"), as well as additional cationic lipids (e.g., certain analogs of MC3), is described in U.S. Provisional Application No. 61/185,800, entitled "Novel Lipids and Compositions for the Delivery of Therapeutics," filed Jun. 10, 2009, and U.S. Provisional Application No. 61/287,995, entitled "Methods and Compositions for Delivery of Nucleic Acids," filed Dec. 18, 2009, the disclosures of which are herein incorporated by reference in their entirety for all purposes.

Examples of other cationic lipids or salts thereof which may be included in the lipid particles of the present invention include, but are not limited to, cationic lipids such as those described in WO2011/000106, the disclosure of which is herein incorporated by reference in its entirety for all purposes, as well as cationic lipids such as N,N-dioleyl-N, N-dimethylammonium chloride (DODAC), 1,2-dioleyloxy-N,N-dimethylaminopropane (DODMA), 1,2-distearyloxy-N,N-dimethylaminopropane (DSDMA), N-(1-(2,3-dioleyloxy)propyl)-N,N,N-trimethylammonium chloride (DOTMA), N,N-distearyl-N,N-dimethylammonium bromide (DDAB), N-(1-(2,3-dioleoyloxy)propyl)-N,N,N-trimethylammonium chloride (DOTAP), 3-(N—(N',N'-dimethylaminoethane)-carbamoyl)cholesterol (DC-Chol), N-(1,2-dimyristyloxyprop-3-yl)-N,N-dimethyl-N-hydroxyethyl ammonium bromide (DMRIE), 2,3-dioleyloxy-N-[2(spermine-carboxamido)ethyl]-N,N-dimethyl-1-propanaminiumtrifluoroacetate (DOSPA), dioctadecylamidoglycyl spermine (DOGS), 3-dimethylamino-2-(cholest-5-en-3-beta-oxybutan-4-oxy)-1-(cis,cis-9,12-octadecadienoxy)propane (CLinDMA), 2-[5'-(cholest-5-en-3-beta-oxy)-3'-oxapentoxy)-3-dimethy-1-(cis,cis-9',1-2'-octadecadienoxy)propane (CpLinDMA), N,N-dimethyl-3,4-dioleyloxybenzylamine (DMOBA), 1,2-N,N'-dioleylcarbamyl-3-dimethylaminopropane (DOcarbDAP), 1,2-N,N'-dilinoleylcarbamyl-3-dimethylaminopropane (DLincarbDAP), 1,2-dilinoleylcarbamoyloxy-3-dimethylaminopropane (DLin-C-DAP), 1,2-dilinoleyoxy-3-(dimethylamino)acetoxypropane (DLin-DAC), 1,2-dilinoleyoxy-3-morpholinopropane (DLin-MA), 1,2-dilinoleoyl-3-dimethylaminopropane (DLinDAP), 1,2-dilinoleylthio-3-dimethylaminopropane (DLin-S-DMA), 1-linoleoyl-2-linoleyloxy-3-dimethylaminopropane (DLin-2-DMAP), 1,2-dilinoleyloxy-3-trimethylaminopropane chloride salt (DLin-TMA.Cl), 1,2-dilinoleoyl-3-trimethylaminopropane chloride salt (DLin-TAP.Cl), 1,2-dilinoleyloxy-3-(N-methylpiperazino)propane (DLin-MPZ), 3-(N,N-dilinoleylamino)-1,2-propanediol (DLinAP), 3-(N,N-dioleylamino)-1,2-propanedio (DOAP), 1,2-dilinoleyloxo-3-(2-N,N-dimethylamino)ethoxypropane (DLin-EG-DMA), 1,2-dioeylcarbamoyloxy-3-dimethylaminopropane (DO-C-DAP), 1,2-dimyristoleoyl-3-dimethylaminopropane (DM-DAP), 1,2-dioleoyl-3-trimethylaminopropane chloride (DOTAP.Cl), dilinoleylmethyl-3-dimethylaminopropionate (DLin-M-C2-DMA; also known as DLin-M-K-DMA or DLin-M-DMA), and mixtures thereof. Additional cationic lipids or salts thereof which may be included in the lipid particles of the present invention are described in U.S. Patent Publication No. 20090023673, the disclosure of which is herein incorporated by reference in its entirety for all purposes.

The synthesis of cationic lipids such as CLinDMA, as well as additional cationic lipids, is described in U.S. Patent Publication No. 20060240554, the disclosure of which is herein incorporated by reference in its entirety for all purposes. The synthesis of cationic lipids such as DLin-C-DAP, DLinDAC, DLinMA, DLinDAP, DLin-S-DMA, DLin-2-DMAP, DLinTMA.Cl, DLinTAP.Cl, DLinMPZ, DLinAP, DOAP, and DLin-EG-DMA, as well as additional cationic lipids, is described in PCT Publication No. WO 09/086558, the disclosure of which is herein incorporated by reference in its entirety for all purposes. The synthesis of cationic lipids such as DO-C-DAP, DMDAP, DOTAP.Cl, DLin-M-C2-DMA, as well as additional cationic lipids, is described in PCT Application No. PCT/US2009/060251, entitled "Improved Amino Lipids and Methods for the Delivery of Nucleic Acids," filed Oct. 9, 2009, the disclosure of which is incorporated herein by reference in its entirety for all purposes. The synthesis of a number of other cationic lipids and related analogs has been described in U.S. Pat. Nos. 5,208,036; 5,264,618; 5,279,833; 5,283,185; 5,753,613; and 5,785,992; and PCT Publication No. WO 96/10390, the disclosures of which are each herein incorporated by reference in their entirety for all purposes. Additionally, a number of commercial preparations of cationic lipids can be used, such as, e.g., LIPOFECTIN® (including DOTMA and DOPE, available from Invitrogen); LIPOFECTAMINE® (including DOSPA and DOPE, available from Invitrogen); and TRANSFECTAM® (including DOGS, available from Promega Corp.).

In some embodiments, the cationic lipid comprises from about 50 mol % to about 90 mol %, from about 50 mol % to about 85 mol %, from about 50 mol % to about 80 mol %, from about 50 mol % to about 75 mol %, from about 50 mol % to about 70 mol %, from about 50 mol % to about 65 mol %, from about 50 mol % to about 60 mol %, from about 55 mol % to about 65 mol %, or from about 55 mol % to about 70 mol % (or any fraction thereof or range therein) of the total lipid present in the particle. In particular embodiments, the cationic lipid comprises about 50 mol %, 51 mol %, 52 mol %, 53 mol %, 54 mol %, 55 mol %, 56 mol %, 57 mol %, 58 mol %, 59 mol %, 60 mol %, 61 mol %, 62 mol %, 63 mol %, 64 mol %, or 65 mol % (or any fraction thereof) of the total lipid present in the particle.

In other embodiments, the cationic lipid comprises from about 2 mol % to about 60 mol %, from about 5 mol % to about 50 mol %, from about 10 mol % to about 50 mol %, from about 20 mol % to about 50 mol %, from about 20 mol % to about 40 mol %, from about 30 mol % to about 40 mol %, or about 40 mol % (or any fraction thereof or range therein) of the total lipid present in the particle.

Additional percentages and ranges of cationic lipids suitable for use in the lipid particles of the present invention are described in PCT Publication No. WO 09/127060, U.S. Published Application No. US 2011/0071208, PCT Publication No. WO2011/000106, and U.S. Published Application No. US 2011/0076335, the disclosures of which are herein incorporated by reference in their entirety for all purposes.

It should be understood that the percentage of cationic lipid present in the lipid particles of the invention is a target amount, and that the actual amount of cationic lipid present in the formulation may vary, for example, by ±5 mol %. For example, in one exemplary lipid particle formulation, the target amount of cationic lipid is 57.1 mol %, but the actual amount of cationic lipid may be ±5 mol %, ±4 mol %, ±3 mol %, ±2 mol %, ±1 mol %, ±0.75 mol %, ±0.5 mol %, ±0.25 mol %, or ±0.1 mol % of that target amount, with the balance of the formulation being made up of other lipid components (adding up to 100 mol % of total lipids present in the particle).

Further examples of cationic lipids useful for inclusion in lipid particles used in the present invention are shown below:

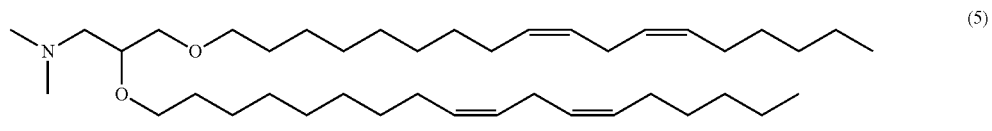

N,N-dimethyl-2,3-bis((9Z,12Z)-octadeca-9,12-dienyloxy)propan-1-amine (5)

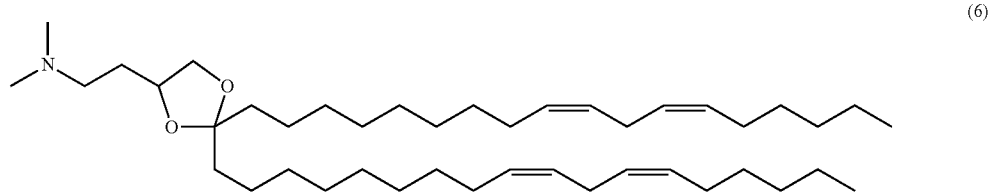

2-(2,2-di((9Z,12Z)-octadeca-9,12-dienyl)-1,3-dioxolan-4-yl)-N,N-dimethylethanamine (6)

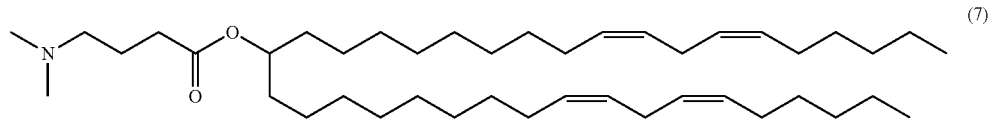

(6Z,9Z,28Z,31Z)-heptatriaconta-6,9,28,31-tetraen-19-yl 4-(dimethylamino)butanoate (7)

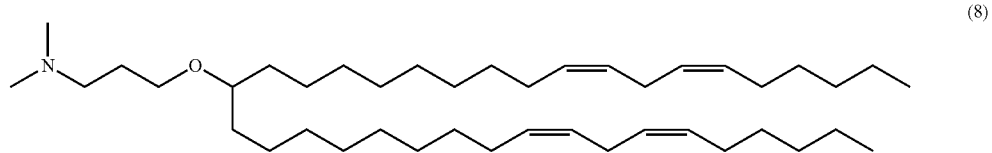

3-((6Z,9Z,28Z,31Z)-heptatriaconta-6,9,28,31-tetraen-19-yloxy)-N,N-dimethylpropan-1-amine (8)

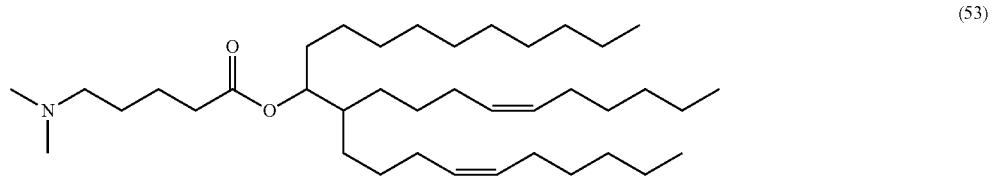

(Z)-12-((Z)-dec-4-enyl)docos-16-en-11-yl 5-(dimethylamino)pentanoate (53)

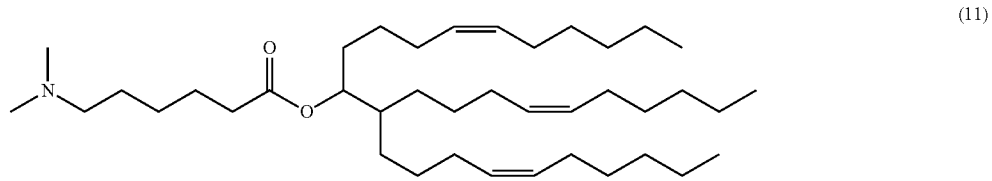

(6Z,16Z)-12-((Z)-dec-4-enyl)docosa-6,16-dien-11-yl 6-(dimethylamino)hexanoate (11)

-continued

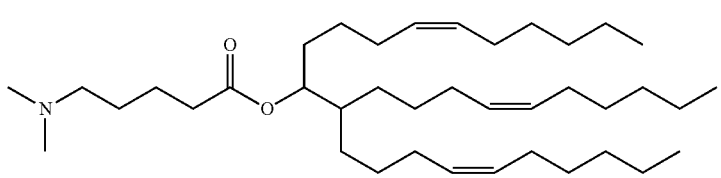

(6Z,16Z)-12-((Z)-dec-4-enyl)docosa-6,16-dien-11-yl 5-(dimethylamino)pentanoate (13)

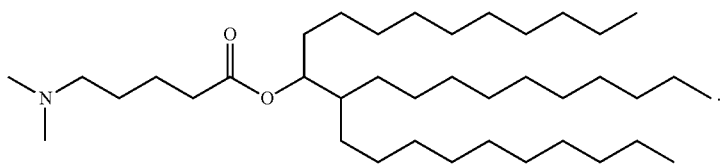

12-decyldocosan-11-yl 5-(dimethylamino)pentanoate (14)

2. Non-Cationic Lipids

The non-cationic lipids used in the lipid particles of the invention can be any of a variety of neutral uncharged, zwitterionic, or anionic lipids capable of producing a stable complex.

Non-limiting examples of non-cationic lipids include phospholipids such as lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoyl-phosphatidylcholine (POPC), palmitoyloleoyl-phosphatidylethanolamine (POPE), palmitoyloleoyl-phosphatidylglycerol (POPG), dioleoylphosphatidylethanolamine 4-(N-maleimidomethyl)-cyclohexane-1-carboxylate (DOPE-mal), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), lysophosphatidylcholine, dilinoleoylphosphatidylcholine, and mixtures thereof. Other diacylphosphatidylcholine and diacylphosphatidylethanolamine phospholipids can also be used. The acyl groups in these lipids are preferably acyl groups derived from fatty acids having $C_{10}$-$C_{24}$ carbon chains, e.g., lauroyl, myristoyl, palmitoyl, stearoyl, or oleoyl.

Additional examples of non-cationic lipids include sterols such as cholesterol and derivatives thereof. Non-limiting examples of cholesterol derivatives include polar analogues such as 5α-cholestanol, 5β-coprostanol, cholesteryl-(2'-hydroxy-ethyl ether, cholesteryl-(4'-hydroxy)-butyl ether, and 6-ketocholestanol; non-polar analogues such as 5α-cholestane, cholestenone, 5α-cholestanone, 5β-cholestanone, and cholesteryl decanoate; and mixtures thereof. In preferred embodiments, the cholesterol derivative is a polar analogue such as cholesteryl-(4'-hydroxy)-butyl ether. The synthesis of cholesteryl-(2'-hydroxy)-ethyl ether is described in PCT Publication No. WO 09/127060, the disclosure of which is herein incorporated by reference in its entirety for all purposes.

In some embodiments, the non-cationic lipid present in the lipid particles comprises or consists of a mixture of one or more phospholipids and cholesterol or a derivative thereof. In other embodiments, the non-cationic lipid present in the lipid particles comprises or consists of one or more phospholipids, e.g., a cholesterol-free lipid particle formulation. In yet other embodiments, the non-cationic lipid present in the lipid particles comprises or consists of cholesterol or a derivative thereof, e.g., a phospholipid-free lipid particle formulation.

Other examples of non-cationic lipids suitable for use in the present invention include nonphosphorous containing lipids such as, e.g., stearylamine, dodecylamine, hexadecylamine, acetyl palmitate, glycerolricinoleate, hexadecyl stereate, isopropyl myristate, amphoteric acrylic polymers, triethanolamine-lauryl sulfate, alkyl-aryl sulfate polyethyloxylated fatty acid amides, dioctadecyldimethyl ammonium bromide, ceramide, sphingomyelin, and the like.

In some embodiments, the non-cationic lipid comprises from about 10 mol % to about 60 mol %, from about 20 mol % to about 55 mol %, from about 20 mol % to about 45 mol %, from about 20 mol % to about 40 mol %, from about 25 mol % to about 50 mol %, from about 25 mol % to about 45 mol %, from about 30 mol % to about 50 mol %, from about 30 mol % to about 45 mol %, from about 30 mol % to about 40 mol %, from about 35 mol % to about 45 mol %, from about 37 mol % to about 42 mol %, or about 35 mol %, 36 mol %, 37 mol %, 38 mol %, 39 mol %, 40 mol %, 41 mol %, 42 mol %, 43 mol %, 44 mol %, or 45 mol % (or any fraction thereof or range therein) of the total lipid present in the particle.

In embodiments where the lipid particles contain a mixture of phospholipid and cholesterol or a cholesterol derivative, the mixture may comprise up to about 40 mol %, 45 mol %, 50 mol %, 55 mol %, or 60 mol % of the total lipid present in the particle.

In some embodiments, the phospholipid component in the mixture may comprise from about 2 mol % to about 20 mol %, from about 2 mol % to about 15 mol %, from about 2 mol % to about 12 mol %, from about 4 mol % to about 15 mol %, or from about 4 mol % to about 10 mol % (or any fraction thereof or range therein) of the total lipid present in the particle. In certain preferred embodiments, the phospholipid component in the mixture comprises from about 5 mol % to about 10 mol %, from about 5 mol % to about 9 mol %, from about 5 mol % to about 8 mol %, from about 6 mol % to about 9 mol %, from about 6 mol % to about 8 mol %, or about 5 mol %, 6 mol %, 7 mol %, 8 mol %, 9 mol %, or 10 mol % (or any fraction thereof or range therein) of the total lipid present in the particle. As a non-limiting example, a lipid particle formulation comprising a mixture of phospholipid and cholesterol may comprise a phospholipid such as DPPC or DSPC at about 7 mol % (or any fraction thereof), e.g., in a mixture with cholesterol or a cholesterol derivative at about 34 mol % (or any fraction thereof) of the total lipid present in the particle. As another non-limiting example, a lipid particle formulation comprising a mixture of phospholipid and cholesterol may comprise a phospholipid such as DPPC or DSPC at about 7 mol % (or any fraction thereof), e.g., in a mixture with cholesterol or a cholesterol derivative at about 32 mol % (or any fraction thereof) of the total lipid present in the particle.

By way of further example, a lipid formulation useful in the practice of the invention has a lipid to drug (e.g., siRNA) ratio of about 10:1 (e.g., a lipid:drug ratio of from 9.5:1 to 11:1, or from 9.9:1 to 11:1, or from 10:1 to 10.9:1). Exemplary lipid formulations of this aspect of the invention include the following components (wherein the percentage values of the components are mole percent): PEG-lipid (1.6%), cationic lipid (54.6%), phospholipid (10.9%), cholesterol (32.8%). For example, in one representative embodiment, the PEG-lipid is PEG-C-DMA (1.6%), the cationic lipid is 1B-11 (54.6%), the phospholipid is DSPC (10.9%), and cholesterol is present at 32.8%.

In other embodiments, the cholesterol component in the mixture may comprise from about 25 mol % to about 45 mol %, from about 25 mol % to about 40 mol %, from about 30 mol % to about 45 mol %, from about 30 mol % to about 40 mol %, from about 27 mol % to about 37 mol %, from about 25 mol % to about 30 mol %, or from about 35 mol % to about 40 mol % (or any fraction thereof or range therein) of the total lipid present in the particle. In certain preferred embodiments, the cholesterol component in the mixture comprises from about 25 mol % to about 35 mol %, from about 27 mol % to about 35 mol %, from about 29 mol % to about 35 mol %, from about 30 mol % to about 35 mol %, from about 30 mol % to about 34 mol %, from about 31 mol % to about 33 mol %, or about 30 mol %, 31 mol %, 32 mol %, 33 mol %, 34 mol %, or 35 mol % (or any fraction thereof or range therein) of the total lipid present in the particle.

In embodiments where the lipid particles are phospholipid-free, the cholesterol or derivative thereof may comprise up to about 25 mol %, 30 mol %, 35 mol %, 40 mol %, 45 mol %, 50 mol %, 55 mol %, or 60 mol % of the total lipid present in the particle.

In some embodiments, the cholesterol or derivative thereof in the phospholipid-free lipid particle formulation may comprise from about 25 mol % to about 45 mol %, from about 25 mol % to about 40 mol %, from about 30 mol % to about 45 mol %, from about 30 mol % to about 40 mol %, from about 31 mol % to about 39 mol %, from about 32 mol % to about 38 mol %, from about 33 mol % to about 37 mol %, from about 35 mol % to about 45 mol %, from about 30 mol % to about 35 mol %, from about 35 mol % to about 40 mol %, or about 30 mol %, 31 mol %, 32 mol %, 33 mol %, 34 mol %, 35 mol %, 36 mol %, 37 mol %, 38 mol %, 39 mol %, or 40 mol % (or any fraction thereof or range therein) of the total lipid present in the particle. As a non-limiting example, a lipid particle formulation may comprise cholesterol at about 37 mol % (or any fraction thereof) of the total lipid present in the particle. As another non-limiting example, a lipid particle formulation may comprise cholesterol at about 35 mol % (or any fraction thereof) of the total lipid present in the particle.

In other embodiments, the non-cationic lipid comprises from about 5 mol % to about 90 mol %, from about 10 mol % to about 85 mol %, from about 20 mol % to about 80 mol %, about 10 mol % (e.g., phospholipid only), or about 60 mol % (e.g., phospholipid and cholesterol or derivative thereof) (or any fraction thereof or range therein) of the total lipid present in the particle.

Additional percentages and ranges of non-cationic lipids suitable for use in the lipid particles of the present invention are described in PCT Publication No. WO 09/127060, U.S. Published Application No. US 2011/0071208, PCT Publication No. WO2011/000106, and U.S. Published Application No. US 2011/0076335, the disclosures of which are herein incorporated by reference in their entirety for all purposes.

It should be understood that the percentage of non-cationic lipid present in the lipid particles of the invention is a target amount, and that the actual amount of non-cationic lipid present in the formulation may vary, for example, by ±5 mol %.

3. Lipid Conjugates

In addition to cationic and non-cationic lipids, the lipid particles of the invention may further comprise a lipid conjugate. The conjugated lipid is useful in that it prevents the aggregation of particles. Suitable conjugated lipids include, but are not limited to, PEG-lipid conjugates, POZ-lipid conjugates, ATTA-lipid conjugates, cationic-polymer-lipid conjugates (CPLs), and mixtures thereof. In certain embodiments, the particles comprise either a PEG-lipid conjugate or an ATTA-lipid conjugate together with a CPL.

In a preferred embodiment, the lipid conjugate is a PEG-lipid. Examples of PEG-lipids include, but are not limited to, PEG coupled to dialkyloxypropyls (PEG-DAA) as described in, e.g., PCT Publication No. WO 05/026372, PEG coupled to diacylglycerol (PEG-DAG) as described in, e.g., U.S. Patent Publication Nos. 20030077829 and 2005008689, PEG coupled to phospholipids such as phosphatidylethanolamine (PEG-PE), PEG conjugated to ceramides as described in, e.g., U.S. Pat. No. 5,885,613, PEG conjugated to cholesterol or a derivative thereof, and mixtures thereof. The disclosures of these patent documents are herein incorporated by reference in their entirety for all purposes.

Additional PEG-lipids suitable for use in the invention include, without limitation, mPEG2000-1,2-di-O-alkyl-sn3-carbomoylglyceride (PEG-C-DOMG). The synthesis of PEG-C-DOMG is described in PCT Publication No. WO 09/086558, the disclosure of which is herein incorporated by reference in its entirety for all purposes. Yet additional suitable PEG-lipid conjugates include, without limitation, 1-[8'-(1,2-dimyristoyl-3-propanoxy)-carboxamido-3',6'-dioxaoctanyl]carbamoyl-co-methyl-poly(ethylene glycol) (2KPEG-DMG). The synthesis of 2KPEG-DMG is described in U.S. Pat. No. 7,404,969, the disclosure of which is herein incorporated by reference in its entirety for all purposes.

PEG is a linear, water-soluble polymer of ethylene PEG repeating units with two terminal hydroxyl groups. PEGs are classified by their molecular weights; for example, PEG 2000 has an average molecular weight of about 2,000 daltons, and PEG 5000 has an average molecular weight of about 5,000 daltons. PEGs are commercially available from Sigma Chemical Co. and other companies and include, but are not limited to, the following: monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycol-amine (MePEG-NH$_2$), monomethoxypolyethylene glycol-tresylate (MePEG-TRES), monomethoxypolyethylene glycol-imidazolyl-carbonyl (MePEG-IM), as well as such compounds containing a terminal hydroxyl group instead of a terminal methoxy group (e.g., HO-PEG-S, HO-PEG-S-NHS, HO-PEG-NH$_2$, etc.). Other PEGs such as those described in U.S. Pat. Nos. 6,774,180 and 7,053,150 (e.g., mPEG (20 KDa) amine) are also useful for preparing the PEG-lipid conjugates of the present invention. The disclosures of these patents are herein incorporated by reference in their entirety for all purposes. In addition, monomethoxypolyethyleneglycol-acetic acid (MePEG-CH$_2$COOH) is particularly useful for preparing PEG-lipid conjugates including, e.g., PEG-DAA conjugates.

The PEG moiety of the PEG-lipid conjugates described herein may comprise an average molecular weight ranging from about 550 daltons to about 10,000 daltons. In certain instances, the PEG moiety has an average molecular weight of from about 750 daltons to about 5,000 daltons (e.g., from about 1,000 daltons to about 5,000 daltons, from about 1,500 daltons to about 3,000 daltons, from about 750 daltons to about 3,000 daltons, from about 750 daltons to about 2,000 daltons, etc.). In preferred embodiments, the PEG moiety has an average molecular weight of about 2,000 daltons or about 750 daltons.

In certain instances, the PEG can be optionally substituted by an alkyl, alkoxy, acyl, or aryl group. The PEG can be conjugated directly to the lipid or may be linked to the lipid via a linker moiety. Any linker moiety suitable for coupling the PEG to a lipid can be used including, e.g., non-ester containing linker moieties and ester-containing linker moieties. In a preferred embodiment, the linker moiety is a non-ester containing linker moiety. As used herein, the term "non-ester containing linker moiety" refers to a linker moiety that does not contain a carboxylic ester bond (—OC(O)—). Suitable non-ester containing linker moieties include, but are not limited to, amido (—C(O)NH—), amino (—NR—), carbonyl (—C(O)—), carbamate (—NHC(O)O—), urea (—NHC(O)NH—), disulphide (—S—S—), ether (—O—), succinyl (—(O)CCH$_2$CH$_2$C(O)—), succinamidyl (—NHC(O)CH$_2$CH$_2$C(O)NH—), ether, disulphide, as well as combinations thereof (such as a linker containing both a carbamate linker moiety and an amido linker moiety). In a preferred embodiment, a carbamate linker is used to couple the PEG to the lipid.

In other embodiments, an ester containing linker moiety is used to couple the PEG to the lipid. Suitable ester containing linker moieties include, e.g., carbonate (—OC(O)O—), succinoyl, phosphate esters (—O—(O)POH—O—), sulfonate esters, and combinations thereof.

Phosphatidylethanolamines having a variety of acyl chain groups of varying chain lengths and degrees of saturation can be conjugated to PEG to form the lipid conjugate. Such phosphatidylethanolamines are commercially available, or can be isolated or synthesized using conventional techniques known to those of skill in the art. Phosphatidyl-ethanolamines containing saturated or unsaturated fatty acids with carbon chain lengths in the range of C$_{10}$ to C$_{20}$ are preferred. Phosphatidylethanolamines with mono- or diunsaturated fatty acids and mixtures of saturated and unsaturated fatty acids can also be used. Suitable phosphatidylethanolamines include, but are not limited to, dimyristoyl-phosphatidylethanolamine (DMPE), dipalmitoyl-phosphatidylethanolamine (DPPE), dioleoylphosphatidylethanolamine (DOPE), and distearoyl-phosphatidylethanolamine (DSPE).

The term "ATTA" or "polyamide" includes, without limitation, compounds described in U.S. Pat. Nos. 6,320,017 and 6,586,559, the disclosures of which are herein incorporated by reference in their entirety for all purposes. These compounds include a compound having the formula:

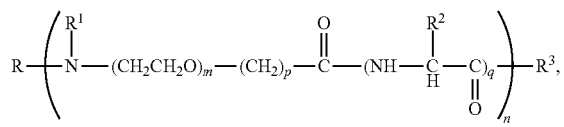

(IV)

wherein R is a member selected from the group consisting of hydrogen, alkyl and acyl; R$^1$ is a member selected from the group consisting of hydrogen and alkyl; or optionally, R and R$^1$ and the nitrogen to which they are bound form an azido moiety; R$^2$ is a member of the group selected from hydrogen, optionally substituted alkyl, optionally substituted aryl and a side chain of an amino acid; R$^3$ is a member selected from the group consisting of hydrogen, halogen, hydroxy, alkoxy, mercapto, hydrazino, amino and NR$^4$R$^5$, wherein R$^4$ and R$^5$ are independently hydrogen or alkyl; n is 4 to 80; m is 2 to 6; p is 1 to 4; and q is 0 or 1. It will be apparent to those of skill in the art that other polyamides can be used in the compounds of the present invention.

The term "diacylglycerol" or "DAG" includes a compound having 2 fatty acyl chains, R$^1$ and R$^2$, both of which have independently between 2 and 30 carbons bonded to the 1- and 2-position of glycerol by ester linkages. The acyl groups can be saturated or have varying degrees of unsaturation. Suitable acyl groups include, but are not limited to, lauroyl (C$_{12}$), myristoyl (C$_{14}$), palmitoyl (C$_{16}$), stearoyl (C$_{18}$), and icosoyl (C$_{20}$). In preferred embodiments, R$^1$ and R$^2$ are the same, i.e., R$^1$ and R$^2$ are both myristoyl (i.e., dimyristoyl), R$^1$ and R$^2$ are both stearoyl (i.e., distearoyl), etc. Diacylglycerols have the following general formula:

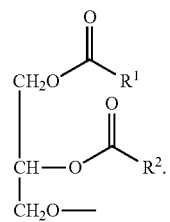

(V)

The term "dialkyloxypropyl" or "DAA" includes a compound having 2 alkyl chains, $R^1$ and $R^2$, both of which have independently between 2 and 30 carbons. The alkyl groups can be saturated or have varying degrees of unsaturation. Dialkyloxypropyls have the following general formula:

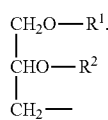

(VI)

In a preferred embodiment, the PEG-lipid is a PEG-DAA conjugate having the following formula:

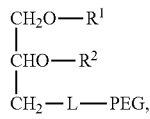

(VII)

wherein $R^1$ and $R^2$ are independently selected and are long-chain alkyl groups having from about 10 to about 22 carbon atoms; PEG is a polyethyleneglycol; and L is a non-ester containing linker moiety or an ester containing linker moiety as described above. The long-chain alkyl groups can be saturated or unsaturated. Suitable alkyl groups include, but are not limited to, decyl ($C_{10}$), lauryl ($C_{12}$), myristyl ($C_{14}$), palmityl ($C_{16}$), stearyl ($C_{18}$), and icosyl ($C_{20}$). In preferred embodiments, $R^1$ and $R^2$ are the same, i.e., $R^1$ and $R^2$ are both myristyl (i.e., dimyristyl), $R^1$ and $R^2$ are both stearyl (i.e., distearyl), etc.

In Formula VII above, the PEG has an average molecular weight ranging from about 550 daltons to about 10,000 daltons. In certain instances, the PEG has an average molecular weight of from about 750 daltons to about 5,000 daltons (e.g., from about 1,000 daltons to about 5,000 daltons, from about 1,500 daltons to about 3,000 daltons, from about 750 daltons to about 3,000 daltons, from about 750 daltons to about 2,000 daltons, etc.). In preferred embodiments, the PEG has an average molecular weight of about 2,000 daltons or about 750 daltons. The PEG can be optionally substituted with alkyl, alkoxy, acyl, or aryl groups. In certain embodiments, the terminal hydroxyl group is substituted with a methoxy or methyl group.

In a preferred embodiment, "L" is a non-ester containing linker moiety. Suitable non-ester containing linkers include, but are not limited to, an amido linker moiety, an amino linker moiety, a carbonyl linker moiety, a carbamate linker moiety, a urea linker moiety, an ether linker moiety, a disulphide linker moiety, a succinamidyl linker moiety, and combinations thereof. In a preferred embodiment, the non-ester containing linker moiety is a carbamate linker moiety (i.e., a PEG-C-DAA conjugate). In another preferred embodiment, the non-ester containing linker moiety is an amido linker moiety (i.e., a PEG-A-DAA conjugate). In yet another preferred embodiment, the non-ester containing linker moiety is a succinamidyl linker moiety (i.e., a PEG-S-DAA conjugate).

In particular embodiments, the PEG-lipid conjugate is selected from:

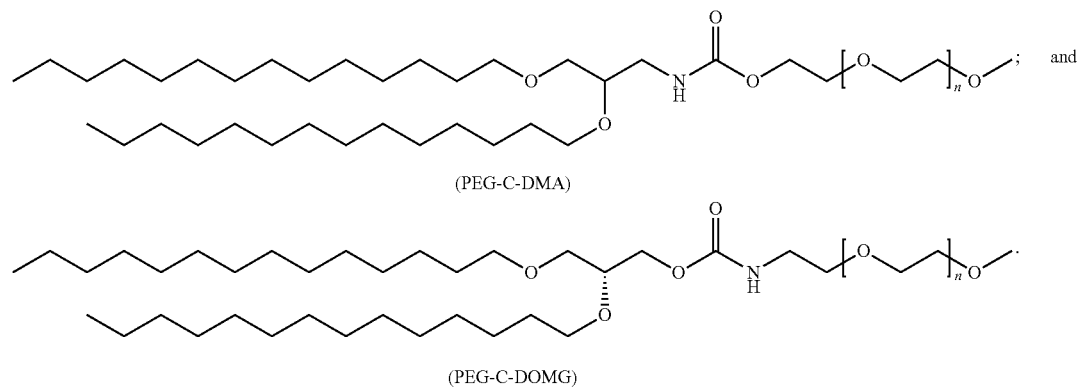

(PEG-C-DMA)

(PEG-C-DOMG)

The PEG-DAA conjugates are synthesized using standard techniques and reagents known to those of skill in the art. It will be recognized that the PEG-DAA conjugates will contain various amide, amine, ether, thio, carbamate, and urea linkages. Those of skill in the art will recognize that methods and reagents for forming these bonds are well known and readily available. See, e.g., March, ADVANCED ORGANIC CHEMISTRY (Wiley 1992); Larock, COMPREHENSIVE ORGANIC TRANSFORMATIONS (VCH 1989); and Furniss, VOGEL'S TEXTBOOK OF PRACTICAL ORGANIC CHEMISTRY, 5th ed. (Longman 1989). It will also be appreciated that any functional groups present may require protection and deprotection at different points in the synthesis of the PEG-DAA conjugates. Those of skill in the art will recognize that such techniques are well known. See, e.g., Green and Wuts, PROTECTIVE GROUPS IN ORGANIC SYNTHESIS (Wiley 1991).

Preferably, the PEG-DAA conjugate is a PEG-didecyloxypropyl ($C_{10}$) conjugate, a PEG-dilauryloxypropyl ($C_{12}$) conjugate, a PEG-dimyristyloxypropyl ($C_{14}$) conjugate, a PEG-dipalmityloxypropyl ($C_{16}$) conjugate, or a PEG-distearyloxypropyl ($C_{18}$) conjugate. In these embodiments, the PEG preferably has an average molecular weight of about 750 or about 2,000 daltons. In one particularly preferred embodiment, the PEG-lipid conjugate comprises PEG2000-C-DMA, wherein the "2000" denotes the average molecular weight of the PEG, the "C" denotes a carbamate linker moiety, and the "DMA" denotes dimyristyloxypropyl. In another particularly preferred embodiment, the PEG-lipid conjugate comprises PEG750-C-DMA, wherein the "750" denotes the average molecular weight of the PEG, the "C"

denotes a carbamate linker moiety, and the "DMA" denotes dimyristyloxypropyl. In particular embodiments, the terminal hydroxyl group of the PEG is substituted with a methyl group. Those of skill in the art will readily appreciate that other dialkyloxypropyls can be used in the PEG-DAA conjugates of the present invention.

In addition to the foregoing, it will be readily apparent to those of skill in the art that other hydrophilic polymers can be used in place of PEG. Examples of suitable polymers that can be used in place of PEG include, but are not limited to, polyvinylpyrrolidone, polymethyloxazoline, polyethyloxazoline, polyhydroxypropyl methacrylamide, polymethacrylamide and polydimethylacrylamide, polylactic acid, polyglycolic acid, and derivatized celluloses such as hydroxymethylcellulose or hydroxyethylcellulose.

In addition to the foregoing components, the lipid particles of the present invention can further comprise cationic poly(ethylene glycol) (PEG) lipids or CPLs (see, e.g., Chen et al., Bioconj. Chem., 11:433-437 (2000); U.S. Pat. No. 6,852,334; PCT Publication No. WO 00/62813, the disclosures of which are herein incorporated by reference in their entirety for all purposes).

Suitable CPLs include compounds of Formula VIII:

A-W-Y (VIII), wherein A, W, and Y are as described below.

With reference to Formula VIII, "A" is a lipid moiety such as an amphipathic lipid, a neutral lipid, or a hydrophobic lipid that acts as a lipid anchor. Suitable lipid examples include, but are not limited to, diacylglycerolyls, dialkylglycerolyls, N—N-dialkylaminos, 1,2-diacyloxy-3-aminopropanes, and 1,2-dialkyl-3-aminopropanes.

"W" is a polymer or an oligomer such as a hydrophilic polymer or oligomer. Preferably, the hydrophilic polymer is a biocompatible polymer that is nonimmunogenic or possesses low inherent immunogenicity. Alternatively, the hydrophilic polymer can be weakly antigenic if used with appropriate adjuvants. Suitable nonimmunogenic polymers include, but are not limited to, PEG, polyamides, polylactic acid, polyglycolic acid, polylactic acid/polyglycolic acid copolymers, and combinations thereof. In a preferred embodiment, the polymer has a molecular weight of from about 250 to about 7,000 daltons.

"Y" is a polycationic moiety. The term polycationic moiety refers to a compound, derivative, or functional group having a positive charge, preferably at least 2 positive charges at a selected pH, preferably physiological pH. Suitable polycationic moieties include basic amino acids and their derivatives such as arginine, asparagine, glutamine, lysine, and histidine; spermine; spermidine; cationic dendrimers; polyamines; polyamine sugars; and amino polysaccharides. The polycationic moieties can be linear, such as linear tetralysine, branched or dendrimeric in structure. Polycationic moieties have between about 2 to about 15 positive charges, preferably between about 2 to about 12 positive charges, and more preferably between about 2 to about 8 positive charges at selected pH values. The selection of which polycationic moiety to employ may be determined by the type of particle application which is desired.

The charges on the polycationic moieties can be either distributed around the entire particle moiety, or alternatively, they can be a discrete concentration of charge density in one particular area of the particle moiety e.g., a charge spike. If the charge density is distributed on the particle, the charge density can be equally distributed or unequally distributed. All variations of charge distribution of the polycationic moiety are encompassed by the present invention.

The lipid "A" and the nonimmunogenic polymer "W" can be attached by various methods and preferably by covalent attachment. Methods known to those of skill in the art can be used for the covalent attachment of "A" and "W." Suitable linkages include, but are not limited to, amide, amine, carboxyl, carbonate, carbamate, ester, and hydrazone linkages. It will be apparent to those skilled in the art that "A" and "W" must have complementary functional groups to effectuate the linkage. The reaction of these two groups, one on the lipid and the other on the polymer, will provide the desired linkage. For example, when the lipid is a diacylglycerol and the terminal hydroxyl is activated, for instance with NHS and DCC, to form an active ester, and is then reacted with a polymer which contains an amino group, such as with a polyamide (see, e.g., U.S. Pat. Nos. 6,320,017 and 6,586,559, the disclosures of which are herein incorporated by reference in their entirety for all purposes), an amide bond will form between the two groups.

In certain instances, the polycationic moiety can have a ligand attached, such as a targeting ligand or a chelating moiety for complexing calcium. Preferably, after the ligand is attached, the cationic moiety maintains a positive charge. In certain instances, the ligand that is attached has a positive charge. Suitable ligands include, but are not limited to, a compound or device with a reactive functional group and include lipids, amphipathic lipids, carrier compounds, bioaffinity compounds, biomaterials, biopolymers, biomedical devices, analytically detectable compounds, therapeutically active compounds, enzymes, peptides, proteins, antibodies, immune stimulators, radiolabels, fluorogens, biotin, drugs, haptens, DNA, RNA, polysaccharides, liposomes, virosomes, micelles, immunoglobulins, functional groups, other targeting moieties, or toxins.

In some embodiments, the lipid conjugate (e.g., PEG-lipid) comprises from about 0.1 mol % to about 2 mol %, from about 0.5 mol % to about 2 mol %, from about 1 mol % to about 2 mol %, from about 0.6 mol % to about 1.9 mol %, from about 0.7 mol % to about 1.8 mol %, from about 0.8 mol % to about 1.7 mol %, from about 0.9 mol % to about 1.6 mol %, from about 0.9 mol % to about 1.8 mol %, from about 1 mol % to about 1.8 mol %, from about 1 mol % to about 1.7 mol %, from about 1.2 mol % to about 1.8 mol %, from about 1.2 mol % to about 1.7 mol %, from about 1.3 mol % to about 1.6 mol %, or from about 1.4 mol % to about 1.5 mol % (or any fraction thereof or range therein) of the total lipid present in the particle.

In other embodiments, the lipid conjugate (e.g., PEG-lipid) comprises from about 0 mol % to about 20 mol %, from about 0.5 mol % to about 20 mol %, from about 2 mol % to about 20 mol %, from about 1.5 mol % to about 18 mol %, from about 2 mol % to about 15 mol %, from about 4 mol % to about 15 mol %, from about 2 mol % to about 12 mol %, from about 5 mol % to about 12 mol %, or about 2 mol % (or any fraction thereof or range therein) of the total lipid present in the particle.

In further embodiments, the lipid conjugate (e.g., PEG-lipid) comprises from about 4 mol % to about 10 mol %, from about 5 mol % to about 10 mol %, from about 5 mol % to about 9 mol %, from about 5 mol % to about 8 mol %, from about 6 mol % to about 9 mol %, from about 6 mol % to about 8 mol %, or about 5 mol %, 6 mol %, 7 mol %, 8 mol %, 9 mol %, or 10 mol % (or any fraction thereof or range therein) of the total lipid present in the particle.

Additional percentages and ranges of lipid conjugates suitable for use in the lipid particles of the present invention are described in PCT Publication No. WO 09/127060, U.S. Published Application No. US 2011/0071208, PCT Publication No. WO2011/000106, and U.S. Published Application No. US 2011/0076335, the disclosures of which are herein incorporated by reference in their entirety for all purposes.

One of ordinary skill in the art will appreciate that the concentration of the lipid conjugate can be varied depending on the lipid conjugate employed and the rate at which the lipid particle is to become fusogenic.

By controlling the composition and concentration of the lipid conjugate, one can control the rate at which the lipid conjugate exchanges out of the lipid particle and, in turn, the rate at which the lipid particle becomes fusogenic. For instance, when a PEG-DAA conjugate is used as the lipid conjugate, the rate at which the lipid particle becomes fusogenic can be varied, for example, by varying the concentration of the lipid conjugate, by varying the molecular weight of the PEG, or by varying the chain length and degree of saturation of the alkyl groups on the PEG-DAA conjugate. In addition, other variables including, for example, pH, temperature, ionic strength, etc. can be used to vary and/or control the rate at which the lipid particle becomes fusogenic. Other methods which can be used to control the rate at which the lipid particle becomes fusogenic will become apparent to those of skill in the art upon reading this disclosure. Also, by controlling the composition and concentration of the lipid conjugate, one can control the lipid particle size.

B. Additional Carrier Systems

Non-limiting examples of additional lipid-based carrier systems suitable for use in the present invention include lipoplexes (see, e.g., U.S. Patent Publication No. 20030203865; and Zhang et al., *J. Control Release*, 100: 165-180 (2004)), pH-sensitive lipoplexes (see, e.g., U.S. Patent Publication No. 20020192275), reversibly masked lipoplexes (see, e.g., U.S. Patent Publication Nos. 20030180950), cationic lipid-based compositions (see, e.g., U.S. Pat. No. 6,756,054; and U.S. Patent Publication No. 20050234232), cationic liposomes (see, e.g., U.S. Patent Publication Nos. 20030229040, 20020160038, and 20020012998; U.S. Pat. No. 5,908,635; and PCT Publication No. WO 01/72283), anionic liposomes (see, e.g., U.S. Patent Publication No. 20030026831), pH-sensitive liposomes (see, e.g., U.S. Patent Publication No. 20020192274; and AU 2003210303), antibody-coated liposomes (see, e.g., U.S. Patent Publication No. 20030108597; and PCT Publication No. WO 00/50008), cell-type specific liposomes (see, e.g., U.S. Patent Publication No. 20030198664), liposomes containing nucleic acid and peptides (see, e.g., U.S. Pat. No. 6,207,456), liposomes containing lipids derivatized with releasable hydrophilic polymers (see, e.g., U.S. Patent Publication No. 20030031704), lipid-entrapped nucleic acid (see, e.g., PCT Publication Nos. WO 03/057190 and WO 03/059322), lipid-encapsulated nucleic acid (see, e.g., U.S. Patent Publication No. 20030129221; and U.S. Pat. No. 5,756,122), other liposomal compositions (see, e.g., U.S. Patent Publication Nos. 20030035829 and 20030072794; and U.S. Pat. No. 6,200,599), stabilized mixtures of liposomes and emulsions (see, e.g., EP1304160), emulsion compositions (see, e.g., U.S. Pat. No. 6,747,014), and nucleic acid micro-emulsions (see, e.g., U.S. Patent Publication No. 20050037086).

Examples of polymer-based carrier systems suitable for use in the present invention include, but are not limited to, cationic polymer-nucleic acid complexes (i.e., polyplexes). To form a polyplex, a nucleic acid (e.g., a siRNA molecule, such as an siRNA molecule described in Table B) is typically complexed with a cationic polymer having a linear, branched, star, or dendritic polymeric structure that condenses the nucleic acid into positively charged particles capable of interacting with anionic proteoglycans at the cell surface and entering cells by endocytosis. In some embodiments, the polyplex comprises nucleic acid (e.g., a siRNA molecule, such as an siRNA molecule described in Table B) complexed with a cationic polymer such as polyethylenimine (PEI) (see, e.g., U.S. Pat. No. 6,013,240; commercially available from Qbiogene, Inc. (Carlsbad, Calif.) as In vivo jetPEI™, a linear form of PEI), polypropylenimine (PPI), polyvinylpyrrolidone (PVP), poly-L-lysine (PLL), diethylaminoethyl (DEAE)-dextran, poly($\beta$-amino ester) (PAE) polymers (see, e.g., Lynn et al., *J. Am. Chem. Soc.*, 123:8155-8156 (2001)), chitosan, polyamidoamine (PAMAM) dendrimers (see, e.g., Kukowska-Latallo et al., *Proc. Natl. Acad. Sci. USA*, 93:4897-4902 (1996)), porphyrin (see, e.g., U.S. Pat. No. 6,620,805), polyvinylether (see, e.g., U.S. Patent Publication No. 20040156909), polycyclic amidinium (see, e.g., U.S. Patent Publication No. 20030220289), other polymers comprising primary amine, imine, guanidine, and/or imidazole groups (see, e.g., U.S. Pat. No. 6,013,240; PCT Publication No. WO/9602655; PCT Publication No. WO95/21931; Zhang et al., *J. Control Release*, 100:165-180 (2004); and Tiera et al., *Curr. Gene Ther.*, 6:59-71 (2006)), and a mixture thereof. In other embodiments, the polyplex comprises cationic polymer-nucleic acid complexes as described in U.S. Patent Publication Nos. 20060211643, 20050222064, 20030125281, and 20030185890, and PCT Publication No. WO 03/066069; biodegradable poly($\beta$-amino ester) polymer-nucleic acid complexes as described in U.S. Patent Publication No. 20040071654; microparticles containing polymeric matrices as described in U.S. Patent Publication No. 20040142475; other microparticle compositions as described in U.S. Patent Publication No. 20030157030; condensed nucleic acid complexes as described in U.S. Patent Publication No. 20050123600; and nanocapsule and microcapsule compositions as described in AU 2002358514 and PCT Publication No. WO 02/096551.

In certain instances, the siRNA may be complexed with cyclodextrin or a polymer thereof. Non-limiting examples of cyclodextrin-based carrier systems include the cyclodextrin-modified polymer-nucleic acid complexes described in U.S. Patent Publication No. 20040087024; the linear cyclodextrin copolymer-nucleic acid complexes described in U.S. Pat. Nos. 6,509,323, 6,884,789, and 7,091,192; and the cyclodextrin polymer-complexing agent-nucleic acid complexes described in U.S. Pat. No. 7,018,609. In certain other instances, the interfering RNA may be complexed with a peptide or polypeptide. An example of a protein-based carrier system includes, but is not limited to, the cationic oligopeptide-nucleic acid complex described in PCT Publication No. WO95/21931.

Preparation of Lipid Particles

The nucleic acid-lipid particles of the present invention, in which a nucleic acid (e.g., a siRNA as described in Table B) is entrapped within the lipid portion of the particle and is protected from degradation, can be formed by any method known in the art including, but not limited to, a continuous mixing method, a direct dilution process, and an in-line dilution process.

In particular embodiments, the cationic lipids may comprise lipids of Formula I-III or salts thereof, alone or in combination with other cationic lipids. In other embodiments, the non-cationic lipids are egg sphingomyelin (ESM), distearoylphosphatidylcholine (DSPC), dioleoylphosphatidylcholine (DOPC), 1-palmitoyl-2-oleoyl-phosphatidylcholine (POPC), dipalmitoyl-phosphatidylcholine (DPPC), monomethyl-phosphatidylethanolamine, dimethyl-phosphatidylethanolamine, 14:0 PE (1,2-dimyristoyl-phosphatidylethanolamine (DMPE)), 16:0 PE (1,2-dipalmitoyl-phosphatidylethanolamine (DPPE)), 18:0 PE (1,2-distearoyl-phosphatidylethanolamine (DSPE)), 18:1 PE (1,2-dioleoyl-phosphatidylethanolamine (DOPE)), 18:1 trans PE (1,2-dielaidoyl-phosphatidylethanolamine (DEPE)), 18:0-18:1 PE (1-stearoyl-2-oleoyl-phosphatidylethanolamine (SOPE)), 16:0-18:1 PE (1-palmitoyl-2-oleoyl-phosphatidylethanolamine (POPE)), polyethylene glycol-based polymers (e.g., PEG 2000, PEG 5000, PEG-modified diacylglycerols, or PEG-modified dialkyloxypropyls), cholesterol, derivatives thereof, or combinations thereof.

In certain embodiments, the present invention provides nucleic acid-lipid particles produced via a continuous mixing method, e.g., a process that includes providing an aqueous solution comprising a siRNA in a first reservoir, providing an organic lipid solution in a second reservoir (wherein the lipids present in the organic lipid solution are solubilized in an organic solvent, e.g., a lower alkanol such as ethanol), and mixing the aqueous solution with the organic lipid solution such that the organic lipid solution mixes with the aqueous solution so as to substantially instantaneously produce a lipid vesicle (e.g., liposome) encapsulating the siRNA within the lipid vesicle. This process and the apparatus for carrying out this process are described in detail in U.S. Patent Publication No. 20040142025, the disclosure of which is herein incorporated by reference in its entirety for all purposes.

The action of continuously introducing lipid and buffer solutions into a mixing environment, such as in a mixing chamber, causes a continuous dilution of the lipid solution with the buffer solution, thereby producing a lipid vesicle substantially instantaneously upon mixing. As used herein, the phrase "continuously diluting a lipid solution with a buffer solution" (and variations) generally means that the lipid solution is diluted sufficiently rapidly in a hydration process with sufficient force to effectuate vesicle generation. By mixing the aqueous solution comprising a nucleic acid with the organic lipid solution, the organic lipid solution undergoes a continuous stepwise dilution in the presence of the buffer solution (i.e., aqueous solution) to produce a nucleic acid-lipid particle.

The nucleic acid-lipid particles formed using the continuous mixing method typically have a size of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, less than about 120 nm, 110 nm, 100 nm, 90 nm, or 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm (or any fraction thereof or range therein). The particles thus formed do not aggregate and are optionally sized to achieve a uniform particle size.

In another embodiment, the present invention provides nucleic acid-lipid particles produced via a direct dilution process that includes forming a lipid vesicle (e.g., liposome) solution and immediately and directly introducing the lipid vesicle solution into a collection vessel containing a controlled amount of dilution buffer. In preferred aspects, the collection vessel includes one or more elements configured to stir the contents of the collection vessel to facilitate dilution. In one aspect, the amount of dilution buffer present in the collection vessel is substantially equal to the volume of lipid vesicle solution introduced thereto. As a non-limiting example, a lipid vesicle solution in 45% ethanol when introduced into the collection vessel containing an equal volume of dilution buffer will advantageously yield smaller particles.

In yet another embodiment, the present invention provides nucleic acid-lipid particles produced via an in-line dilution process in which a third reservoir containing dilution buffer is fluidly coupled to a second mixing region. In this embodiment, the lipid vesicle (e.g., liposome) solution formed in a first mixing region is immediately and directly mixed with dilution buffer in the second mixing region. In preferred aspects, the second mixing region includes a T-connector arranged so that the lipid vesicle solution and the dilution buffer flows meet as opposing 180° flows; however, connectors providing shallower angles can be used, e.g., from about 27° to about 180° (e.g., about 90°). A pump mechanism delivers a controllable flow of buffer to the second mixing region. In one aspect, the flow rate of dilution buffer provided to the second mixing region is controlled to be substantially equal to the flow rate of lipid vesicle solution introduced thereto from the first mixing region. This embodiment advantageously allows for more control of the flow of dilution buffer mixing with the lipid vesicle solution in the second mixing region, and therefore also the concentration of lipid vesicle solution in buffer throughout the second mixing process. Such control of the dilution buffer flow rate advantageously allows for small particle size formation at reduced concentrations.

These processes and the apparatuses for carrying out these direct dilution and in-line dilution processes are described in detail in U.S. Patent Publication No. 20070042031, the disclosure of which is herein incorporated by reference in its entirety for all purposes.

The nucleic acid-lipid particles formed using the direct dilution and in-line dilution processes typically have a size of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, less than about 120 nm, 110 nm, 100 nm, 90 nm, or 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm (or any fraction thereof or range therein). The particles thus formed do not aggregate and are optionally sized to achieve a uniform particle size.

If needed, the lipid particles of the invention can be sized by any of the methods available for sizing liposomes. The sizing may be conducted in order to achieve a desired size range and relatively narrow distribution of particle sizes.

Several techniques are available for sizing the particles to a desired size. One sizing method, used for liposomes and equally applicable to the present particles, is described in U.S. Pat. No. 4,737,323, the disclosure of which is herein incorporated by reference in its entirety for all purposes. Sonicating a particle suspension either by bath or probe sonication produces a progressive size reduction down to particles of less than about 50 nm in size. Homogenization is another method which relies on shearing energy to fragment larger particles into smaller ones. In a typical homogenization procedure, particles are recirculated through a standard emulsion homogenizer until selected particle sizes, typically between about 60 and about 80 nm, are observed. In both methods, the particle size distribution can be monitored by conventional laser-beam particle size discrimination, or QELS.

Extrusion of the particles through a small-pore polycarbonate membrane or an asymmetric ceramic membrane is also an effective method for reducing particle sizes to a relatively well-defined size distribution. Typically, the suspension is cycled through the membrane one or more times until the desired particle size distribution is achieved. The particles may be extruded through successively smaller-pore membranes, to achieve a gradual reduction in size.

In some embodiments, the nucleic acids present in the particles (e.g., the siRNA molecules) are precondensed as described in, e.g., U.S. patent application Ser. No. 09/744,103, the disclosure of which is herein incorporated by reference in its entirety for all purposes.

In other embodiments, the methods may further comprise adding non-lipid polycations which are useful to effect the lipofection of cells using the present compositions. Examples of suitable non-lipid polycations include, hexadimethrine bromide (sold under the brand name POLYBRENE®, from Aldrich Chemical Co., Milwaukee, Wis., USA) or other salts of hexadimethrine. Other suitable polycations include, for example, salts of poly-L-ornithine, poly-L-arginine, poly-L-lysine, poly-D-lysine, polyallylamine, and polyethyleneimine. Addition of these salts is preferably after the particles have been formed.

In some embodiments, the nucleic acid (e.g., siRNA) to lipid ratios (mass/mass ratios) in a formed nucleic acid-lipid particle will range from about 0.01 to about 0.2, from about 0.05 to about 0.2, from about 0.02 to about 0.1, from about 0.03 to about 0.1, or from about 0.01 to about 0.08. The ratio of the starting materials (input) also falls within this range. In other embodiments, the particle preparation uses about 400 μg nucleic acid per 10 mg total lipid or a nucleic acid to lipid mass ratio of about 0.01 to about 0.08 and, more preferably, about 0.04, which corresponds to 1.25 mg of total lipid per 50 μg of nucleic acid. In other preferred embodiments, the particle has a nucleic acid:lipid mass ratio of about 0.08.

In other embodiments, the lipid to nucleic acid (e.g., siRNA) ratios (mass/mass ratios) in a formed nucleic acid-lipid particle will range from about 1 (1:1) to about 100 (100:1), from about 5 (5:1) to about 100 (100:1), from about 1 (1:1) to about 50 (50:1), from about 2 (2:1) to about 50 (50:1), from about 3 (3:1) to about 50 (50:1), from about 4 (4:1) to about 50 (50:1), from about 5 (5:1) to about 50 (50:1), from about 1 (1:1) to about 25 (25:1), from about 2 (2:1) to about 25 (25:1), from about 3 (3:1) to about 25 (25:1), from about 4 (4:1) to about 25 (25:1), from about 5 (5:1) to about 25 (25:1), from about 5 (5:1) to about 20 (20:1), from about 5 (5:1) to about 15 (15:1), from about 5 (5:1) to about 10 (10:1), or about 5 (5:1), 6 (6:1), 7 (7:1), 8 (8:1), 9 (9:1), 10 (10:1), 11 (11:1), 12 (12:1), 13 (13:1), 14 (14:1), 15 (15:1), 16 (16:1), 17 (17:1), 18 (18:1), 19 (19:1), 20 (20:1), 21 (21:1), 22 (22:1), 23 (23:1), 24 (24:1), or 25 (25:1), or any fraction thereof or range therein. The ratio of the starting materials (input) also falls within this range.

As previously discussed, the conjugated lipid may further include a CPL. A variety of general methods for making lipid particle-CPLs (CPL-containing lipid particles) are discussed herein. Two general techniques include the "post-insertion" technique, that is, insertion of a CPL into, for example, a pre-formed lipid particle, and the "standard" technique, wherein the CPL is included in the lipid mixture during, for example, the lipid particle formation steps. The post-insertion technique results in lipid particles having CPLs mainly in the external face of the lipid particle bilayer membrane, whereas standard techniques provide lipid particles having CPLs on both internal and external faces. The method is especially useful for vesicles made from phospholipids (which can contain cholesterol) and also for vesicles containing PEG-lipids (such as PEG-DAAs and PEG-DAGs). Methods of making lipid particle-CPLs are taught, for example, in U.S. Pat. Nos. 5,705,385; 6,586,410; 5,981,501; 6,534,484; and 6,852,334; U.S. Patent Publication No. 20020072121; and PCT Publication No. WO 00/62813, the disclosures of which are herein incorporated by reference in their entirety for all purposes.

Kits

The present invention also provides lipid particles in kit form. In some embodiments, the kit comprises a container which is compartmentalized for holding the various elements of the lipid particles (e.g., the active agents, such as siRNA molecules and the individual lipid components of the particles). Preferably, the kit comprises a container (e.g., a vial or ampoule) which holds the lipid particles of the invention, wherein the particles are produced by one of the processes set forth herein. In certain embodiments, the kit may further comprise an endosomal membrane destabilizer (e.g., calcium ions). The kit typically contains the particle compositions of the invention, either as a suspension in a pharmaceutically acceptable carrier or in dehydrated form, with instructions for their rehydration (if lyophilized) and administration.

The formulations of the present invention can be tailored to preferentially target particular cells, tissues, or organs of interest. Preferential targeting of a nucleic acid-lipid particle may be carried out by controlling the composition of the lipid particle itself. In particular embodiments, the kits of the invention comprise these lipid particles, wherein the particles are present in a container as a suspension or in dehydrated form.

In certain instances, it may be desirable to have a targeting moiety attached to the surface of the lipid particle to further enhance the targeting of the particle. Methods of attaching targeting moieties (e.g., antibodies, proteins, etc.) to lipids (such as those used in the present particles) are known to those of skill in the art.

Administration of Lipid Particles

Once formed, the lipid particles of the invention are particularly useful for the introduction of a siRNA molecule (e.g., a siRNA molecule as described in Table B) into cells. Accordingly, the present invention also provides methods for introducing a siRNA molecule into a cell. In particular embodiments, the siRNA molecule is introduced into an infected cell. The methods may be carried out in vitro or in vivo by first forming the particles as described above and then contacting the particles with the cells for a period of time sufficient for delivery of siRNA to the cells to occur.

The lipid particles of the invention (e.g., a nucleic-acid lipid particle) can be adsorbed to almost any cell type with which they are mixed or contacted. Once adsorbed, the particles can either be endocytosed by a portion of the cells, exchange lipids with cell membranes, or fuse with the cells. Transfer or incorporation of the siRNA portion of the particle can take place via any one of these pathways. In particular, when fusion takes place, the particle membrane is integrated into the cell membrane and the contents of the particle combine with the intracellular fluid.

The lipid particles of the invention (e.g., nucleic acid-lipid particles) can be administered either alone or in a mixture with a pharmaceutically acceptable carrier (e.g., physiological saline or phosphate buffer) selected in accordance with the route of administration and standard pharmaceutical practice. Generally, normal buffered saline (e.g., 135-150 mM NaCl) will be employed as the pharmaceutically acceptable carrier. Other suitable carriers include, e.g., water, buffered water, 0.4% saline, 0.3% glycine, and the like, including glycoproteins for enhanced stability, such as albumin, lipoprotein, globulin, etc. Additional suitable carriers are described in, e.g., REMINGTON'S PHARMACEUTICAL SCIENCES, Mack Publishing Company, Philadelphia, Pa., 17th ed. (1985). As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The phrase "pharmaceutically acceptable" refers to molecular entities and compositions that do not produce an allergic or similar untoward reaction when administered to a human.

The pharmaceutically acceptable carrier is generally added following lipid particle formation. Thus, after the lipid particle is formed, the particle can be diluted into pharmaceutically acceptable carriers such as normal buffered saline.

The concentration of particles in the pharmaceutical formulations can vary widely, i.e., from less than about 0.05%, usually at or at least about 2 to 5%, to as much as about 10 to 90% by weight, and will be selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, particles composed of irritating lipids may be diluted to low concentrations to lessen inflammation at the site of administration.

The pharmaceutical compositions of the present invention may be sterilized by conventional, well-known sterilization techniques. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, and calcium chloride. Additionally, the particle suspension may include lipid-protective agents which protect lipids against free-radical and lipid-peroxidative damages on storage. Lipophilic free-radical quenchers, such as alphatocopherol, and water-soluble iron-specific chelators, such as ferrioxamine, are suitable.

In some embodiments, the lipid particles of the invention are particularly useful in methods for the therapeutic delivery of one or more siRNA molecules (e.g., an siRNA molecule as described in Table B). In particular, it is an object of this invention to provide in vivo methods for treatment of MARV infection in humans by downregulating or silencing the transcription and/or translation of one or more MARV genes.

A. In Vivo Administration

Systemic delivery for in vivo therapy, e.g., delivery of a siRNA molecule described herein, such as an siRNA described in Table B, to a distal target cell via body systems such as the circulation, has been achieved using nucleic acid-lipid particles such as those described in PCT Publication Nos. WO 05/007196, WO 05/121348, WO 05/120152, and WO 04/002453, the disclosures of which are herein incorporated by reference in their entirety for all purposes. The present invention also provides fully encapsulated lipid particles that protect the siRNA from nuclease degradation in serum, are non-immunogenic, are small in size, and are suitable for repeat dosing.

For in vivo administration, administration can be in any manner known in the art, e.g., by injection, oral administration, inhalation (e.g., intransal or intratracheal), transdermal application, or rectal administration. Administration can be accomplished via single or divided doses. The pharmaceutical compositions can be administered parenterally, i.e., intraarticularly, intravenously, intraperitoneally, subcutaneously, or intramuscularly. In some embodiments, the pharmaceutical compositions are administered intravenously or intraperitoneally by a bolus injection (see, e.g., U.S. Pat. No. 5,286,634). Intracellular nucleic acid delivery has also been discussed in Straubringer et al., *Methods Enzymol.,* 101:512 (1983); Mannino et al., *Biotechniques,* 6:682 (1988); Nicolau et al., *Crit. Rev. Ther. Drug Carrier Syst.,* 6:239 (1989); and Behr, *Acc. Chem. Res.,* 26:274 (1993). Still other methods of administering lipid-based therapeutics are described in, for example, U.S. Pat. Nos. 3,993,754; 4,145,410; 4,235,871; 4,224,179; 4,522,803; and 4,588,578. The lipid particles can be administered by direct injection at the site of disease or by injection at a site distal from the site of disease (see, e.g., Culver, HUMAN GENE THERAPY, MaryAnn Liebert, Inc., Publishers, New York. pp. 70-71 (1994)). The disclosures of the above-described references are herein incorporated by reference in their entirety for all purposes.

In embodiments where the lipid particles of the present invention are administered intravenously, at least about 5%, 10%, 15%, 20%, or 25% of the total injected dose of the particles is present in plasma about 8, 12, 24, 36, or 48 hours after injection. In other embodiments, more than about 20%, 30%, 40% and as much as about 60%, 70% or 80% of the total injected dose of the lipid particles is present in plasma about 8, 12, 24, 36, or 48 hours after injection. In certain instances, more than about 10% of a plurality of the particles is present in the plasma of a mammal about 1 hour after administration. In certain other instances, the presence of the lipid particles is detectable at least about 1 hour after administration of the particle. In some embodiments, the presence of a siRNA molecule is detectable in cells at about 8, 12, 24, 36, 48, 60, 72 or 96 hours after administration. In other embodiments, downregulation of expression of a target sequence, such as a viral or host sequence, by a siRNA molecule is detectable at about 8, 12, 24, 36, 48, 60, 72 or 96 hours after administration. In yet other embodiments, downregulation of expression of a target sequence, such as a viral or host sequence, by a siRNA molecule occurs preferentially in infected cells and/or cells capable of being infected. In further embodiments, the presence or effect of a siRNA molecule in cells at a site proximal or distal to the site of administration is detectable at about 12, 24, 48, 72, or 96 hours, or at about 6, 8, 10, 12, 14, 16, 18, 19, 20, 22, 24, 26, or 28 days after administration. In additional embodiments, the lipid particles of the invention are administered parenterally or intraperitoneally.

The compositions of the present invention, either alone or in combination with other suitable components, can be made into aerosol formulations (i.e., they can be "nebulized") to be administered via inhalation (e.g., intranasally or intratracheally) (see, Brigham et al., *Am. J Sci.*, 298:278 (1989)). Aerosol formulations can be placed into pressurized acceptable propellants, such as dichlorodifluoromethane, propane, nitrogen, and the like.

In certain embodiments, the pharmaceutical compositions may be delivered by intranasal sprays, inhalation, and/or other aerosol delivery vehicles. Methods for delivering nucleic acid compositions directly to the lungs via nasal aerosol sprays have been described, e.g., in U.S. Pat. Nos. 5,756,353 and 5,804,212. Likewise, the delivery of drugs using intranasal microparticle resins and lysophosphatidylglycerol compounds (U.S. Pat. No. 5,725,871) are also well-known in the pharmaceutical arts. Similarly, transmucosal drug delivery in the form of a polytetrafluoroetheylene support matrix is described in U.S. Pat. No. 5,780,045. The disclosures of the above-described patents are herein incorporated by reference in their entirety for all purposes.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions are preferably administered, for example, by intravenous infusion, orally, topically, intraperitoneally, intravesically, or intrathecally.

Generally, when administered intravenously, the lipid particle formulations are formulated with a suitable pharmaceutical carrier. Many pharmaceutically acceptable carriers may be employed in the compositions and methods of the present invention. Suitable formulations for use in the present invention are found, for example, in REMINGTON'S PHARMACEUTICAL SCIENCES, Mack Publishing Company, Philadelphia, Pa., 17th ed. (1985). A variety of aqueous carriers may be used, for example, water, buffered water, 0.4% saline, 0.3% glycine, and the like, and may include glycoproteins for enhanced stability, such as albumin, lipoprotein, globulin, etc. Generally, normal buffered saline (135-150 mM NaCl) will be employed as the pharmaceutically acceptable carrier, but other suitable carriers will suffice. These compositions can be sterilized by conventional liposomal sterilization techniques, such as filtration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc. These compositions can be sterilized using the techniques referred to above or, alternatively, they can be produced under sterile conditions. The resulting aqueous solutions may be packaged for use or filtered under aseptic conditions and lyophilized, the lyophilized preparation being combined with a sterile aqueous solution prior to administration.

In certain applications, the lipid particles disclosed herein may be delivered via oral administration to the individual. The particles may be incorporated with excipients and used in the form of ingestible tablets, buccal tablets, troches, capsules, pills, lozenges, elixirs, mouthwash, suspensions, oral sprays, syrups, wafers, and the like (see, e.g., U.S. Pat. Nos. 5,641,515, 5,580,579, and 5,792,451, the disclosures of which are herein incorporated by reference in their entirety for all purposes). These oral dosage forms may also contain the following: binders, gelatin; excipients, lubricants, and/or flavoring agents. When the unit dosage form is a capsule, it may contain, in addition to the materials described above, a liquid carrier. Various other materials may be present as coatings or to otherwise modify the physical form of the dosage unit. Of course, any material used in preparing any unit dosage form should be pharmaceutically pure and substantially non-toxic in the amounts employed.

Typically, these oral formulations may contain at least about 0.1% of the lipid particles or more, although the percentage of the particles may, of course, be varied and may conveniently be between about 1% or 2% and about 60% or 70% or more of the weight or volume of the total formulation. Naturally, the amount of particles in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

Formulations suitable for oral administration can consist of (a) liquid solutions, such as an effective amount of a packaged siRNA molecule (e.g., a siRNA molecule described in Table B) suspended in diluents such as water, saline, or PEG 400; (b) capsules, sachets, or tablets, each containing a predetermined amount of a siRNA molecule, as liquids, solids, granules, or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise a siRNA molecule in a flavor, e.g., sucrose, as well as pastilles comprising the therapeutic nucleic acid in an inert base, such as gelatin and glycerin or sucrose and acacia emulsions, gels, and the like containing, in addition to the siRNA molecule, carriers known in the art.

In another example of their use, lipid particles can be incorporated into a broad range of topical dosage forms. For instance, a suspension containing nucleic acid-lipid particles can be formulated and administered as gels, oils, emulsions, topical creams, pastes, ointments, lotions, foams, mousses, and the like.

When preparing pharmaceutical preparations of the lipid particles of the invention, it is preferable to use quantities of the particles which have been purified to reduce or eliminate empty particles or particles with therapeutic agents such as siRNA associated with the external surface.

The methods of the present invention may be practiced in a variety of hosts. Preferred hosts include mammalian species, such as primates (e.g., humans and chimpanzees as well as other nonhuman primates), canines, felines, equines, bovines, ovines, caprines, rodents (e.g., rats and mice), lagomorphs, and swine.

The amount of particles administered will depend upon the ratio of siRNA molecules to lipid, the particular siRNA used, the strain of MARV being treated, the age, weight, and condition of the patient, and the judgment of the clinician, but will generally be between about 0.01 and about 50 mg per kilogram of body weight, preferably between about 0.1 and about 5 mg/kg of body weight, or about $10^8$-$10^{10}$ particles per administration (e.g., injection).

B. In Vitro Administration

For in vitro applications, the delivery of siRNA molecules can be to any cell grown in culture. In preferred embodiments, the cells are animal cells, more preferably mammalian cells, and most preferably human cells.

Contact between the cells and the lipid particles, when carried out in vitro, takes place in a biologically compatible medium. The concentration of particles varies widely depending on the particular application, but is generally between about 1 μmol and about 10 mmol. Treatment of the cells with the lipid particles is generally carried out at physiological temperatures (about 37° C.) for periods of time of from about 1 to 48 hours, preferably of from about 2 to 4 hours.

In one group of preferred embodiments, a lipid particle suspension is added to 60-80% confluent plated cells having a cell density of from about $10^3$ to about $10^5$ cells/ml, more preferably about $2\times10^4$ cells/ml. The concentration of the suspension added to the cells is preferably of from about 0.01 to 0.2 μg/ml, more preferably about 0.1 μg/mi.

To the extent that tissue culture of cells may be required, it is well-known in the art. For example, Freshney, Culture of Animal Cells, a Manual of Basic Technique, 3rd Ed., Wiley-Liss, New York (1994), Kuchler et al., Biochemical Methods in Cell Culture and Virology, Dowden, Hutchinson and Ross, Inc. (1977), and the references cited therein provide a general guide to the culture of cells. Cultured cell systems often will be in the form of monolayers of cells, although cell suspensions are also used.

Using an Endosomal Release Parameter (ERP) assay, the delivery efficiency of a nucleic acid-lipid particle of the invention can be optimized. An ERP assay is described in detail in U.S. Patent Publication No. 20030077829, the disclosure of which is herein incorporated by reference in its entirety for all purposes. More particularly, the purpose of an ERP assay is to distinguish the effect of various cationic lipids and helper lipid components of the lipid particle based on their relative effect on binding/uptake or fusion with/destabilization of the endosomal membrane. This assay allows one to determine quantitatively how each component of the lipid particle affects delivery efficiency, thereby optimizing the lipid particle. Usually, an ERP assay measures expression of a reporter protein (e.g., luciferase, β-galactosidase, green fluorescent protein (GFP), etc.), and in some instances, a lipid particle formulation optimized for an expression plasmid will also be appropriate for encapsulating an interfering RNA. In other instances, an ERP assay can be adapted to measure downregulation of transcription or translation of a target sequence in the presence or absence of an interfering RNA (e.g., siRNA). By comparing the ERPs for each of the various lipid particles, one can readily determine the optimized system, e.g., the lipid particle that has the greatest uptake in the cell.

C. Detection of Lipid Particles

In some embodiments, the lipid particles of the present invention are detectable in the subject at about 1, 2, 3, 4, 5, 6, 7, 8 or more hours. In other embodiments, the lipid particles of the present invention are detectable in the subject at about 8, 12, 24, 48, 60, 72, or 96 hours, or about 6, 8, 10, 12, 14, 16, 18, 19, 22, 24, 25, or 28 days after administration of the particles. The presence of the particles can be detected in the cells, tissues, or other biological samples from the subject. The particles may be detected, e.g., by direct detection of the particles, detection of a siRNA sequence, detection of the target sequence of interest (i.e., by detecting expression or reduced expression of the sequence of interest), detection of a compound modulated by an Marburg virus protein (e.g., interferon), detection of viral load in the subject, or a combination thereof.

1. Detection of Particles

Lipid particles of the invention can be detected using any method known in the art. For example, a label can be coupled directly or indirectly to a component of the lipid particle using methods well-known in the art. A wide variety of labels can be used, with the choice of label depending on sensitivity required, ease of conjugation with the lipid particle component, stability requirements, and available instrumentation and disposal provisions. Suitable labels include, but are not limited to, spectral labels such as fluorescent dyes (e.g., fluorescein and derivatives, such as fluorescein isothiocyanate (FITC) and Oregon Green™; rhodamine and derivatives such Texas red, tetrarhodimine isothiocynate (TRITC), etc., digoxigenin, biotin, phycoerythrin, AMCA, CyDyes™, and the like; radiolabels such as $^3$H, $^{125}$I, $^{35}$S, $^{14}$C, $^{32}$P, $^{33}$P, etc.; enzymes such as horse radish peroxidase, alkaline phosphatase, etc.; spectral colorimetric labels such as colloidal gold or colored glass or plastic beads such as polystyrene, polypropylene, latex, etc. The label can be detected using any means known in the art.

2. Detection of Nucleic Acids

Nucleic acids (e.g., siRNA molecules) are detected and quantified herein by any of a number of means well-known to those of skill in the art. The detection of nucleic acids may proceed by well-known methods such as Southern analysis, Northern analysis, gel electrophoresis, PCR, radiolabeling, scintillation counting, and affinity chromatography. Additional analytic biochemical methods such as spectrophotometry, radiography, electrophoresis, capillary electrophoresis, high performance liquid chromatography (HPLC), thin layer chromatography (TLC), and hyperdiffusion chromatography may also be employed.

The selection of a nucleic acid hybridization format is not critical. A variety of nucleic acid hybridization formats are known to those skilled in the art. For example, common formats include sandwich assays and competition or displacement assays. Hybridization techniques are generally described in, e.g., "Nucleic Acid Hybridization, A Practical Approach," Eds. Hames and Higgins, IRL Press (1985).

The sensitivity of the hybridization assays may be enhanced through the use of a nucleic acid amplification system which multiplies the target nucleic acid being detected. In vitro amplification techniques suitable for amplifying sequences for use as molecular probes or for generating nucleic acid fragments for subsequent subcloning are known. Examples of techniques sufficient to direct persons of skill through such in vitro amplification methods, including the polymerase chain reaction (PCR), the ligase chain reaction (LCR), Qβ-replicase amplification, and other RNA polymerase mediated techniques (e.g., NASBA™) are found in Sambrook et al., In *Molecular Cloning: A Laboratory Manual*, Cold Spring Harbor Laboratory Press (2000); and Ausubel et al., SHORT PROTOCOLS IN MOLECULAR BIOLOGY, eds., Current Protocols, Greene Publishing Associates, Inc. and John Wiley & Sons, Inc. (2002); as well as U.S. Pat. No. 4,683,202; PCR Protocols, A Guide to Methods and Applications (Innis et al. eds.) Academic Press Inc. San Diego, Calif. (1990); Arnheim & Levinson (Oct. 1, 1990), *C&EN* 36; The *Journal Of NIH Research*, 3:81 (1991); Kwoh et al., *Proc. Natl. Acad. Sci. USA*, 86:1173 (1989); Guatelli et al., *Proc. Natl. Acad. Sci. USA*, 87:1874 (1990); Lomell et al., *J. Clin. Chem.*, 35:1826 (1989); Landegren et al., *Science*, 241:1077 (1988); Van Brunt, Biotechnology, 8:291 (1990); Wu and Wallace, Gene, 4:560 (1989); Barringer et al., Gene, 89:117 (1990); and Sooknanan and Malek, Biotechnology, 13:563 (1995). Improved methods of cloning in vitro amplified nucleic acids are described in U.S. Pat. No. 5,426,039. Other methods described in the art are the nucleic acid sequence based amplification (NASBA™, Cangene, Mississauga, Ontario) and Qβ-replicase systems. These systems can be used to directly identify mutants where the PCR or LCR primers are designed to be extended or ligated only when a select sequence is present. Alternatively, the select sequences can be generally amplified using, for example, nonspecific PCR primers and the amplified target region later probed for a specific sequence indicative of a mutation. The disclosures of the above-described references are herein incorporated by reference in their entirety for all purposes.

Nucleic acids for use as probes, e.g., in in vitro amplification methods, for use as gene probes, or as inhibitor components are typically synthesized chemically according to the solid phase phosphoramidite triester method described by Beaucage et al., Tetrahedron Letts., 22:1859 1862 (1981), e.g., using an automated synthesizer, as described in Needham VanDevanter et al., Nucleic Acids Res., 12:6159 (1984). Purification of polynucleotides, where necessary, is typically performed by either native acrylamide gel electrophoresis or by anion exchange HPLC as described in Pearson et al., J. Chrom., 255:137 149 (1983). The sequence of the synthetic polynucleotides can be verified using the chemical degradation method of Maxam and Gilbert (1980) in Grossman and Moldave (eds.) Academic Press, New York, Methods in Enzymology, 65:499.

An alternative means for determining the level of transcription is in situ hybridization. In situ hybridization assays are well-known and are generally described in Angerer et al., Methods Enzymol., 152:649 (1987). In an in situ hybridization assay, cells are fixed to a solid support, typically a glass slide. If DNA is to be probed, the cells are denatured with heat or alkali. The cells are then contacted with a hybridization solution at a moderate temperature to permit annealing of specific probes that are labeled. The probes are preferably labeled with radioisotopes or fluorescent reporters.

EXAMPLES

The present invention will be described in greater detail by way of a specific example. The following example is offered for illustrative purposes, and is not intended to limit the invention in any manner. Those of skill in the art will readily recognize a variety of noncritical parameters which can be changed or modified to yield essentially the same results.

Example 1

This Example describes the selection of the MARV siRNA molecules set forth in Tables A and B, as well as biological assays used to test the activity of these siRNAs. Specifically, the design, screening and in vivo efficacy of novel nucleic acid-lipid particles as post-exposure treatment against MARV strains Angola, Ci67, and Ravn in newly developed lethal outbred guinea pig models of infection, and in vivo efficacy in nonhuman primates infected with MARV-Angola are described. As described herein, a 100% postexposure protection against the most pathogenic Angola strain of MARV has been demonstrated in guinea pigs and in nonhuman primates even when treatment was initiated three days after viral infection, and four to five days prior to death.

Materials and Methods

Design and In Vitro Screening of siRNAs

MARV mRNA sequences for Angola 1379c (DQ447653.1); Ci67 (EF446132.1); Musoke (DQ217792.1); and Ravn (DQ447649.1) were obtained from GenBank (http://www.ncbi.nlm.nih.gov/genbank/). Sequences were aligned using ClustalW (http://www.ebi.ac.uk/clustalw/). siRNA were designed to target conserved sequence regions of MARV VP24, VP35, VP40, NP, and L polymerase (Lpol) genes manually or by using a conventional siRNA design algorithm (Geisbert T W, Lee A C, Robbins M, et al. Postexposure protection of non-human primates against a lethal Ebola virus challenge with RNA interference: a proof-of-concept study. Lancet 2010; 375: 1896-905). siRNA with sequence homology to human mRNAs of 16 or more contiguous bases were excluded using BLAST (v.2.2.13) and eliminated siRNA that did not display 100% nucleotide sequence identity with at least 3 MARV strains (Angola, Ci67 and Musoke). siRNA were then 2'-O-methylated to abrogate immune stimulatory activity as described (Judge A D, Robbins M, Tavakoli I, et al. Confirming the RNAi-mediated mechanism of action of siRNA-based cancer therapeutics in mice. J Clin Invest 2009; 119:661-73). Single-stranded RNA oligonucleotides were synthesized by Integrated DNA Technologies and annealed to form siRNA duplexes by denaturation at 95° C. for 1 min followed by 1 h incubation at 37° C. siRNA were then encapsulated within lipid particle as described (Geisbert T W, Lee A C, Robbins M, et al. Postexposure protection of non-human primates against a lethal Ebola virus challenge with RNA interference: a proof-of-concept study. Lancet 2010; 375:1896-905).

siRNA activity against MARV VP24, VP35, VP40, NP and Lpol mRNAs were confirmed in vitro using a dual luciferase reporter assay assessing reduction in the expression of the respective viral transgenes cloned into the psiCHECK2 vector (Promega) in HepG2 cells (ATCC No. HB-8065) grown in MEM (Gibco) supplemented media. Gene synthesis and subcloning into psiCHECK2 was conducted by GenScript Inc. HepG2 cells were reverse-transfected with Lipofectamine 2000 (Invitrogen) complexes containing 0.75 μg of psiCHECK2 plasmid and lipid particle (20-0.8 nM) in 96 well plates. Lipid particle containing siRNA targeting Renilla luciferase (Rluc) or a non-specific target (ApoB) were used as positive and negative controls respectively. Cells were lysed 48 h after transfection. Luminescence was detected using the Dual Luciferase Reporter Assay kit according to manufacturer's protocol (Promega) using a Berthold luminometer (Berthold Detection Systems). The Renilla luciferase signal (reflecting target transgene expression) was normalized to the Firefly luciferase signal and expressed as percent gene expression relative to a plasmid-only control.

In Vitro Antiviral Efficacy

To confirm the efficacy of lead siRNA in lipid particles, they were tested in vitro against live MARV-Angola. The work was conducted at the Galveston National Laboratory (GNL) under BSL-4 biocontainment. HepG2 cells were seeded into 24-well plates and incubated at 37° C./5% $CO_2$ for 24 h prior to lipid particle treatment (10 nM or 100 nM). After 24 h incubation, cells were infected at a multiplicity of infection (MOI) of 0.5 or 0.1 for 1 h, after which the wells were washed with PBS and fresh media was added. The cells were then incubated for an additional 48 h prior to the collection of supernatants for plaque assay.

In Vivo Immune Stimulation Assays

A mouse study was performed in accordance with the Canadian Council on Animal Care guidelines following approval by the local Animal Care and Use Committee at Tekmira Pharmaceuticals Corporation in compliance with the animal welfare act, and other Federal statutes and regulations relating to animals and experiments involving animals, and the Guide for the Care and Use of Laboratory Animals, National Research Council. Six to eight-week-old female CD1 ICR mice (n=36; four per group) were subjected to a one week quarantine and acclimation period before study start. Nucleic acid-lipid particles (5 mg/kg) were administered by bolus intravenous injection in the lateral tail vein in 0.2 mL PBS. Plasma and livers were harvested 4 h after injection of the nucleic acid-lipid particles. Plasma cytokine measurements and liver IFN-induced protein with tetratricopeptide repeats (IFIT1) mRNA analysis were performed as described [20]. Clinical signs and organ weights were monitored and no differences from the PBS control-treated group were observed.

Antiviral Efficacy in Guinea Pigs

Outbred Hartley strain guinea pig models for MARV strains Angola, Ci67, and Ravn were developed by serial passaging of virus isolated from infected livers and/or spleens. The guinea pig-adapted MARV-Angola was developed by four passages in Hartley guinea pigs; the guinea pig-adapted MARV-Ci67 by two passages in strain 13 guinea pigs and three passages in Hartley guinea pigs; and the guinea pig-adapted MARV-Ravn by two passages in strain 13 guinea pigs and 1 passage in Hartley guinea pigs. The resulting adapted strains give rise to high plasma viraemia (up to $10^7$ pfu/mL) and are uniformly lethal with death occurring 6-9 days after challenge for MARV-Angola and 8-14 days after challenge for both MARV-Ci67 and MARV-Ravn. Animal studies were completed under BSL-4 biocontainment at the GNL and were approved by the UTMB Institutional Laboratory Animal Care and Use Committee (IACUC) in accordance with state and federal statutes and regulations relating to experiments involving animals and the Institutional Biosafety Committee. Female Hartley guinea pigs (351-400 grams) were purchased from Charles River Laboratories and subsequently quarantined and acclimatized for 1 week prior to MARV challenge. The siRNA duplexes were synthesized by Integrated DNA Technologies. Lipid encapsulation of the siRNAs was performed at Tekmira Pharmaceuticals as described (Geisbert T W, Lee A C, Robbins M, et al. Postexposure protection of non-human primates against a lethal Ebola virus challenge with RNA interference: a proof-of-concept study. Lancet 2010; 375: 1896-905). Individual animals were infected with approximately 1,000 plaque-forming units (pfu) of guinea pig-adapted MARV-Angola, MARV-Ci67, or MARV-Ravn by intraperitoneal (i.p) injection. Approximately 1 h after viral inoculation, lipid particles containing single or a 1:1 cocktail of 2'-O-methylated siRNA (0.5 mg/kg total) was administered by bolus retro-orbital injection and subsequent doses were given daily for a total of seven doses. Control animals were treated with lipid particles carrying a nonspecific siRNA (Luc-mod) or remained untreated. Survival of the animals was followed for 28 days after which survivors were euthanized at the study endpoint per IACUC protocol.

Antiviral Efficacy in Nonhuman Primates

Animal studies were completed under BSL-4 biocontainment at the GNL and were approved by the UTMB Institutional Laboratory Animal Care and Use Committee (IACUC) in accordance with state and federal statutes and regulations relating to experiments involving animals and the Institutional Biosafety Committee. Twenty-one healthy adult rhesus macaques (*Macaca mulatta*) of Chinese origin (4-8 kg) were used to conduct four separate studies (4 treated animals and 1 or 2 controls per study) where the time between virus challenge and initiation of treatment ranged from one hour, one day, two days or three days after infection. The siRNA duplexes were synthesized by ST Pharm Co. Lipid encapsulation of the siRNAs was performed at Tekmira Pharmaceuticals as described (Geisbert T W, Lee A C, Robbins M, et al. Postexposure protection of non-human primates against a lethal Ebola virus challenge with RNA interference: a proof-of-concept study. Lancet 2010; 375:1896-905). Individual animals were infected with approximately 1,000 plaque-forming units (pfu) of MARV-Angola by intramuscular (i.m) injection. Starting at either 1 hour, one day, two days or three days after viral inoculation, lipid particles containing single 2'-O-methylated siRNA (0.5 mg/kg total for one or two day treatment delay experiments, and 1.0 mg/kg total for three day treatment delay experiment) was administered by bolus intravenous injection and subsequent doses were given daily for a total of seven doses. Control animals were either left untreated or treated with lipid particles carrying a nonspecific siRNA (Luc-mod). A number of parameters were monitored during the course of the study including survival, clinical observations, hematology, serum biochemistry, blood coagulation, viremia and viral load in swabs and tissues by qRT-PCR and plaque assay. Survival of the animals was followed for 28 days after which survivors were euthanized at the study endpoint per IACUC protocol.

Statistical Analysis

Kaplan-Meier survival curves were plotted using GraphPad Prism software for each in vivo study. Differences between treatment groups and the control group were analyzed for statistical significance using Fisher's exact test (one-sided; $p<0.05$), and the Log rank test (when adjusted for multiple comparisons using Bonferroni correction, $p<0.00833$ for the guinea pig studies).

Virus Titration by Plaque Assay

MARV titration was performed by conventional plaque assay on Vero E6 cells from cell culture supernatants from in vitro efficacy experiments or from plasma collected from guinea pigs or from nonhuman primates as described elsewhere (Jones S M, Feldmann H, Stroher U, et al. Live attenuated recombinant vaccine protects nonhuman primates against Ebola and Marburg viruses. Nat Med 2005; 11:786-90; Daddario-DiCaprio K M, Geisbert T W, Stroher U, et al. Postexposure protection against Marburg haemorrhagic fever with recombinant vesicular stomatitis virus vectors in non-human primates: an efficacy assessment. Lancet 2006; 367:1399-404). Samples were collected from guinea pigs at day 7 post-infection or from rhesus macaques at day 0, 3, 6, 10, 14, 21 and 28 or at euthanasia. In brief, increasing 10-fold dilutions of the samples were adsorbed to Vero E6 monolayers in duplicate wells (200 uL). The limit of detection was 25 pfu/mL for the guinea pig study and 15 pfu/mL for the nonhuman primate studies.

Virus mRNA Quantitation by qRT-PCR

For in vitro infection studies, whole cell (HepG2) lysates from MARV-Angola infected cells were incubated with 1 mL of Trizol (Invitrogen) for 15 min with rocking every 5 min and total RNA isolation was performed according to manufacturer instructions. Isolated RNA was quantified using a NanoDrop 2000 (Thermo Scientific). 2 μg of total RNA were used to isolate mRNA using a Dynabead mRNA purification kit (Invitrogen). mRNA (30 ng) were used in a one-step qRT-PCR using primers and FAM-labelled probes for each MARV-Angola mRNA in question (VP35, VP40 or L). Primers and a VIC probe for human β-actin were used to normalize each viral mRNA to the amount of human β-actin mRNA present in each mRNA sample. FAM and VIC signals were recorded for each sample and the BioRad CFX manager software was used to collect the normalized expression of MARV-Angola mRNA compared to human β-actin mRNA.

For nonhuman primate studies, RNA was isolated from whole blood utilizing the Viral RNA mini-kit (Qiagen). Primers and a FAM-labelled probe targeting the NP gene of MARV were used for qRT-PCR. MARV RNA was detected using One-step probe qRT-PCR kits with the following cycle conditions: 50° C. for 10 minutes, 95° C. for 10 seconds, and 40 cycles of 95° C. for 10 seconds and 59° C. for 30 seconds. Threshold cycle (CT) values representing MARV genomes were used to calculate genomic equivalents based on CT values obtained using a MARV-Angola genomic standard.

Results siRNA Design and In Vitro Screening

The genus *Marburgvirus* consists of only one species, *Lake Victoria marburgvirus* (Feldmann H, Sanchez A, Geisbert T W. Filoviridae: Marburg and Ebola Viruses. In: Knipe D M, Howley P M, eds. Fields Virology. 6th ed. Philadelphia: Lippincott Williams & Wilkins, 2013:923-56), divided into two lineages. One of these lineages comprises a number of strains including Angola, Ci67, Musoke, Ozolins, and Popp which exhibit genomic sequence differences of only 0-7.4%, while the second lineage comprising the Ravn strain shows greater sequence disparity (21% when compared to strains in the other lineage). The broad range of sequence variation among the different strains confounds the design of broad spectrum siRNA therapeutics, however, the NP and VP24 genes show a higher percentage of conserved contiguous bases which are more amenable to siRNA design. The objective of the design strategy described herein was to obtain siRNA with broad spectrum activity against three (Angola, Musoke, and Ci67) or four (Angola, Musoke, Ci67, and Ravn) different MARV strains.

Target mRNA sequences from MARV strains were aligned using ClustalW and conserved regions were identified. Using the MARV-Angola mRNA sequence for each target as a template, a panel of siRNAs against VP24, VP35, NP, and L polymerase were designed, which was then triaged based on nucleotide complementarity between the target mRNA sequence and the 19 nucleotide core sequence of the antisense strand of the siRNA. siRNAs that did not have 100% sequence complementarity with at least three of the virus strains under consideration were downselected. siRNA were screened in a dual luciferase reporter assay against the relevant viral mRNA target on HepG2 cells (FIG. 1). Two siRNA targeting VP35 mRNA (301 and 321; FIG. 1A), two siRNA targeting VP40 (259 and 320; FIG. 1B), one siRNA targeting Lpol (6801; FIG. 1C), one siRNA targeting VP24 (518; FIG. 1D), and one siRNA targeting NP (718; FIG. 1E) were selected as lead candidates based on their potency (assessed by their ability to provide the highest mRNA knockdown at the lowest dose) and their antisense sequence complementarity with MARV strains Musoke, Angola, and Ci67 mRNAs. VP35-520, VP40-827, VP24-734, and NP-143 were chosen using additional criteria of antisense sequence complementarity with MARV-Ravn mRNAs.

Modification of siRNA for In Vivo Applications

Figure 2:
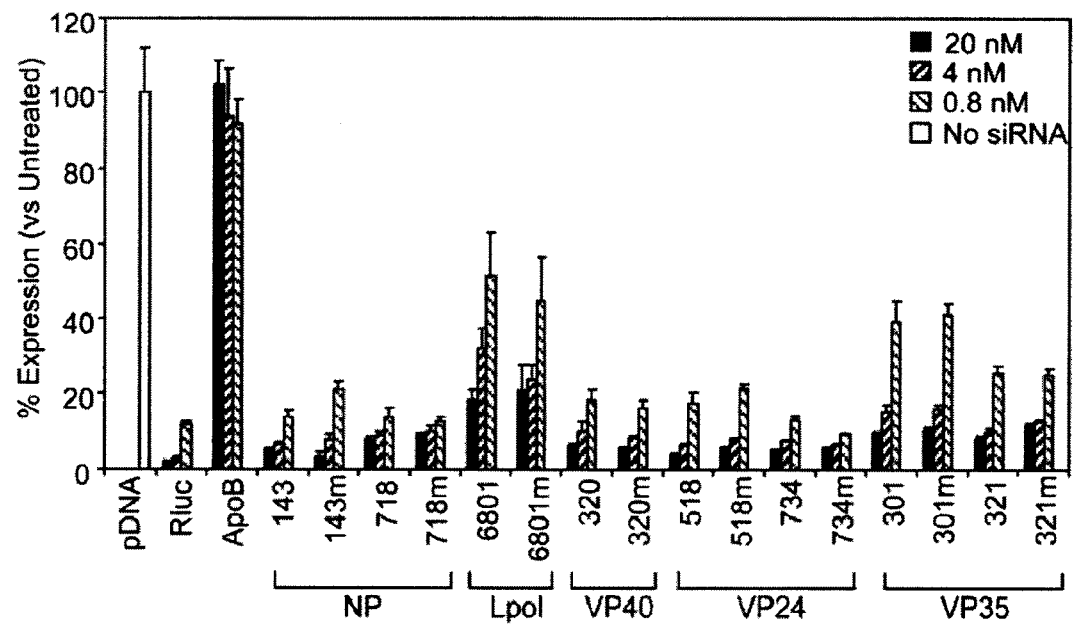

To minimize the inherent immune stimulatory properties of native siRNA sequences (Judge A D, Sood V, Shaw J R, Fang D, McClintock K, MacLachlan I. Sequence-dependent stimulation of the mammalian innate immune response by synthetic siRNA. Nat Biotechnol 2005; 23:457-62; Robbins M, Judge A, MacLachlan I. siRNA and innate immunity. Oligonucleotides 2009; 19:89-102), lead MARV siRNA were synthesized incorporating select 2'-O-methyl chemical modifications in both strands (Table 1a & 1b) as described previously (Judge A D, Robbins M, Tavakoli I, et al. Confirming the RNAi-mediated mechanism of action of siRNA-based cancer therapeutics in mice. J Clin Invest 2009; 119:661-73). The activity of both non-modified and modified lead MARV siRNA was compared in a dual luciferase reporter assay to confirm that their activity was not compromised by 2'-O-methylation (FIG. 2).

TABLE 1a siRNA Sense Strand Sequence and Target Strain

| siRNA | Sense Strand (5'-3')[a] | AS complementarity to MARV |
|---|---|---|
| Rluc | GCAAGAUCAUGCGGAAACUGG (SEQ ID NO: 25) | none |
| ApoB | AGUmGUCAmUCACACmUGAAUACC (SEQ ID NO: 27) | none |
| Luc | GAUUAUGUCCGGUUAUGUAAA (SEQ ID NO: 29) | none |
| Luc mod | GAmUmUAmUGmUCCGGmUmUAmUGmUAAA (SEQ ID NO: 31) | none |
| Lpol-6801m | CGmUCAAmGmGCAAACAACAmUmUmUA (SEQ ID NO: 13) | Angola, Ci67 and Musoke |
| VP40-320m | GmUCUmGCCAUGCUmUUCACmUUmUA (SEQ ID NO: 15) | Angola, Ci67 and Musoke |
| VP24-518m | CCAAmGAAmUUACAmGCAAmUCAmUmU (SEQ ID NO: 17) | Angola, Ci67 and Musoke |
| VP24-734m | CCAmGCAGmUAUmUGAAAmUAAAmGmU (SEQ ID NO: 19) | Angola, Ci67, Musoke and Ravn |
| NP-143m | mUCAGmGUmUAGUAmUCUmGUAAmUCA (SEQ ID NO: 21) | Angola, Ci67, Musoke and Ravn |
| NP-718m | GAmUUCmUCAGGACmUUCmUUAUmUmG (SEQ ID NO: 23) | Angola, Ci67 and Musoke |

[a]"m" denotes the presence of 2'-O-methyl modification at that ribo-nucleotide.

TABLE 1b siRNA Antisense Strand Sequence and Target Strain

| siRNA | Antisense Strand (5'-3')[a] | AS complementarity to MARV |
|---|---|---|
| Rluc | AGUUUCCGCAUGAUCUUGCUU (SEQ ID NO: 26) | none |
| ApoB | UAUmUCAmGUmGUGAUGACACmUUG (SEQ ID NO: 28) | none |
| Luc | UACAUAACCGGACAUAAUCAU (SEQ ID NO: 30) | none |
| Luc mod | UACAmUAACCGGACAmUAAmUCAU (SEQ ID NO: 32) | none |
| Lpol-6801m | AAmUGUUmGUmUUGCCUmUGACmGAA (SEQ ID NO: 14) | Angola, Ci67 and Musoke |
| VP40-320m | AAmGUmGAAAGCAmUmGGCAmGACAmU (SEQ ID NO: 16) | Angola, Ci67 and Musoke |
| VP24-518m | UGAUmUGCUmGUAAmUUCmUUGGmUC (SEQ ID NO: 18) | Angola, Ci67 and Musoke |
| VP24-734m | UUmUAmUUmUCAAUACUmGCmUGGmGmU (SEQ ID NO: 20) | Angola, Ci67, Musoke and Ravn |
| NP-143m | AUmUACAGAmUACmUAACCmUGAmUmG (SEQ ID NO: 22) | Angola, Ci67, Musoke and Ravn |
| NP-718m | AUAAmGAAmGmUCCUmGAGAAmUCmUA (SEQ ID NO: 24) | Angola, Ci67 and Musoke |

[a] "m" denotes the presence of 2'-O-methyl modification at that ribo-nucleotide.

In Vitro Efficacy

Figure 3:
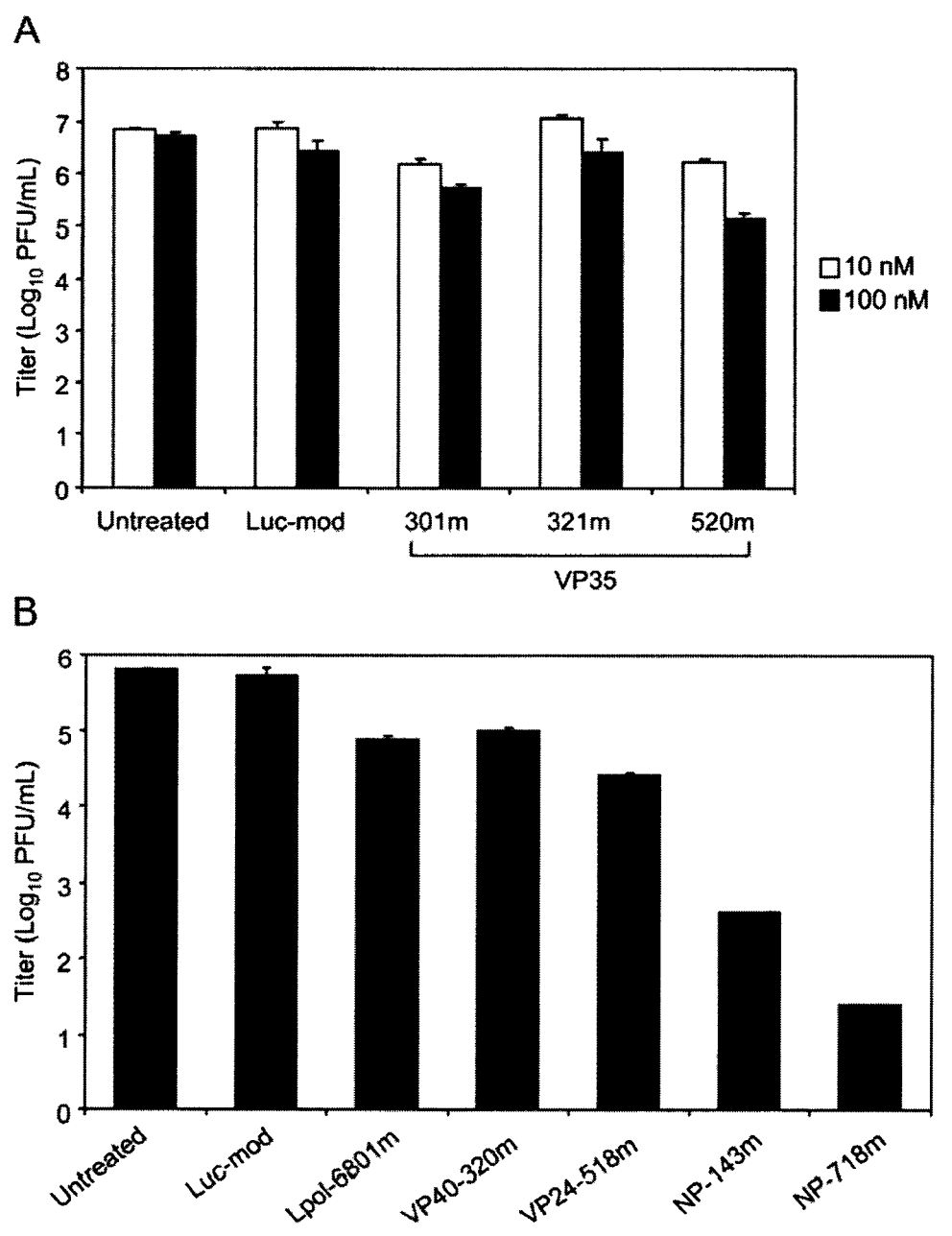
Figure 4:
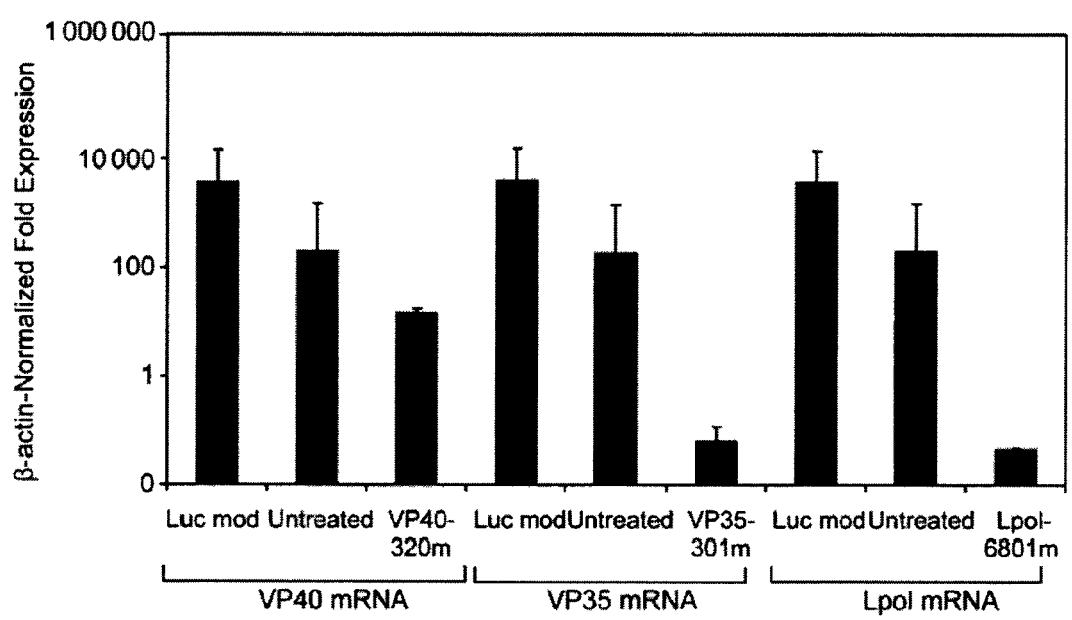
FIG. 4. Treatment of infected cells with 2'-O-methylated siRNA-lipid particles down-regulates viral mRNA expression. HepG2 cells were treated with nucleic acid-lipid particles targeting individual viral mRNAs, Luc control lipid particles or left untreated and 24 h later infected with MARV virus (Angola strain). Cells were lysed and viral mRNA levels were quantified by real-time PCR and normalized to human β-actin. Data represents the mean (n=3) of experimental results±SD.

To assess the antiviral efficacy of 2'-O-methylated siRNA in lipid particles, HepG2 cells were treated for 24 h and then infected with MARV-Angola. Limited antiviral efficacy was observed for all three VP35 siRNAs (FIG. 3A). To verify that the siRNAs mediated specific VP35 viral mRNA reduction in vitro, viral mRNA from these cells was quantified by qRT-PCR (normalized to human β-actin) (FIG. 4). Although specific viral mRNA knockdown was observed, VP35-targeting nucleic acid-lipid particles were not selected for subsequent in vivo evaluation due to poor in vitro antiviral activity. Nucleic acid-lipid particles targeting MARV Lpol, VP24 and VP40 mRNA exhibited antiviral efficacy, displaying up to one $\log_{10}$ reduction in pfu/mL (FIG. 3B). Nucleic acid-lipid particles targeting MARV NP mRNA exhibited significantly higher antiviral efficacy, resulting in four and three $\log_{10}$ pfu/mL reductions with NP-718m and NP-143m, respectively, when compared to controls (FIG. 3B). Lead siRNA targeting MARV Lpol, VP24, VP40, and NP were chosen for in vivo immune stimulation testing prior to selection for in vivo protective efficacy studies.

In Vivo Immune Stimulation

Lead modified siRNA (Lpol-6801m, VP40-320m, VP24-518m, NP-143m and NP-718m) were assessed for their ability to induce an immune response in ICR mice. A non-modified Luciferase-targeting (Luc) siRNA and a corresponding 2'-O-methylated siRNA (Luc-mod) were used as positive and negative controls for immune stimulation, respectively (Table 1a & 1b). The Luc positive control induced significant IFN-α, IFN-β, TNF-α and IL-6 cytokine induction in plasma and IFIT1 mRNA in liver at 4 h post-treatment while none of the other lipid particles showed increases above the level of the Luc-mod negative control (Table 2). These results confirmed that the lead 2'-O-methylated siRNAs did not possess significant immune stimulatory ability.

TABLE 2

Plasma Cytokine and Liver IFIT1 Messenger RNA Levels From Female ICR Mice (n = 4) 4 Hours After Treatment

| | Cytokines, pg/mL of Plasma | | | | | | | | Mean Fold Increase in IFIT mRNA Induction Relative to PBS (Normalized to GAPDH mRNA) | |
|---|---|---|---|---|---|---|---|---|---|---|
| | IFN-α | | IFN-β | | IL-6 | | TNF-α | | | |
| Treatment | Mean | SD | Mean | SD | Mean | SD | Mean | SD | Mean | SD |
| PBS | 77 | 60 | 25 | 4 | ND | ND | 5 | 5 | 1 | 0.3 |
| Luc | 3822 | 2531 | 684 | 460 | 426 | 220 | 249 | 185 | 248.7 | 56.5 |
| Luc mod | 82 | 73 | 25 | 1 | ND | ND | 11 | 13 | 1.4 | 0.9 |
| Lpol-6801m | 49 | 4 | 24 | 2 | ND | ND | ND | ND | 1.3 | 0.6 |
| VP40-320m | 84 | 67 | 27 | 3 | ND | ND | ND | ND | 1.4 | 0.5 |
| VP24-518m | 46 | 1 | 24 | 1 | ND | ND | ND | ND | 1.8 | 0.8 |
| VP24-734m | 84 | 68 | 26 | 1 | ND | ND | 2 | 4 | 1.1 | 0.4 |
| NP-143m | 47 | 6 | 30 | 5 | ND | ND | 5 | 8 | 1.5 | 0.4 |
| NP-718m | 53 | 12 | 27 | 2 | ND | ND | 12 | 24 | 4.6 | 4.3 |

Abbreviations:
GAPDH, Glyceraldehyde 3-phosphate dehydrogenase; IFIT, Interferon-induced protein with tetratricopeptide repeats 1; IFN, interferon; IL, interleukin; mRNA, messenger RNA; ND, not detected; PBS, phosphate-buffered saline; TNF, tumor necrosis factor.

In Vivo Activity

Figure 5:
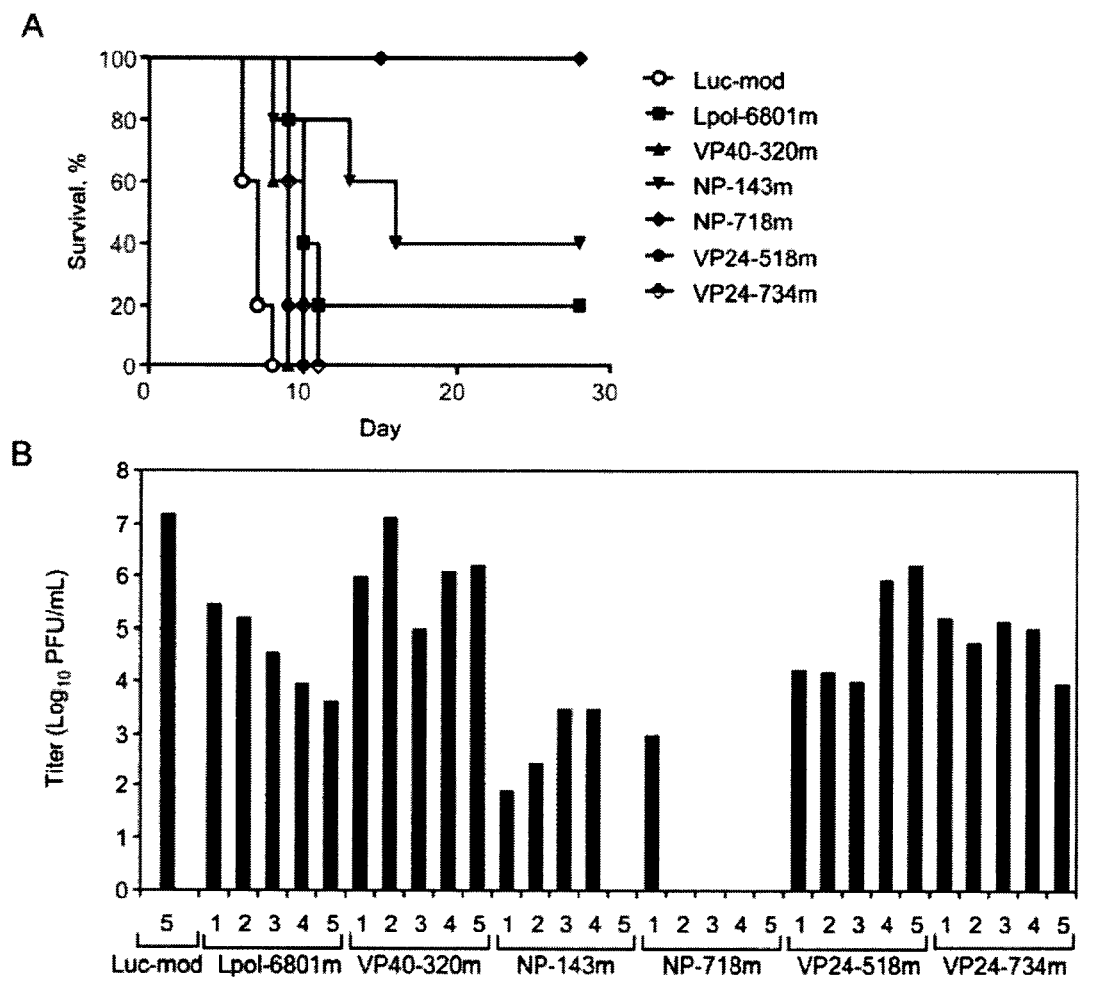
Figure 7:
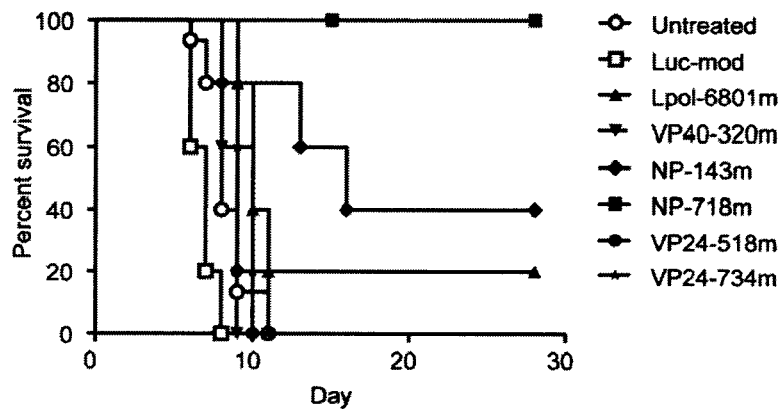
FIG. 7. 2'-O-methylated siRNAs in lipid particles confer protection to guinea pigs against MARV challenge, and this was found to be statistically significant upon the addition of historical controls. Survival of A, MARV Angola, B, MARV Ci67 and C, MARV-Ravn-infected Hartley strain guinea pigs after treatment with lipid particles containing NP-targeting 2-'O-methylated siRNA. Animals (n=5 per group) were treated 1 h after viral challenge, followed by six additional daily treatments with lipid particles containing 0.5 mg/kg of siRNA. Historical untreated animals (n=10) were included.
Figure 7:
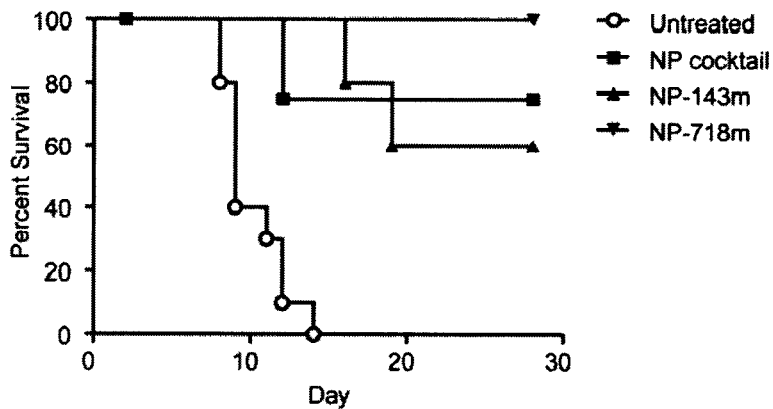
Figure 7:
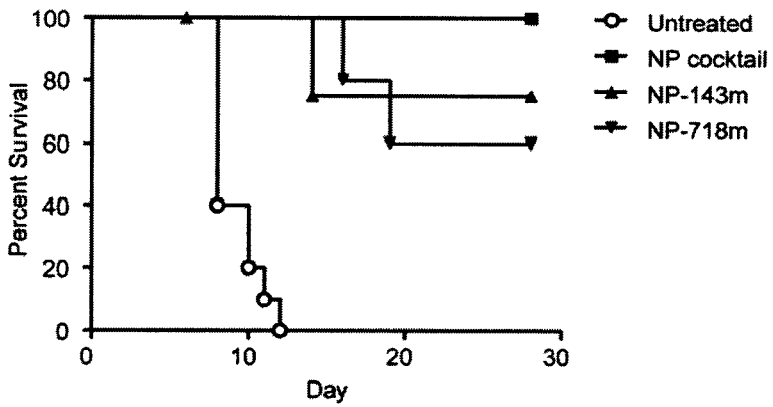

The initial experiment in guinea pigs was designed to test lead siRNA-lipid particles against MARV-Angola, the virus strain that has been responsible for the largest and deadliest human MARV outbreak to date (Towner J S, Khristova M L, Sealy T K, et al. *Marburgvirus* genomics and association with a large hemorrhagic fever outbreak in Angola. J Virol 2006; 80:6497-516). Animals treated with the non-targeting Luc-mod siRNA showed clinical signs indicative of MARV infection with 0% (0/5) survival and fatalities occurring in a time window between days 6 to 8 after virus challenge (FIG. 5A). All animals treated with VP40-320m, VP24-734m and VP24-518m siRNA showed clinical signs of MARV infection with 0% (0/5) survival and fatalities occurring in a time window between days 8 to 11. A survival advantage was shown for animals treated with Lpol-6801m (20% survival, 1/5; clinical signs in all animals) and NP (NP-143m: 40% survival, 2/5, clinical signs in all; NP-718m: 100% survival, 4/4, clinical signs in one animal only). A single fatality (cannibalized by cage mates) occurred at day 15 in the NP-718m treated group but this animal was removed from the survival analysis as this animal appeared stunted prior to infection (FIG. 5B). Survival differences were statistically significant for all comparisons between treated and Luc-control groups (p<0.01; Log-Rank Test with Bonferroni correction for multiple comparisons) with the exception of the VP40-320m treatment. Only treatment with NP-718m was statistically significant (p<0.01) by the Fisher Exact Test. Comparisons between treatment groups and untreated historical controls (n=10; FIG. 7), shows that treatment with NP-718m was statistically significant (Log-Rank Test, p<0.00833 and Fisher Exact Test, p<0.01). Treatment with NP-143m was also found to be statistically significant (p<0.00833; Log-Rank Test).

To determine whether fatalities were due to MARV-Angola infection, the viral load was assessed in plasma samples collected from individual animals at day 7 (FIG. 5B). High viraemia (>7 $\log_{10}$ pfu/mL) was detected from the single control (Luc-mod-treated) animal alive on day 7. Survivors in Lpol and NP treatment groups showed lower viraemia than non-survivors in the Luc-mod control, and VP24 and VP40 treatment groups.

Figure 6:
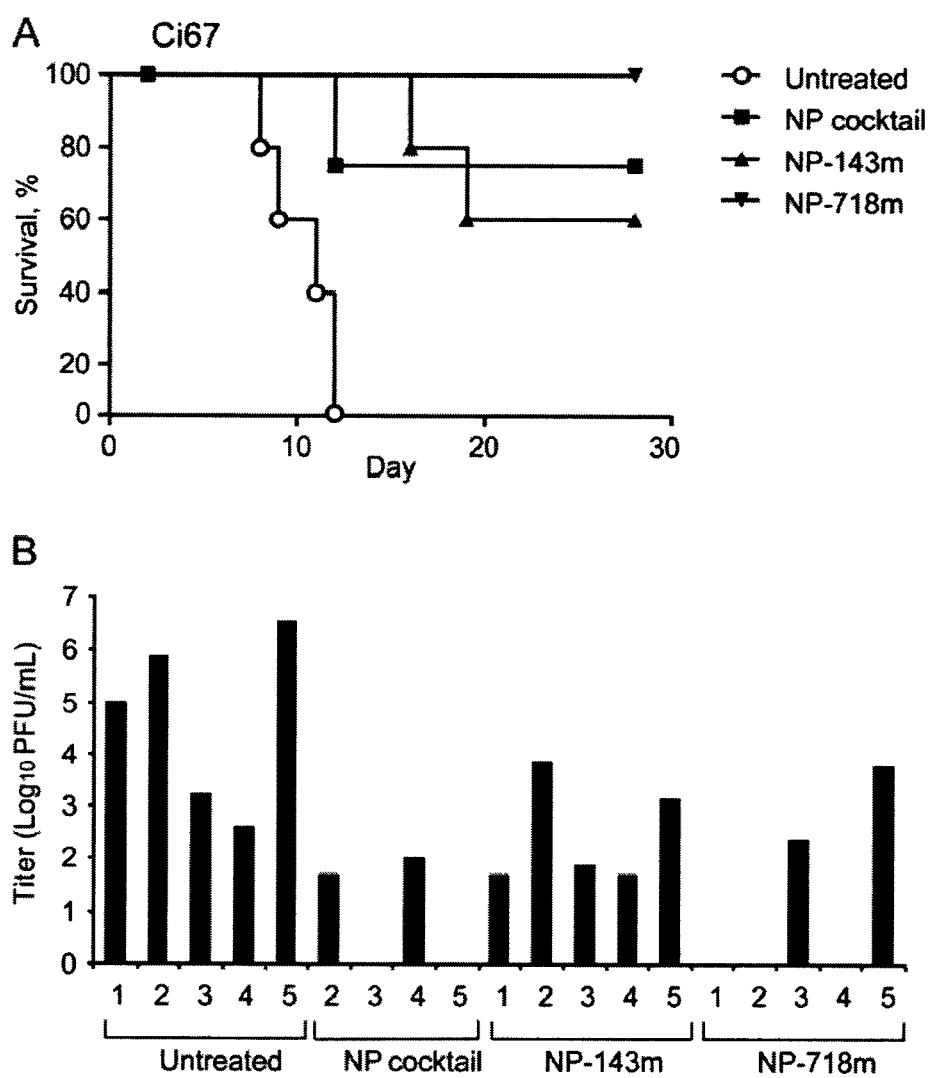
FIG. 6. 2'-O-methylated siRNAs in lipid particles confer protection to guinea pigs against MARV-Ci67 or MARV-Ravn challenge. Survival and viraemia of (A, B) MARV Ci67, (C, D) MARV-Ravn-infected Hartley strain guinea pigs after treatment with lipid particles containing NP-targeting 2-'O-methylated NP siRNA. Animals (n=5 per group) were treated 1 h after viral challenge and treated daily for 6 consecutive days with lipid particles containing 0.5 mg/kg of either individual siRNAs or a 1:1 cocktail of each one of the two siRNAs directed against NP mRNA. Viraemia was not assessed for the following animals: (C: Animal #1 treated with NP cocktail and D Animal #1 treated with NP-143m) as these died prior to collection for viraemia analysis.
Figure 6:
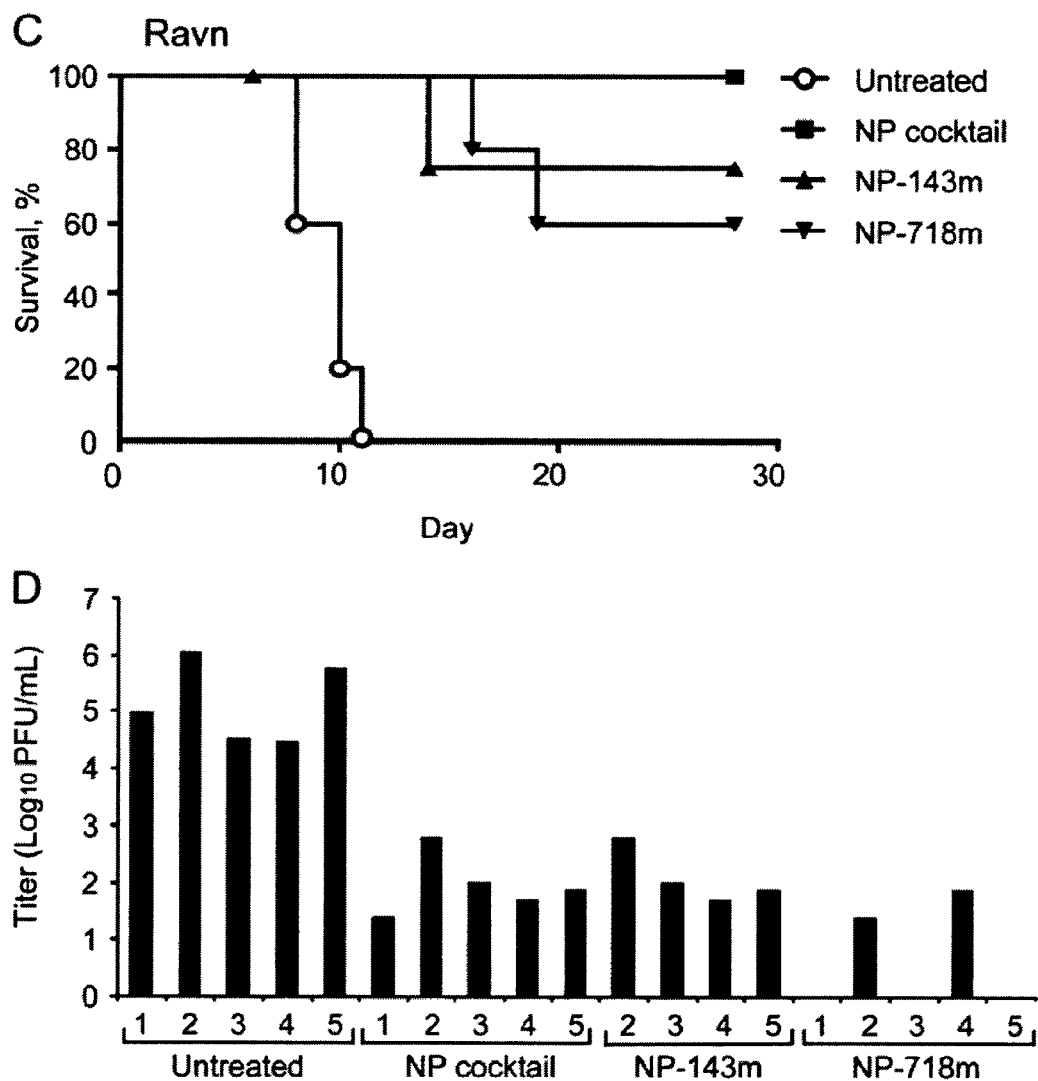

Encouraged by the data from the MARV-Angola challenge, whether protection across a broader spectrum of MARV lineages could be achieved was investigated. To achieve this, the two lead MARV NP siRNA (NP-143m and NP-718m) were combined in one lipid particle for the treatment of animals and then outbred guinea pigs were challenged with MARV-Ci67 or MARV-Ravn (FIG. 6). The NP cocktail lipid particle was tested in parallel with NP-143m and NP-718m lipid particles against MARV-Ci67 (FIG. 6A) or MARV-Ravn (FIG. 6C) in the lethal outbred guinea pig challenge model. Control animals in these studies were not treated with lipid particles and all succumbed to viral infection between days 8 and 12 while showing clinical signs consistent with MARV infection. Survival results in the MARV-Ci67-infected animals corroborated the results seen with MARV-Angola, showing that NP-718m (100% survival; 5/5) is more efficacious than NP-143m (60% survival; 3/5). Survival in the MARV NP cocktail-treated group suggested a dilutive effect of mixing both siRNA (75% survival; 3/4), where the three surviving animals showed clinical signs of virus infection at days 8 and 9 but subsequently recovered (FIG. 6A). However, given the small number of animals that were assessed it is difficult to conclude whether the cocktail treatment was less efficacious (no statistical significance by Log-Rank test). Survival differences were statistically significant for all comparisons between individual siRNA-treated and untreated groups (p<0.0083; Log-Rank Test). Only treatment with NP-718m was statistically significant (p<0.01) by the Fisher Exact Test. High overall virus levels were detected at day 7 in untreated animals, whereas they remained lower in treated animals (FIG. 6B). When animals were infected with MARV-Ravn (FIG. 6C), all untreated animals succumbed to virus infection within days 6 and 11 and showed clinical signs of disease. Animals treated with NP-718m lipid particle achieved 60% (3/5) survival, while animals treated with NP-143m achieved 75% (3/4) survival. Interestingly, all animals in the NP cocktail-treated group survived, despite the presence of a low tolerance mismatch at position 9 in the NP-718m siRNA sequence against the NP mRNA sequence of MARV Ravn. Survival differences were statistically significant for all comparisons between treated and control groups (p<0.00833; Log-Rank Test). Only treatment with NP cocktail was statistically significant (p<0.01) by the Fisher exact test. Comparison between treatment groups and untreated historical controls (n=5 additional animals; FIG. 7), showed that survival differences were statistically significant for all comparisons between treated and untreated groups (p<0.001; Log-Rank Test and p<0.01; Fisher Exact Test). Viral loads detected in control animals at day 7 with MARV-Ci67 or MARV-Ravn were lower than MARV-Angola but otherwise the trends observed in the MARV-Angola study were generally observed in the broad spectrum treatment study with MARV-Ci67 and MARV-Ravn, where control animals showed significantly higher viraemia than NP drug-treated animals. It is unclear why certain animals that showed low or no viraemia on day 7 subsequently succumbed (FIG. 6D).

To more stringently evaluate in vivo efficacy, the ability of NP-718m lipid particle to confer survival benefit in lethally challenged nonhuman primates, a model that more closely recapitulates human disease, was assessed. Rhesus macaques were challenged with MARV-Angola, and treatment with NP-718m lipid particle or a non-virally targeting Luc-mod control lipid particle was initiated at either one hour, one day, two days or three days post-infection. Treatment initiation at increasing times after viral infection in this nonhuman primate model experimentally mimics the clinical patient situation, where the timing of infection is generally unknown and patients at the point of treatment may be seen at various stages of the disease. Animals that were either untreated or treated with the negative control Luc-mod lipid particle succumbed either 7-9 days after infection (untreated, 0% survival, 0/3) or 8 days post-infection (Luc-mod lipid particle, 0% survival, 0/2) and displayed clinical signs of disease (Table 3). All animals treated with NP-718m lipid particle survived infection (100% survival, 16/16) even with a 3 day delay in treatment initiation after infection. Survival differences were statistically significant for all comparisons between treated groups and the negative control Luc-mod groups (p<0.0001) and between treated groups and untreated animals (p<0.0001) by the Fisher Exact Test. High levels of infectious viral particles (as assessed by plaque assay, Table 4) and viral RNA (quantitation by qRT-PCR, Table 5) were observed in animals that were either untreated or administered non-virally targeting Luc-mod lipid particle, whereas animals treated with NP-718m lipid particle showed 4 to 10 log 10 unit reductions in viral load. These reductions were found to be statistically significant by Two-way ANOVA (p<0.0001). Animals that were treated with NP-718m lipid particle also had ameliorated clinical disease signs as assessed by lower clinical scores in a scoring system that measured changes in activity, behavior, food and water intake, weight, respiration, and disease manifestations such as visible rash, hemorrhage, ecchymosis, or flushed skin (Table 6).

TABLE 3

Survival of Rhesus Macaques Lethally Challenged with MARV-Angola Under Various Treatment Conditions

| Treatment | Treatment Initiation Post-Infection | Survival Percentage | No. Survivors | No. Non-survivors |
|---|---|---|---|---|
| Untreated | N/A | 0% | 0 | 2 |
|  | N/A | 0% | 0 | 1 |
| Luc-mod Lipid Particle | 48 hours | 0% | 0 | 1 |
|  | 72 hours | 0% | 0 | 1 |
| NP-718m Lipid Particle | 1 hour | 100% | 4 | 0 |
|  | 24 hours | 100% | 4 | 0 |
|  | 48 hours | 100% | 4 | 0 |
|  | 72 hours | 100% | 4 | 0 |

Abbreviations:
N/A, Not applicable

TABLE 4

Infectious Virus Particle Load of Rhesus Macaques Lethally Challenged with MARV-Angola

| Treatment | Animal ID | Viremia Log(pfu/mL) Days Post-Infection | | | | | | |
|---|---|---|---|---|---|---|---|---|
|  |  | 3 | 6 | 8 | 10 | 14 | 21 | 28 |
| Untreated | 308904 | 2.00 | TNTC | X | X | X | X | X |
|  | 904099 | 0.00 | 7.10 | 7.89 | X | X | X | X |
| Luc-mod Lipid Particle | 707061 | 0.00 | 5.58 | 7.11 | X | X | X | X |
|  | 0907042 | 0.00 | 6.50 | 7.58 | X | X | X | X |
|  | 0903269 | 1.22 | 7.45 | 7.01 | X | X | X | X |
| NP-718m Lipid Particle | 8083572 | 0.00 | 0.00 | N/C | 0.00 | 0.00 | 0.00 | 0.00 |
|  | 906057 | 0.00 | 0.00 | N/C | 2.99 | 0.00 | 0.00 | 0.00 |
|  | R080062 | 0.00 | 0.00 | N/C | 0.00 | 0.00 | 0.00 | 0.00 |
|  | 908097 | 0.00 | 0.00 | N/C | 3.48 | 0.00 | 0.00 | 0.00 |
|  | 806012 | 0.00 | 0.00 | N/C | 0.00 | 0.00 | 0.00 | 0.00 |
|  | 704019 | 0.00 | 0.00 | N/C | 0.00 | 0.00 | 0.00 | 0.00 |
|  | 908021 | 0.00 | 0.00 | N/C | 0.00 | 0.00 | 0.00 | 0.00 |
|  | 08R0002 | 0.00 | 0.00 | N/C | 0.00 | 0.00 | 0.00 | 0.00 |
|  | 904047 | 0.00 | 0.00 | N/C | 0.00 | 0.00 | 0.00 | 0.00 |
|  | 1002065 | 0.00 | 0.00 | N/C | 0.00 | 0.00 | 0.00 | 0.00 |
|  | 705010 | 0.00 | 0.00 | N/C | 0.00 | 0.00 | 0.00 | 0.00 |
|  | 904088 | 0.00 | 0.00 | N/C | 0.00 | 0.00 | 0.00 | 0.00 |
|  | 0906220 | 0.00 | 0.92 | N/C | 0.00 | 0.00 | 0.00 | 0.00 |
|  | 0810254 | 0.00 | 1.40 | N/C | 0.00 | 0.00 | 0.00 | 0.00 |
|  | 0906145 | 0.00 | 0.00 | N/C | 0.00 | 0.00 | 0.00 | 0.00 |
|  | 0807175 | 0.00 | 2.12 | N/C | 0.00 | 0.00 | 0.00 | 0.00 |

Abbreviations:
N/C, Not collected; X, No sample due to animal euthanization

TABLE 5

Viral RNA Load of Rhesus Macaques Lethally Challenged with MARV-Angola

| Treatment | Animal ID | Viral RNA Log(Genomic Equivalents/mL) Days Post-Infection | | | | | | |
|---|---|---|---|---|---|---|---|---|
|  |  | 3 | 6 | 8 | 10 | 14 | 21 | 28 |
| Untreated | 308904 | 6.09 | 10.30 | X | X | X | X | X |
|  | 904099 | 6.25 | 10.39 | 11.40 | X | X | X | X |
| Luc-mod Lipid Particle | 707061 | <LLOQ | 8.80 | 11.07 | X | X | X | X |
|  | 0907042 | <LLOQ | 9.97 | 8.87 | X | X | X | X |
|  | 0903269 | 4.84 | 11.49 | 10.45 | X | X | X | X |
| NP-718m Lipid Particle | 8083572 | <LLOQ | <LLOQ | N/C | <LLOQ | <LLOQ | <LLOQ | <LLOQ |
|  | 906057 | <LLOQ | <LLOQ | N/C | 6.42 | <LLOQ | <LLOQ | <LLOQ |
|  | R080062 | <LLOQ | <LLOQ | N/C | 6.35 | <LLOQ | <LLOQ | <LLOQ |
|  | 908097 | <LLOQ | 6.04 | N/C | 7.47 | <LLOQ | <LLOQ | <LLOQ |
|  | 806012 | <LLOQ | <LLOQ | N/C | <LLOQ | <LLOQ | <LLOQ | <LLOQ |
|  | 704019 | <LLOQ | <LLOQ | N/C | <LLOQ | <LLOQ | <LLOQ | <LLOQ |
|  | 908021 | <LLOQ | <LLOQ | N/C | <LLOQ | <LLOQ | <LLOQ | <LLOQ |
|  | 08R0002 | <LLOQ | <LLOQ | N/C | <LLOQ | <LLOQ | <LLOQ | <LLOQ |
|  | 904047 | <LLOQ | <LLOQ | N/C | <LLOQ | <LLOQ | <LLOQ | <LLOQ |
|  | 1002065 | <LLOQ | <LLOQ | N/C | <LLOQ | <LLOQ | <LLOQ | <LLOQ |

TABLE 5-continued

Viral RNA Load of Rhesus Macaques Lethally Challenged with MARV-Angola

| Treatment | Animal ID | Viral RNA Log(Genomic Equivalents/mL) Days Post-Infection | | | | | | |
|---|---|---|---|---|---|---|---|---|
| | | 3 | 6 | 8 | 10 | 14 | 21 | 28 |
| | 705010 | <LLOQ | <LLOQ | N/C | <LLOQ | <LLOQ | <LLOQ | <LLOQ |
| | 904088 | <LLOQ | <LLOQ | N/C | <LLOQ | <LLOQ | <LLOQ | <LLOQ |
| | 0906220 | LLOQ | <LLOQ | N/C | <LLOQ | <LLOQ | <LLOQ | <LLOQ |
| | 0810254 | 5.25 | <LLOQ | N/C | <LLOQ | <LLOQ | <LLOQ | <LLOQ |
| | 0906145 | <LLOQ | <LLOQ | N/C | <LLOQ | <LLOQ | <LLOQ | <LLOQ |
| | 0807175 | 6.01 | 6.24 | N/C | 6.14 | <LLOQ | <LLOQ | <LLOQ |

Abbreviations:
<LLOQ, Below lower limit of quantitation; N/C, Not collected; X, No sample due to animal euthanization

TABLE 6

Clinical Scores of Rhesus Macaques Lethally Challenged with MARV-Angola

| Treatment | Animal ID | Days Post-Infection | | | | | | | | | | | | | | | | | |
|---|---|---|---|---|---|---|---|---|---|---|---|---|---|---|---|---|---|---|---|
| | | 0 | 1 | 2 | 3 | 4 | 5 | 6 | 7 | 8 | 9 | 10 | 11 | 12 | 13 | 14 | 15 | 16 | 17 | 18 |
| Untreated | 308904 | 0 | 0 | 0 | 0 | 0 | 0 | 0 | 3 | X | X | X | X | X | X | X | X | X | X | X |
| | 904099 | 0 | 0 | 0 | 0 | 0 | 0 | 0 | 1 | 14 | X | X | X | X | X | X | X | X | X | X |
| Luc-mod Lipid Particle | 707061 | 0 | 0 | 0 | 0 | 0 | 0 | 0 | 0 | 1 | 14 | X | X | X | X | X | X | X | X | X |
| | 0907042 | 0 | 0 | 0 | 0 | 0 | 0 | 3 | 4 | 9 | X | X | X | X | X | X | X | X | X | X |
| | 0903269 | 0 | 0 | 0 | 0 | 0 | 0 | 1 | 3 | 15 | X | X | X | X | X | X | X | X | X | X |
| NP-718m Lipid Particle | 8083572 | 0 | 0 | 0 | 0 | 0 | 0 | 0 | 0 | 0 | 0 | 0 | 0 | 0 | 0 | 0 | 0 | 0 | 0 | 0 |
| | 906057 | 0 | 0 | 0 | 0 | 0 | 0 | 0 | 0 | 0 | 0 | 0 | 0 | 0 | 0 | 0 | 0 | 0 | 0 | 0 |
| | R080062 | 0 | 0 | 0 | 0 | 0 | 0 | 0 | 0 | 0 | 0 | 0 | 0 | 0 | 0 | 0 | 0 | 0 | 0 | 0 |
| | 908097 | 0 | 0 | 0 | 0 | 0 | 0 | 0 | 0 | 0 | 0 | 0 | 0 | 0 | 0 | 0 | 0 | 0 | 0 | 0 |
| | 806012 | 0 | 0 | 0 | 0 | 0 | 0 | 0 | 0 | 0 | 0 | 0 | 0 | 0 | 0 | 0 | 0 | 0 | 0 | 0 |
| | 704019 | 0 | 0 | 0 | 0 | 0 | 0 | 0 | 0 | 0 | 0 | 0 | 0 | 0 | 0 | 0 | 0 | 0 | 0 | 0 |
| | 908021 | 0 | 0 | 0 | 0 | 0 | 0 | 0 | 0 | 0 | 0 | 0 | 0 | 0 | 0 | 0 | 0 | 0 | 0 | 0 |
| | 08R0002 | 0 | 0 | 0 | 0 | 0 | 0 | 0 | 0 | 0 | 0 | 0 | 0 | 0 | 0 | 0 | 0 | 0 | 0 | 0 |
| | 904047 | 0 | 0 | 0 | 0 | 0 | 0 | 0 | 0 | 0 | 0 | 0 | 0 | 0 | 0 | 0 | 0 | 0 | 0 | 0 |
| | 1002065 | 0 | 0 | 0 | 0 | 0 | 0 | 0 | 0 | 0 | 0 | 0 | 0 | 0 | 0 | 0 | 0 | 0 | 0 | 0 |
| | 705010 | 0 | 0 | 0 | 0 | 0 | 0 | 0 | 0 | 0 | 0 | 0 | 0 | 0 | 0 | 0 | 0 | 0 | 0 | 0 |
| | 904088 | 0 | 0 | 0 | 0 | 0 | 0 | 0 | 0 | 0 | 0 | 0 | 0 | 0 | 0 | 0 | 0 | 0 | 0 | 0 |
| | 0906220 | 0 | 0 | 0 | 0 | 0 | 0 | 0 | 0 | 0 | 0 | 0 | 0 | 0 | 0 | 0 | 0 | 0 | 0 | 0 |
| | 0810254 | 0 | 0 | 0 | 0 | 0 | 0 | 0 | 0 | 0 | 0 | 0 | 0 | 0 | 0 | 0 | 0 | 0 | 0 | 0 |
| | 0906145 | 0 | 0 | 0 | 0 | 0 | 0 | 0 | 0 | 0 | 0 | 0 | 0 | 0 | 0 | 0 | 0 | 0 | 0 | 0 |
| | 0807175 | 0 | 0 | 0 | 0 | 0 | 1 | 1 | 1 | 1 | 1 | 1 | 1 | 0 | 0 | 0 | 0 | 0 | 0 | 0 |

Abbreviations:
X, No sample due to animal euthanization
Clinical Scores:
0 = No signs observed; 1-2 = Mild; 3-8 = Moderate; ≥9 = Meets euthanasia criteria

DISCUSSION

The development and evaluation of lipid-encapsulated siRNA (nucleic acid-lipid particles) as a potential therapeutic agent against a broad spectrum of MARVs is presented herein. As a precursor to in vivo studies, RNAi activity of anti-MARV siRNA was initially assessed using dual luciferase reporter assays followed by in vitro testing against live virus. Lead candidates were tested in newly developed lethal outbred guinea pig models of MARV-Angola, MARV-Ci67 or MARV-Ravn infection, with MARV-Angola being the most lethal MARV strain to date. The data show that siRNA targeting MARV NP mRNA delivered by lipid particles is a promising post-exposure treatment strategy where treatment resulted in 60-100% survival in guinea pigs infected with MARV strains Angola, Ci67, or Ravn. Although treatment with siRNA targeting other viral mRNA had a positive effect on survival of the animals, targeting the NP viral mRNA resulted in the highest survival rates.

Until now, substantial protection against the most lethal MARV strain, Angola, has not yet been shown using any therapeutic candidate. Here, it is shown that MARV NP-718m siRNA in lipid particles provided 100% protection against MARV-Ci67 and MARV-Angola in both a guinea pig model of MARV infection, as well as in the rhesus macaque nonhuman primate model, which more closely recapitulates human disease.

In the guinea pig model of viral infection, the MARV NP-718m lipid particle is more efficacious than NP-143m against strains where no nucleotide mismatches exist between the antisense strand and the target mRNA (strains Angola and Ci67). This difference in efficacy is absent when NP-718m is used as a single drug component to treat a MARV-Ravn infection (60% survival). In this case a single nucleotide mismatch exists (U-G) in a low mismatch tolerance position (nucleotide 9 of the antisense strand) (Ahmed F, Raghava G P. Designing of highly effective complementary and mismatch siRNAs for silencing a gene. PLoS One 2011; 6:e23443). Despite this mismatch NP-718m siRNA remained active against MARV-Ravn. Interestingly, in animals infected with MARV-Ravn, the cocktail of NP-718m and NP-143m siRNA in lipid particles provided 100% survival whereas survival was lower using either of these siRNA alone.

Multivalent antiviral therapy, whereby multiple nucleic acid drug components have been used to target different viral mRNA in the treatment of filovirus infections has been used with some success (Warren T K, Warfield K L, Wells J, et al. Advanced antisense therapies for postexposure protection against lethal filovirus infections. Nat Med 2010; 16:991-4; Geisbert T W, Lee A C, Robbins M, et al. Postexposure protection of non-human primates against a lethal Ebola virus challenge with RNA interference: a proof-of-concept study. Lancet 2010; 375:1896-905). Here, two different siRNAs are described which were combined in an attempt to provide broader spectrum antiviral activity, and despite one of the siRNAs being less efficacious when used alone, complete protection against MARV Ravn was provided in the guinea pig model of viral infection.

Further confirmation of therapeutic benefit was demonstrated in the stringent nonhuman primate model of lethal MARV-Angola challenge, which represents a potential patient worst case scenario of high viral loads and shortened infection time course with a fatal outcome. Treatment with NP-718m lipid particle was able to confer survival benefit and significantly reduce viral load in infected animals (Thi E P, Mire C E, Ursic-Bedoya R, et al. Marburg virus infection in nonhuman primates: Therapeutic treatment by lipid-encapsulated siRNA. Sci Trans Med 2014; 6(250): 250ra116). Additional advantages by ameliorating disease symptoms were also observed in animals treated with NP-718m lipid particle. This ability to confer therapeutic protection after viral infection, even when initiation of treatment is delayed until three days post-infection, is significant as this represents the earliest disease phase in this animal model wherein animals are beginning to display signs of disease and the infection can be diagnosed through qRT-PCR assessment of blood samples. This represents the first documented instance whereby a therapeutic treatment is able to confer protection against MARV-Angola infection when treatment was initiated at a point when nonhuman primates were symptomatic for disease.

All publications cited herein are incorporated herein by reference. While in this application certain embodiments of invention have been described, and many details have been set forth for purposes of illustration, it will be apparent to those skilled in the art that certain of the details described herein may be varied without departing from the basic principles of the invention.

The use of the terms "a" and "an" and "the" and similar terms in the context of describing embodiments of invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. In addition to the order detailed herein, the methods described herein can be performed in any suitable order unless otherwise indicated herein or otherwise clearly contradicted by context. The use of any and all examples, or exemplary language (e.g., "such as") provided herein, is intended merely to better illuminate embodiments of invention and does not pose a limitation on the scope of the invention unless otherwise specifically recited in the claims. No language in the specification should be construed as indicating that any non-claimed element as essential to the practice of the invention.

What is claimed is:

1. An isolated, single-stranded, RNA molecule consisting of a sequence selected from SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23 and SEQ ID NO:24.

2. An isolated, double-stranded, siRNA molecule selected from the group consisting of Lpol-6801m (SEQ ID NO:13 and 14), VP40-320m (SEQ ID NO:15 and 16), VP24-518m (SEQ ID NO:17 and 18), VP24-734m (SEQ ID NO:19 and 20), NP-143m (SEQ ID NO:21 and 22) and NP-718m (SEQ ID NO:23 and 24).

3. A composition comprising an isolated, double-stranded, siRNA of claim 2.

4. The composition of claim 3 comprising two different double-stranded siRNAs selected from the group consisting of Lpol-6801m (SEQ ID NO:13 and 14), VP40-320m (SEQ ID NO:15 and 16), VP24-518m (SEQ ID NO:17 and 18), VP24-734m (SEQ ID NO:19 and 20), NP-143m (SEQ ID NO:21 and 22) and NP-718m (SEQ ID NO:23 and 24).

5. The composition of claim 4, wherein the double stranded siRNAs are NP-143m (SEQ ID NO:21 and 22) and NP-718m (SEQ ID NO:23 and 24).

6. The composition of claim 3, wherein the composition is a pharmaceutical composition that comprises a pharmaceutically acceptable carrier.

7. A nucleic acid-lipid particle, comprising:

(a) one or more isolated, double-stranded, siRNA molecules selected from the isolated, double-stranded, siRNA molecules of claim 2;

(b) a cationic lipid; and (c) a non-cationic lipid.

8. The nucleic acid-lipid particle of claim 7, wherein the cationic lipid is selected from the group consisting of 1,2-dilinoleyloxy-N,N-dimethylaminopropane (DLinDMA), 1,2-dilinolenyloxy-N,N-dimethylaminopropane (DLenDMA), 1,2-di-γ-linolenyloxy-N,N-dimethylaminopropane (γ-DLenDMA), 3-((6Z,9Z,28Z,31Z)-heptatriaconta-6,9,28,31-tetraen-19-yloxy)-N,N-dimethylpropan-1-amine (DLin-MP-DMA), MC3 ((6Z,9Z,28Z,31Z)-heptatriaconta-6,9,28,31-tetraen-19-yl 4-(dimethylamino) butanoate), (6Z,16Z)-12-((Z)-dec-4-enyl)docosa-6,16-dien-11-yl 5-(dimethylamino)pentanoate, a salt thereof, or a mixture thereof.

9. The nucleic acid-lipid particle of claim 7, wherein the non-cationic lipid is a phospholipid, cholesterol or a derivative thereof, or a mixture of a phospholipid and cholesterol or a derivative thereof.

10. The nucleic acid-lipid particle of claim 9, wherein the non-cationic lipid is a phospholipid; and wherein the phospholipid comprises dipalmitoylphosphatidylcholine (DPPC), distearoylphosphatidylcholine (DSPC), or a mixture thereof.

11. The nucleic acid-lipid particle of claim 7, wherein the non-cationic lipid is a mixture of DPPC and cholesterol.

12. The nucleic acid-lipid particle of claim 7, further comprising a conjugated lipid that inhibits aggregation of particles.

13. The nucleic acid-lipid particle of claim 12, wherein the conjugated lipid that inhibits aggregation of particles is a polyethyleneglycol (PEG)-lipid conjugate selected from the group consisting of a PEG-diacylglycerol (PEG-DAG) conjugate, a PEG-dialkyloxypropyl (PEG-DAA) conjugate, a PEG-phospholipid conjugate, a PEG-ceramide (PEG-Cer) conjugate, and a mixture thereof.

14. The nucleic acid-lipid particle of claim 13, wherein the PEG-lipid conjugate is a PEG-DAA conjugate selected from the group consisting of a PEG-didecyloxypropyl ($C_{10}$) conjugate, a PEG-dilauryloxypropyl ($C_{12}$) conjugate, a PEG-dimyristyloxypropyl ($C_{14}$) conjugate, a PEG-dipalmityloxypropyl ($C_{16}$) conjugate, a PEG-distearyloxypropyl ($C_{18}$) conjugate, and a mixture thereof.

15. The nucleic acid-lipid particle of claim 7 comprising two different siRNA molecules selected from the group consisting of Lpol-6801m (SEQ ID NO:13 and 14), VP40-320m (SEQ ID NO:15 and 16), VP24-518m (SEQ ID NO:17 and 18), VP24-734m (SEQ ID NO:19 and 20), NP-143m (SEQ ID NO:21 and 22) and NP-718m (SEQ ID NO:23 and 24).

16. The nucleic acid-lipid particle of claim 15, wherein the two different siRNA molecules are NP-143m (SEQ ID NO:21 and 22) and NP-718m (SEQ ID NO:23 and 24).

17. A pharmaceutical composition comprising the nucleic acid-lipid particle of claim 7 and a pharmaceutically acceptable carrier.

18. A method for introducing an siRNA that silences expression of a Marburg virus gene into a cell, the method comprising the step of contacting the cell with the nucleic acid-lipid particle of claim 7 under conditions whereby the siRNA enters the cell and silences the expression of the Marburg virus gene within the cell.

19. A method for ameliorating one or more symptoms associated with Marburg virus infection in a human, the method comprising the step of administering to the human a therapeutically effective amount of the nucleic acid-lipid particle of claim 7.

20. A method for introducing an siRNA that silences expression of a Marburg virus gene into a cell, the method comprising the step of contacting the cell with the composition of claim 3 under conditions whereby the siRNA enters the cell and silences the expression of the Marburg virus gene within the cell.

21. A method for ameliorating one or more symptoms associated with Marburg virus infection in a human, the method comprising the step of administering to the human a therapeutically effective amount of the composition of claim 3.

* * * * *

SEQUENCE LISTING

```
<160> NUMBER OF SEQ ID NOS: 32

<210> SEQ ID NO 1
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
cgucaaggca aacaacauuu a                                          21

<210> SEQ ID NO 2
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
aauguuguuu gccuugacga a                                          21

<210> SEQ ID NO 3
<211> LENGTH: 21
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 3
gucugccaug cuuucacuuu a                                              21

<210> SEQ ID NO 4
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
aagugaaagc auggcagaca u                                              21

<210> SEQ ID NO 5
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
ccaagaauua cagcaaucau u                                              21

<210> SEQ ID NO 6
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
ugauugcugu aauucuuggu c                                              21

<210> SEQ ID NO 7
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
ccagcaguau ugaaauaaag u                                              21

<210> SEQ ID NO 8
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
uuuauuucaa uacugcuggg u                                              21

<210> SEQ ID NO 9
<211> LENGTH: 21
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 9
ucagguuagu aucuguaauc a                                                  21

<210> SEQ ID NO 10
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
auuacagaua cuaaccugau g                                                  21

<210> SEQ ID NO 11
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
gauucucagg acuucuuauu g                                                  21

<210> SEQ ID NO 12
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
auaagaaguc cugagaaucu a                                                  21

<210> SEQ ID NO 13
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (7)..(8)
<223> OTHER INFORMATION: 2'-O-Methyl nucleotide
<220> FEATURE:
<221> NAME/KEY: modified_base
<222> LOCATION: (18)..(20)
<223> OTHER INFORMATION: 2'-O-Methyl nucleotide

<400> SEQUENCE: 13
cgucaaggca aacaacauuu a                                                  21

<210> SEQ ID NO 14
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:

```
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (7)..(7)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-O-Methyl nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (19)..(19)
<223> OTHER INFORMATION: 2'-O-Methyl nucleotide

<400> SEQUENCE: 14
aauguuguuu gccuugacga a                                              21

<210> SEQ ID NO 15
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-O-Methyl nucleotide
<220> FEATURE:
<221> NAME/KEY: modified_base
<222> LOCATION: (20)..(20)
<223> OTHER INFORMATION: 2'-O-Methyl nucleotide

<400> SEQUENCE: 15
gucugccaug cuuucacuuu a                                              21

<210> SEQ ID NO 16
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-O-Methyl nucleotide
<220> FEATURE:
<221> NAME/KEY: modified_base
<222> LOCATION: (12)..(13)
<223> OTHER INFORMATION: 2'-O-Methyl nucleotide
<220> FEATURE:
<221> NAME/KEY: modified_base
```

```
<222> LOCATION: (17)..(17)
<223> OTHER INFORMATION: 2'-O-Methyl nucleotide
<220> FEATURE:
<221> NAME/KEY: modified_base
<222> LOCATION: (21)..(21)
<223> OTHER INFORMATION: 2'-O-Methyl nucleotide

<400> SEQUENCE: 16
aagugaaagc auggcagaca u                                      21

<210> SEQ ID NO 17
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: 2'-O-Methyl nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 17
ccaagaauua cagcaaucau u                                      21

<210> SEQ ID NO 18
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-O-Methyl nucleotide
<220> FEATURE:
<221> NAME/KEY: modified_base
<222> LOCATION: (20)..(20)
<223> OTHER INFORMATION: 2'-O-Methyl nucleotide

<400> SEQUENCE: 18
ugauugcugu aauucuuggu c                                      21

<210> SEQ ID NO 19
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (11)..(11)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-O-Methyl nucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 19
ccagcaguau ugaaauaaag u                                              21

<210> SEQ ID NO 20
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-O-Methyl nucleotide
<220> FEATURE:
<221> NAME/KEY: modified_base
<222> LOCATION: (7)..(7)
<223> OTHER INFORMATION: 2'-O-Methyl nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 20
uuuauuucaa uacugcuggg u                                              21

<210> SEQ ID NO 21
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
```

<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-O-Methyl nucleotide
<220> FEATURE:
<221> NAME/KEY: modified_base
<222> LOCATION: (7)..(7)
<223> OTHER INFORMATION: 2'-O-Methyl nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (19)..(19)
<223> OTHER INFORMATION: 2'-O-Methyl nucleotide

<400> SEQUENCE: 21
ucagguuagu aucuguaauc a                                           21

<210> SEQ ID NO 22
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-O-Methyl nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 22
auuacagaua cuaaccugau g                                           21

<210> SEQ ID NO 23
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (6)..(6)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-O-Methyl nucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 23
gauucucagg acuucuuauu g                                               21

<210> SEQ ID NO 24
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: 2'-O-Methyl nucleotide
<220> FEATURE:
<221> NAME/KEY: modified_base
<222> LOCATION: (8)..(9)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-O-Methyl nucleotide
<220> FEATURE:
<221> NAME/KEY: modified_base
<222> LOCATION: (20)..(20)
<223> OTHER INFORMATION: 2'-O-Methyl nucleotide

<400> SEQUENCE: 24
auaagaaguc cugagaaucu a                                               21

<210> SEQ ID NO 25
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
gcaagaucau gcggaaacug g                                               21

<210> SEQ ID NO 26
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26 aguuccgca ugaucuugcu u                                                21

<210> SEQ ID NO 27
<211> LENGTH: 21
<212> TYPE: RNA
<213> ORGANISM: Artificial Sequence
<220> FEATURE:
<223> OTHER INFORMATION: Description of Artificial Sequence: Synthetic

```
      oligonucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-O-Methyl nucleotide

<400> SEQUENCE: 27 agugcauca cacugaauac c                                              21

<210> SEQ ID NO 28
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (7)..(7)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-O-Methyl nucleotide
<220> FEATURE:
<221> NAME/KEY: modified_base
<222> LOCATION: (19)..(19)
<223> OTHER INFORMATION: 2'-O-Methyl nucleotide

<400> SEQUENCE: 28
uauucagugu gaugacacuu g                                             21

<210> SEQ ID NO 29
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
gauuaugucc gguuauguaa a                                             21

<210> SEQ ID NO 30
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
uacauaaccg gacauaauca u                                             21

<210> SEQ ID NO 31
<211> LENGTH: 21
<212> TYPE: RNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: modified_base
<222> LOCATION: (3)..(4)
<223> OTHER INFORMATION: 2'-O-Methyl nucleotide
<220> FEATURE:
<221> NAME/KEY: modified_base
<222> LOCATION: (6)..(6)
<223> OTHER INFORMATION: 2'-O-Methyl nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (13)..(14)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-O-Methyl nucleotide

<400> SEQUENCE: 31
gauuaugucc gguuauguaa a                                              21

<210> SEQ ID NO 32
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: 2'-O-Methyl nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-O-Methyl nucleotide

<400> SEQUENCE: 32
uacauaaccg gacauaauca u                                              21
```